US006713619B1

(12) United States Patent
Weinberg et al.

(10) Patent No.: US 6,713,619 B1
(45) Date of Patent: Mar. 30, 2004

(54) ONCOGENES AND METHODS FOR THEIR DETECTION

(75) Inventors: Robert A. Weinberg, Brookline, MA (US); Clifford J. Tabin, Cambridge, MA (US); Scott M. Bradley, McLean, VA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1,086 days.

(21) Appl. No.: 08/308,193

(22) Filed: Sep. 19, 1994

Related U.S. Application Data

(63) Continuation of application No. 07/880,483, filed on May 6, 1992, now abandoned, and a continuation of application No. 07/772,614, filed on Oct. 8, 1991, now abandoned, and a continuation of application No. 07/228,392, filed on Aug. 4, 1988, now abandoned, and a continuation-in-part of application No. 06/871,102, filed on Jun. 4, 1986, now Pat. No. 4,935,341, and a continuation-in-part of application No. 06/828,599, filed on Feb. 11, 1986, now abandoned, and a continuation of application No. 06/765,362, filed on Aug. 13, 1985, now abandoned, and a continuation-in-part of application No. 06/432,337, filed on Oct. 1, 1982, now Pat. No. 4,535,058, and a continuation of application No. 06/379,721, filed on May 19, 1982, now abandoned, and a continuation-in-part of application No. 06/182,501, filed on Aug. 29, 1980, now Pat. No. 4,353,153.

(51) Int. Cl.$^7$ .............................................. C07H 21/04
(52) U.S. Cl. ................. 536/24.3; 536/24.31; 536/24.32
(58) Field of Search ...................... 435/6, 5; 536/23.72, 536/24.31, 24.32

(56) References Cited

U.S. PATENT DOCUMENTS

| | | | |
|---|---|---|---|
| 4,172,124 A | | 10/1979 | Koprowski et al. |
| 4,299,815 A | | 11/1981 | Hansen et al. |
| 4,368,262 A | | 1/1983 | Bucovaz et al. |
| 4,381,292 A | * | 4/1983 | Bieber et al. ................... 435/7 |
| 4,395,486 A | | 7/1983 | Wilson et al. |
| 4,447,545 A | * | 5/1984 | DeFazio et al. ............... 435/7 |
| 4,535,058 A | * | 8/1985 | Weinberg et al. ............... 435/6 |
| 4,665,018 A | * | 5/1987 | Vold ............................... 435/6 |
| 4,786,718 A | | 11/1988 | Weinberg et al. |
| 4,935,341 A | * | 6/1990 | Bargmann et al. ............. 435/6 |

FOREIGN PATENT DOCUMENTS

| | | |
|---|---|---|
| EP | 0108564 | 5/1984 |
| WO | 84/01389 | 4/1984 |
| WO | 87/07646 | 12/1987 |

OTHER PUBLICATIONS

Wallace et al; Nucleic Acids Res. 6(11), 3543 (1979).*
DeFeo et al; Proc. Natl. Acad. Sci. USA 78(6), 3328 (1981).*
Akiyama, et al., Science 232:1644–1646 (1986).
Bargmann, et al., Chem. Abstract 105(7).
Bargmann, et al., Cell 45:649–657 (1986).
Bargmann, et al., Nature 319:226–230 (1986).
Bargmann, et al., Journal of Cellular Biochemistry, Supplement 10C, 1986 UCLA Symposia on Molecular & Cellular Biology Abstracts 15th Annual Meetings .
Bargmann, et al., 37. Colloquium der Gesellschaft fur Biologishe Chemie, "Cell Cycle and Oncogenes", Springer–Verlag 1986.
Berger, et al., Cancer Research 48:1238–1243 (1988).
Weinberg, "Use of Transfection to Analyze Genetic Information and Malignant Transformation" Biochemica et Biophysica Acta 651:25–35 (1981), Elsevier/North–Holland Biomedical Press.
Butler, et al., "Gene Control in the Living Cells", Basic Books pp. 125–127 (1968).
Carney, et al., AACC Abstract (1988).
Courtneidge, et al., Proc. Natl. Acad. Sci. USA 88:3788 (1980).
Coussens, et al., Science 230:1132–1139 (1985).
DiFiore, et al., Science 237:178–182 (1987).
Dhar, et al., Science 217:934–937 (1982).
Drebin, et al., Nature 312:545–548 (1984).
Drebin, et al., Cell 41:695–706 (1985).
Drebin, et al., Oncogene 2:273–277 (1988).
Drebin, et al., Oncogene 2:387–394 (1988).
Drebin, et al., Chem. Abstract 106:31140g (1987).
Drebin, et al., Chem. Abstract 108:184829e (1988).
Ellis, et al., J. Virol. 36:408 (1980).
Fukushige, et al., Mol. Cell. Biol. 6:955–958 (1986).
Furth, et al., J. Virol. 43(1):294–304 (1982).
Gibbs, et al., TIBS pp. 350–353 (1985).
Gullick, et al., J. Cancer 40:246–254 (1987).
Guerro, et al., Science 225:1159–1162.
Hung, et al., Proc. Natl. Acad. Sci. USA 83:261–264 (1986).
King, et al., Science 229:974–976 (1985).
Kraus, et al., The EMBO Journal, vol. 6, No. 3, pp. 605–610.
Marx, Science 223:673–676 (1984).
Murray, Cell 25:355–361 (1981).
Papageorge, et al., J. Virol. 44(2):509–519 (1982).
Perucho, Cell 27:467–476 (1981).
Shechter, et al., Science 229:976–978 (1985).
Schechter, et al., Nature 312:513–516 (1984).
Seeger, et al., N. Engl. J. Med. 313(8):1111–1116 1985).
Semba, et al., Proc. Natl. Acad. Sci. USA 82:6497–6501 (1985).

(List continued on next page.)

Primary Examiner—Kenneth R. Horlick
(74) Attorney, Agent, or Firm—John P. White; Cooper & Dunham LLP

(57) ABSTRACT

Experiments designed to define the differences between the 21 oncogene of DNA isolated from human bladder cancer cells and its corresponding proto-oncogene are described herein. Also described is the determination of the difference between the rat neu oncogene and its corresponding proto-oncogene. Also described are nucleic acid probes reactive with regions of the proto-oncogene or oncogene, as are methods for their use in detecting the occurrence of the two types of genes. Antibodies specific for gene products encoded by the neu genes are also described, as are methods for their use.

2 Claims, 24 Drawing Sheets

OTHER PUBLICATIONS

Shih, et al., Cell 29:161–169 (1982).
Shih, et al., Nature 290:261–264 (1981).
Shih, et al., Virology 96:64–79 (1979).
Slamon, et al., Science 235:177–182 (1987).
Studencki, et al., DNA, vol. 3, No. 1, pp. 7–15 (1984).
Trimpe, et al., Abstract presented at Cold Spring Harbor Laboratory Meeting (1988).
Tsuchida, et al., Science 217:937–939 (1982).
Van de Vijer, et al., Molecular and Cellular Biology, vol. 7, No. 5 pp. 2019–2023 (1987).
Van de Vijer, et al., Chem. Abstract 107:1863y (1987).
Varley, et al., Oncogene 1:423–430 (1987).
Venter, et al., The Lancet, ii, pp. 69–72 (1987).
Wallace, et al., Nucleic Acids Res. 6(11):3543 (1979).
Weinberg, et al., 27 Mosbacher Kolloquium der Gesellschaft fur Biologische Chemie, "Cell Cycle and Oncogenes" Abstract, Apr. 10, 1986—Apr. 12, 1986.
Wigler, et al., Cell 14:725–831 (1978).
Wong, et al., Oncogene 2:67–72 (1987).
Yamamoto, et al., Nature 319:230–234 (1986).
Yokota, et al., The Lancet, 765–767 (1986).
Shilo, et al., Nature 289:607–609 (1981).
Santos et al., *Nature*, 298: 343–347 (1982).
Parada et al., *Nature*, 297: 474–478 (1982).
Chang et al., *Nature*, 297: 479–483 (1982).
Tabin et al., *Nature*, 300: 143–149 (1982).
Reddy et al., *Nature*, 300: 149–152 (1982).
Der et al., *Proc. Natl. Acad. Sci. USA*, 79: 3637–3640 (1982).
Dhar et al., *Science*, 217: 934–936 (1982).

* cited by examiner

*FIGURE 4A* *FIGURE 4C*
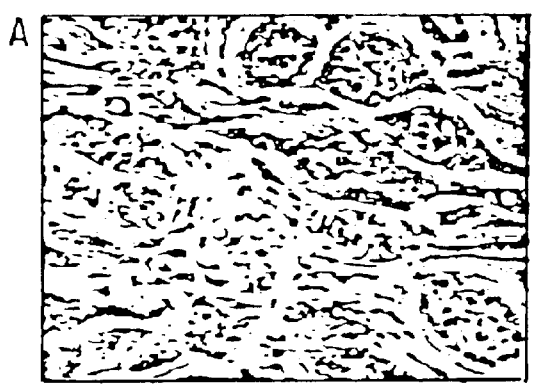 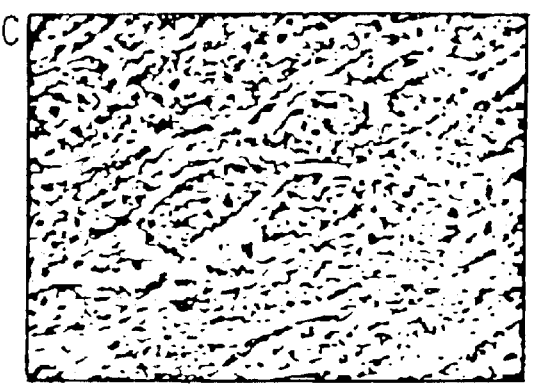
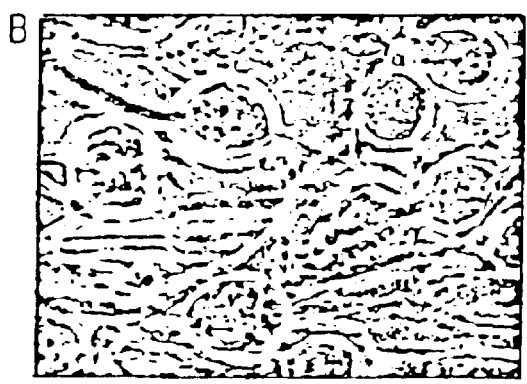 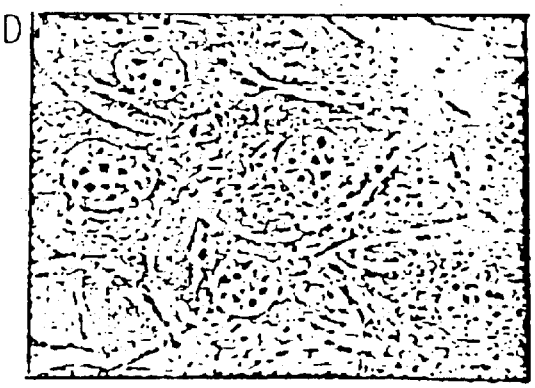
*FIGURE 4B* *FIGURE 4D*

FIGURE 11

ISOLATING A SEGMENT OF DNA OF WILD-TYPE ALLELE WHICH IS MUTATED TO PRODUCE A MUTANT ALLELE

CREATING AN ANTIGEN CAPABLE OF CAUSING, UPON IMMUNIZATION INTO A HOST, PRODUCTION OF ANTIBODIES REPRESENTATIVE OF THE DIFFERENCE IN DNA STRUCTURE RESPONSIBLE FOR THE DIFFERENCE IN FUNCTION BETWEEN THE WILD-TYPE ALLELE AND THE MUTANT ALLELE

IMMUNIZING A HOST UNDER CONDITIONS WHEREBY THE HOST PRODUCES SAID ANTIBODIES

FIGURE 14 normal

```
     glu gln arg ala ser pro val thr phe ile ile ala thr val   val   gly val    aa 666
     GAG CAG AGA GCC AGC CCG GTG ACA TTC ATC ATT GCA ACT GTA   GTG   GGC GTC
``` transforming
```
                                                              GAG
                                                              glu
```

```
     leu leu phe leu ile leu val val val gly ile leu ile lys arg arg    aa 683
     CTG CTG TTC CTG ATC TTA GTG GTC GTT GGA ATC CTA ATC AAA CGA AGG
```

FIGURE 15

A) ACGCCCACTACAGTTGCAAT   nucleotides 1999-2018, wild type sequences

B) ACGCCCTCTACAGTTGCAAT   nucleotides 999-2018, $T_{2012}$ to A

C) CCGTCCTCAGCTGTGACC     nucleotides 996-1013, control probe

D) ACGCCCCCTACAGTTGCAAT   nucleotides 1999-2018, $T_{2012}$ to G

FIGURE 16A
a b c d e f
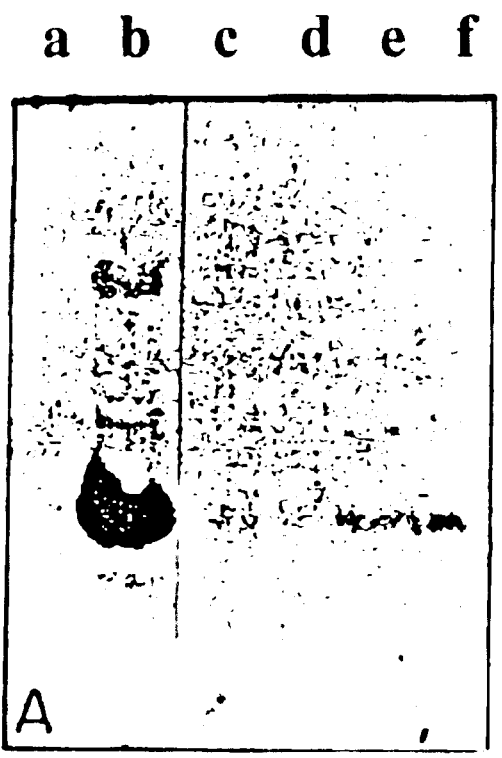
FIGURE 16B
a b c d e f
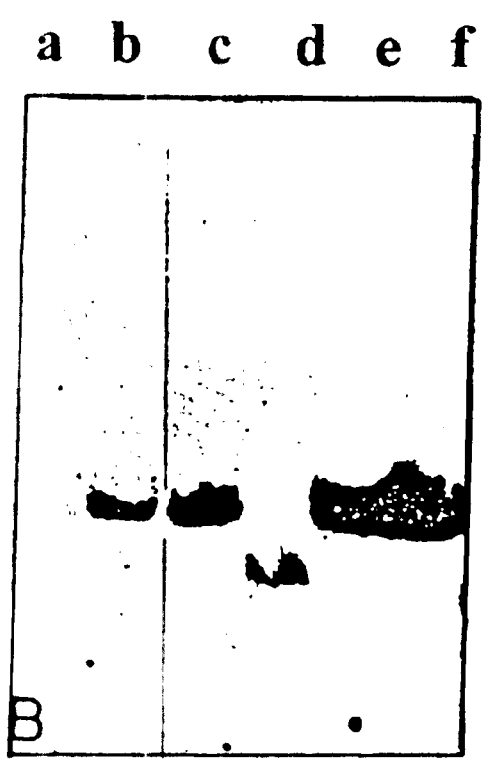
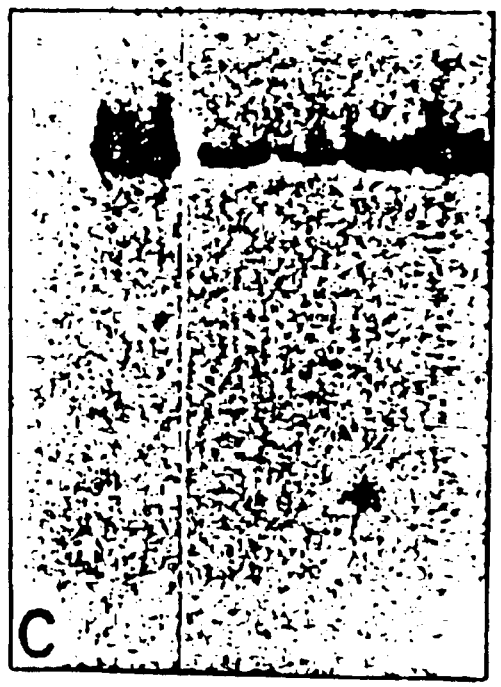
FIGURE 16C
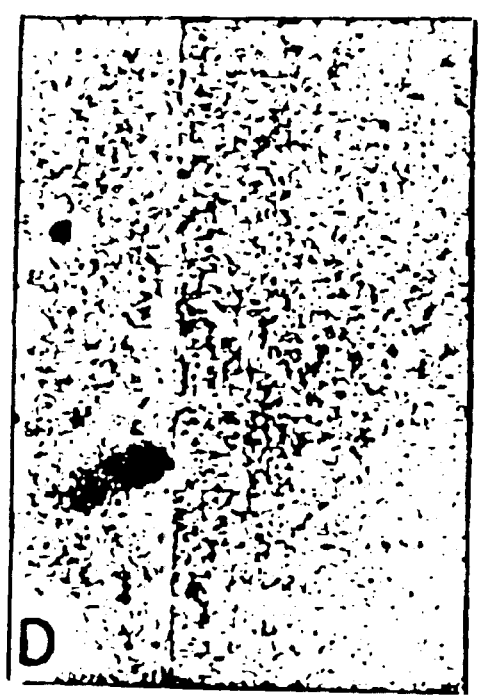
FIGURE 16D

FIGURE 18
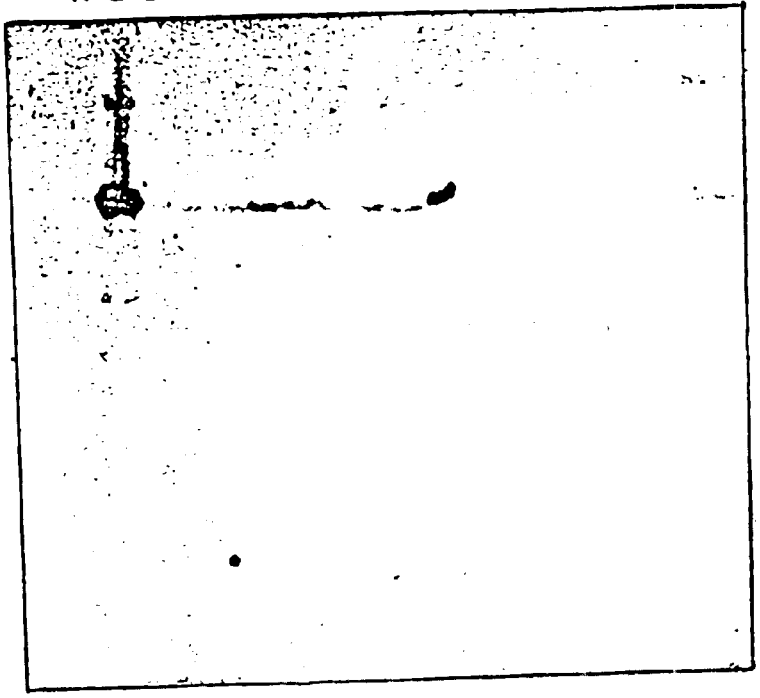
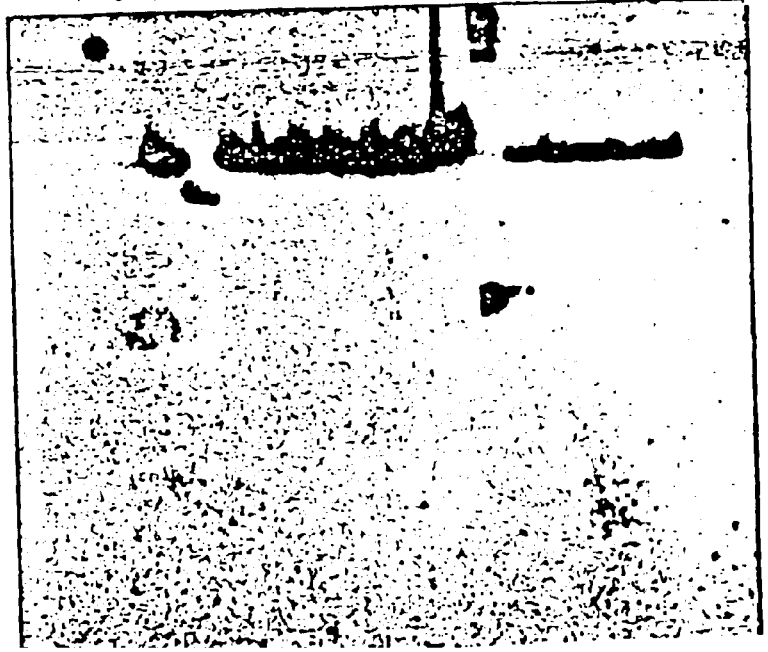

Construction of full length neu CDNA
Clone from ME180 and neu CDNAs

Construction of pMAX neu and pMAX delta neu

Neu Oncogene Probe Design:

ONCOGENES AND METHODS FOR THEIR DETECTION

This application is a continuation of U.S. Ser. No. 07/880,483, filed May 6, 1992, now abandoned, a continuation of U.S. Ser. No. 07/772,614, filed Oct. 8, 1991, now abandoned, continuation of U.S. Ser. No. 07/228,392, filed Aug. 4, 1988, now abandoned, a continuation-in-part of U.S. Ser. No. 06/828,599, filed Feb. 11, 1986, now abandoned, a continuation of U.S. Ser. No. 06/379,721, filed May 19, 1982, now abandoned; and U.S. Ser. No. 06/765,362, filed Aug. 13, 1985, now abandoned, a continuation-in-part of U.S. Ser. No. 06/432,337, filed Oct. 1, 1982, now U.S. Pat. No. 4,535,058; and U.S. Ser. No. 06/871,102, filed Jun. 4, 1986, now U.S. Pat. No. 4,935,341; and U.S. Ser. No. 07/182,501, filed Apr. 18, 1988, now abandoned, a continuation-in-part of U.S. Ser. No. 06/871,102, filed Jun. 4, 1986, now U.S. Pat. No. 4,935,341. The teachings of each of the above-referenced documents are incorporated herein by reference.

GOVERNMENT SUPPORT

The work described herein was supported by grants from the National Institutes of Health, the National Cancer Institute and the American Business Cancer Research Foundation.

TECHNICAL FIELD

This invention is in the field of molecular biology and more specifically relates to isolating discrete genes from mammalian DNA and to defining differences between mutant alleles and their corresponding wild type alleles, particularly oncogenes and proto-oncogenes, and to assays which take advantage of such differences.

BACKGROUND ART

Previous work relating to chemical carcinogenesis has demonstrated that carcinogenic potency of a compound often correlates with its mutagenic power. See McCann, J., Choi, E., Yamasaki, E. and Ames, B. N. Proc. Natl. Acad. Sci. USA 72: 5135–5139 (1975); McCann, J. and Ames, B. N. Proc. Natl. Acad. Sci. USA 73: 950–954 (1976); Bridges, B. A. Nature 261: 195–200 (1976); and, Bouck, N. and diMayorca, G. Nature 264: 722–727 (1976). This suggests that DNA is the ultimate target of carcinogenic activation. Because of this, researchers have attempted to identify and study DNA segments in tumor cells, often referred to as "oncogenes," whose alteration is critically important for oncogenic conversion.

The molecular basis of malignant transformation leading to cancer is poorly understood. It is generally thought that transformation begins with damage to DNA, although the exact nature of the damage is in dispute. Presumably, the alteration of critical genes, sometimes called oncogenes, which are carried in the DNA is an essential step in a conversion of a normal cell to one that is capable of causing cancer. Such oncogenes could be activated by carcinogens of various kinds known to cause cancer.

There has been a tremendous amount of research effort directed toward identifying, and presumably subsequently isolating, such oncogenes. Despite the amount of effort which has been undertaken, little is understood about activation and activity of oncogenes.

DISCLOSURE OF THE INVENTION

This invention relates to a method for isolating a discrete, transmissible gene from DNA of mammalian origin and to an investigation of the differences between oncogenes of mammalian origin and their corresponding proto-oncogenes. In particular, it relates to definition of differences between the EJ oncogene, previously shown to cause human bladder cancer, and its proto-oncogene and to assessment of cellular DNAs to determine whether they include lesions or alterations in a neu gene which result in activation of the proto-oncogene and conversion of the proto-oncogene to an oncogene. The procedures involved in defining the differences in these proto-oncogene/oncogene pairs can be used to define differences between any mutant allele and its corresponding wild type allele; the procedures are particularly useful in defining the differences between oncogenes and their corresponding proto-oncogenes.

Identifying and isolating oncogenes has many desirable consequences. The oncogene isolated can be compared with closely related sequences in normal DNA and such comparison should lead to an understanding of what alterations occur to lead to the creation of an active oncogene; in fact, such comparison has made it possible to demonstrate that a proto-oncogene can be converted to an oncogene by a single nucleotide alteration or point mutation. This has made it possible to produce oligonucleotide probes which are specific for nucleotide sequences of the region in which the activation mutation(s) resides. Such probes can be used to determine the presence or absence of an oncogene which differs from its proto-oncogene. Methods of detecting an oncogene using such probes are described herein. As described in detail in the following sections, investigation of the activity and characteristics of oncogenes and their corresponding proto-oncogenes entailed discovery of a method for isolating a discrete, transmissible gene of mammalian origin, initial assessment of the basis of functional differences between the two (oncogene and proto-oncogene) and subsequent determination of the means by which a proto-oncogene is converted or activated to its oncogene form.

Discovery of a Method for Isolating a Discrete, Transmissible Gene

As described in application Ser. No. 379,721, filed May 19, 1982, now abandoned, the concept of a discrete, definable oncogene has been directly demonstrated by molecular isolation of discrete transforming genes from the EJ human bladder carcinoma cell line. That such a discrete, definable oncogene exists was demonstrated using a method described in the co-pending application.

In the method described, mammalian DNA from a donor is fragmented into a multiplicity of fragments, at least one of which contains a discrete, transmissible gene of interest. A "marker" is provided on the fragment containing the gene of interest, if such a marker is not already present. The multiplicity of fragments are then transmitted into recipient cells which are capable of phenotypically expressing the presence of the discrete transmissible gene, i.e., the phenotype of the gene can be scored by cells carried in culture. These recipient cells are then cultured under conditions which allow phenotypic expression by the gene of interest, and cells showing such phenotypic expression are selected. Because of the phenotypic expression, the selected recipient cells are known to contain the gene of interest; they may also contain additional DNA sequences on the donor fragment transmitted into the recipient cells, as well as their own endogenous DNA. The selected recipient cells' DNA is then recovered and used in the aforementioned series of steps in place of the original donor DNA. These steps are repeated until the recipient cells selected in the last step have acquired essentially only the discrete, transmissible, mammalian gene and its associated marker. At this point, the discrete, transmissible gene is recovered from the cells selected employing its associated marker.

In one embodiment of this invention which has actually been experimentally performed, an oncogene for human bladder cancer has been isolated from DNA obtained from a human bladder cancer cell line. The original DNA was serially passed by transfection into mouse fibroblast cells using the above method until a mouse fibroblast cell containing essentially only the human bladder cancer oncogene and a marker was selected. In this case, the marker was an Alu DNA sequence which is repeated about 300,000 times in a human DNA molecule but is not present in mouse fibroblast cells. The interspecies transfection thus resulted in the ultimate selection of a cell containing the oncogene of interest and its associated marker. All of the DNA from the transfected cell was employed in the creation of a genomic library in a lambdaphage and the appropriate chimeric lambdaphage was then selected using a probe specific for the human Alu marker.

A sub-cloned insert of 6.6 kb which carried transforming activity was amplified in the plasmid vector pBR322. The sub-cloned oncogene has been used as a sequence probe in Southern blot analyses. The oncogene appears to derive from sequences present in normal cellular DNA. Structural analysis has so far failed to reveal differences between the oncogene and its normal cellular homolog. The oncogene is unrelated to transforming sequences detected in a variety of other types of human cell lines of colonic, lung, and neuroblastoma origin. In contrast, the human bladder oncogene isolated from one cell line appears closely related to oncogenes active in other human bladder carcinoma cell lines.

Assessment of the Basis of Functional Differences Between Oncogenes and Their Corresponding Proto-oncogenes Initially, experiments were performed to determine whether the dramatic functional difference between the EJ oncogene and its proto-oncogene were due to a regulation mechanism or to one of sequence differences. These experiments provide data indicating that upregulation of this gene was not responsible for cellular transformation. Thus, it was concluded that the dramatic functional differences must be due to changes in the DNA sequence of said genes.

Determination of the Means by Which a Proto-oncogene is Converted to its Oncogenic Form Subsequent to the determination that functional differences between an oncogene and it corresponding proto-oncogene must be due to differences in the DNA sequences of the two gene types, assessment of the two demonstrated what that difference is: a single base substitution, or point mutation, in the nucleotide sequence of the proto-oncogene, which resulted in its activation or conversion to an oncogene, which was accompanied by a difference in the amino acid sequence of the encoded protein.

In the case of the EJ oncogene and its corresponding proto-oncogene, the area of the 6.6 kb pEJ responsible for cellular transformation in NIH3T3 fibroblasts was narrowed to a 350 kb segment by a series of in vitro recombinations. This 350 kb segment was then sequenced for the oncogene and proto-oncogene, and it was found that single base substitutions accounted for the difference at the 60th nucleotide from the XmaI restriction site. This substitution in the codon for glycine ($Gly^{12}$), normally occurring as GGC, was changed to the sequence GTC, which codon expresses valine. Thus, the specific difference in cellular DNA from the EJ and its proto-oncogene was located, and the difference in the amino acid sequence of the corresponding p21 proteins was also determined.

Assays for detecting such changes in DNA sequences were then developed. In one type of assay, restriction enzymes specific for a site on either the oncogene or the proto-oncogen, but not both, were employed to detect differences in such DNA sequences. In another type of assay, polynucleotide probes specific for a nucleotide site on either the oncogene or the proto-oncogene, but not both, are employed to detect differences in such DNA sequences or in RNA transcribed from such DNA sequences.

Since the p21 proteins encoded by these genes are also different, serological reagents, such as polyclonal or monoclonal antibodies, can also be developed which are specific for the altered or normal sequence domains in p21 proteins, or for an amino acid sequence not involved in the alteration which occurs during carcinogenesis. Such serological reagents can then be employed in various protocol to provide a very sensitive test for human bladder carcinogenesis. Similarly, these assays could be employed to detect changes in other wild type alleles causing mutant alleles.

In the case of the neu proto-oncogene, it was determined that conversion into an oncogene also occurs as a result of a single nucleotide alteration, or a point mutation. This point mutation was initially seen in a rat neuroblastoma induced by transplacental expsoure to a carcinogen (e.g., ethylnitrosourea) and found to affect the amino acid sequence of the transmembrane region of the p185 encoded by the DNA. That is, a valine present in the normal protein is replaced by a glutamic acid residue.

Oligonucleotide probes used to assay for similar point mutations suspected to be present in seven additional neu oncogenes, each of which arose in a separate, independently induced tumor, demonstrated the presence of the same activating mutations in all seven neu oncogenes. The same amino acid substitution (glutamic acid replacing valine) resulted in these cells. Further assays with oligonucleotide probes homologous to the neu gene demonstrates that the mutagen methylnitrosourea induces formation of nervous system tumors and activation of neu genes at the same position as shown to occur in the ethylnitrosurea-induced tumors.

The human homolog of the neu gene (also known as c-erbB2 or HER2) is thought to achieve an oncogenic state through the action of a similar mechanism: alteration of a single nucleotide in the normal cellular DNA sequence (the proto-oncogene), resulting in activation of the oncogene. The activating lesion found can be identified in the DNA of a variety of spontaneously arising human tumors through the use of oligonucleotide probes constructed to be specifically reactive with the region of the human neu gene corresponding to the region in the rat neu oncogene known to contain the activating mutations. Identification in human tumor cells of the activating point mutation responsible for conversion of the proto-oncogene into the neu oncogene can serve as the basis for construction of oligonucleotide hybridization probes useful in testing human tumor DNAs for the presence or absence of point mutations responsible for activation of neu oncogenes. These hybridization probes can be used in detecting the occurrence of the neu proto-oncogene and of the neu oncogene in cells and in determining the profile of oncogene activations in human tumor specimens. Such oligonucleotide probes are described, as are methods for their use in detecting the presence or absence of neu oncogenes in tumor cells. Antibodies specific for the p185 protein encoded by the neu oncogene, which can be used to detect the occurrence of the neu oncogene, are also described.

The protein coded for by the oncogene can be produced in significant quantities so that it can be studied to understand the metabolic alterations that occur in the cell during tumorigenesis. This may also lead to insights into methods by which one could antagonize or inhibit its functioning. In addition, it is expected to lead to sensitive tests for the presence of this protein which will be useful in the early detection of the onset of cancer.

BRIEF DESCRIPTION OF THE FIGURES

FIGS. 4A–4D are photographs taken through a phase-contrast microscope at 500x magnification of four cell lines transfected with pEJ or pEC.

FIGS. 10 and 11 are block diagrams illustrating assay protocols employing endonucleases or antisera against protein coded for by normal genes or transforming genes.

FIG. 14 shows nucleotides 1968 to 2073 and the predicted amino acid sequence for the normal rat neu gene and the transforming rat neu gene.

FIG. 15 shows the nucleotide sequence of oligonucleotide probes corresponding in sequence to a) the wild type (normal), b) the mutant neu version of the neu gene, c) DNA from DHFR G8, and d) a modified version of the mutant neu gene in which there is a T to G transversion.

FIG. 16 shows electrophoretic gel patterns after hybridization of DNA from neu transfectants with oligonucleotide probes.

FIG. 18 shows electrophoretic gel patterns after probing of fourteen transfectants containing ten independent activated neu genes with either the oligonucleotide corresponding to the normal gene (proto-oncogene) (top) or the oligonucleotide corresponding to the transforming gene (oncogene) (bottom).

DETAILED DESCRIPTION OF THE INVENTION

Figure 1:
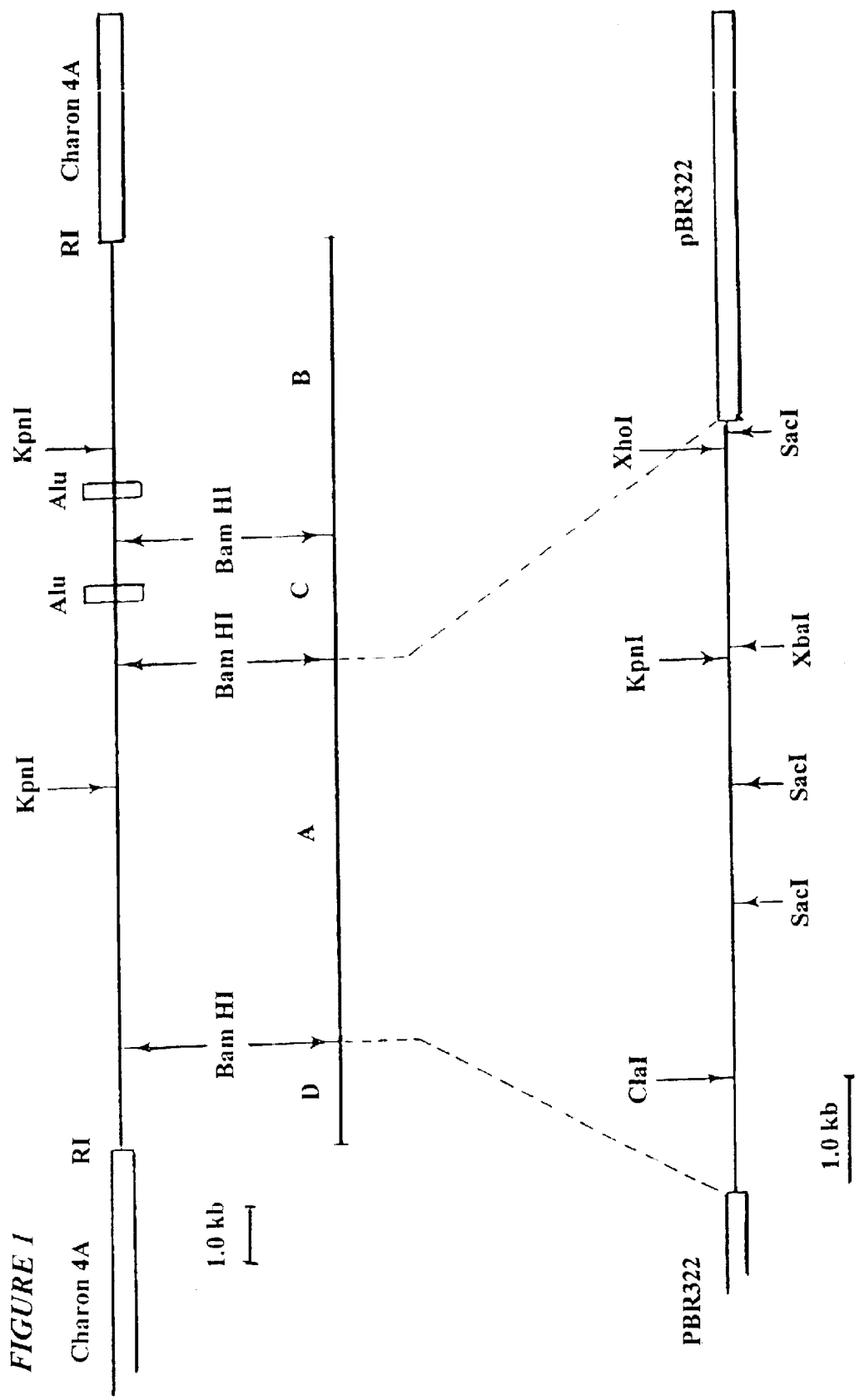
FIG. 1 is an endonuclease cleavage map of a transforming DNA segment isolated from EJ human bladder carcinoma DNA.

The present invention is based on the determination that conversion of a proto-oncogene to an oncogene can occur as a result of an alteration or difference in the nucleotide sequence of the proto-oncogene. That is, in DNA of mammalian origin, alteration of a single nucleotide (a point mutation) in the DNA sequence of a proto-oncogene has been shown to result in activation of the proto-oncogene to an oncogene. It has been shown that cellular genes or proto-oncogenes (the nucleotide sequence present in the genome of normal non-tumor cells) can undergo mutation into their corresponding oncogenes (the nucleotide sequence whose expression within a cell causes its conversion from a normal cell into a tumor cell) by a single nucleotide substitution.

In particular, it has been shown that ras genes and neu genes can be converted to respective oncogenes by a single nucleotide substitution. Demonstration that conversion occurs in this manner is described in detail in the sections which follow and in co-pending U.S. applications Ser. No. 828,599 (filed Feb. 11, 1986) and Ser. No. 871,102 (filed Jun. 4, 1986); the teachings of both applications are incorporated herein by reference.

As a result of the present invention, it is now possible to identify and isolate from mammalian cells any discrete, transmissible gene or DNA sequence which undergoes activation from proto-oncogene to oncogene in a similar manner (i.e., by means of an alteration in the nucleotide sequence which is a single nucleotide change which results in conversion of the proto-oncogene to its oncogenic form). Also as a result of the present invention, it is possible to produce oligonucleotide probes which can distinguish between the oncogene and the corresponding proto-oncogene. Such a probe, which can be used to distinguish the neu oncogene from its proto-oncogene, has been produced, as described herein.

Isolation and Characterization of the Human Bladder Cancer Oncogene

The experimental work presented below resulted in isolation of the human bladder cancer oncogene. However, any discrete, transmissible gene from mammalian DNA could be isolated using the techniques of this invention. A "discrete" gene is one having a consecutive sequence of base pairs located in one block of sequences of definable length. This block may contain regions encoding protein as well as intervening sequence regions which do not code protein. A "transmissible" gene is one which can be transmitted into cells grown in cell culture.

DNA containing such a discrete, transmissible gene can be isolated from its host cells by art recognized techniques. For example, cells grown in culture can be lysed and the viscous lysate can then be extracted with phenol and with chloroform-isoamyl alcohol. DNA can then be precipitated by ethanol precipitation.

The initial DNA containing the gene of interest can be fragmented by mechanical or enzymatic methods. For example, it can be passed through a narrow gauged needle so that it will be fragmented due to shear. On the other hand, DNA molecules might also be fragmented using restriction endonucleases. The important limitation on the fragmentation is that at least one fragment results each time the fragmenting is done which contains all of the gene of interest intact.

If the fragment containing the gene of interest does not have an associated marker sequence, one must be added. It is possible to establish experimentally a linkage between a gene and a marker. For example, fragmented cell DNA of a donor cell may be tagged with copies of cloned DNA sequence, such as a ØX174 DNA fragment. Upon co-transfection, the donor cell DNA fragments and the cloned "tag" DNA fragments become linked in the recipient cell in a randomly alternating co-polymer. See Lowy, I., Pellicer, A., Jackson, J. F., Sim, G. K., Silverstein, S. and Axel, R., *Cell* 22, pp. 817–823 (1980).

In a preferred embodiment, the fragment containing the gene of interest will also contain a species specific marker. For example, human DNA contains over 300,000 copies of the Alu sequence interspersed throughout the entire genome. Thus, almost every gene is linked closely, i.e., less than 10 kilobases, to a copy of this repeated sequence. See Houck, C. M., Rinehart, F. D., and. Schmid, C. W.,*J. Mol. Biol.* 132, pp. 289–306 (1979).

Since this Alu sequence is not present in mouse DNA, it is species specific to human DNA. In fact, a molecular clone of the human Alu sequence as probe in Southern blots has been used to detect the presence in mouse cells of introduced human oncogenes of bladder and colon carcinoma origin and of promyelocytic leukemia origin. See Murray, M. J., Shilo, B. Z., Shih, C., Cowing, D., Hsu, H. W. and Weinberg, R. A., "Three different human tumor cell lines contain different oncogenes," *Cell* 25, pp. 355–361 (1981). Each of these, when resolved from the mouse sequence background, was determined to be affiliated with its own characteristic array of human Alu blocks.

The DNA fragment containing the gene of interest and marker is transmitted into cells capable of phenotypically expressing the presence of the gene of interest. Any method of transmission of the DNA fragments into such cells can be employed. For example, microinjection techniques could be used.

The preferred transmission technique is transfection. DNAs of any sequence or biological origin can be introduced into mammalian cells by transfection. For example, the DNA of a bacteriophage can be transfected with an efficiency comparable to that of the DNA carrying a mammalian globin gene. Thus, the transfected DNA need not have any sequence homology with the genome of the recipient cell.

Any standard method of transfection is suitable. One method involves the addition of DEAE-dextran to increase the uptake of naked DNA molecules by a recipient cell. See McCutchin, J. H. and Pagano, J. S.,*J. Natl. Cancer Inst.*, 41, pp. 351–7 (1968). Another technique is the calcium phosphate precipitation technique which depends upon the addition of $Ca^{++}$ to a phosphate-containing DNA solution. The resulting precipitate apparently includes DNA in association with calcium phosphate crystals. These crystals settle onto a cell monolayer. The resulting apposition of crystals and cell surface appears to lead to uptake of the DNA. A small proportion of the DNA taken up becomes expressed in a transfectant, as well as in its clonal descendants. See Graham, F. L. and van der Eb, A. J., *Virology* 52, pp. 456–467 (1973) and Graham, F. L. and van der Eb, A. J., *Virology* 54, pp. 536–539 (1973).

The cells into which the DNA fragments are transmitted must be capable of phenotypically expressing the presence of the gene. One phenotype which can easily be scored in transfections is that of transformation, seen either as focal overgrowth of monolayers or colony growth in soft agar. Although the mechanism of transformation is poorly understood, foci induced by transfection with a gene causing transformation is readily scoreable as colonies of cells resulting from transfection with the gene of interest.

It is particularly preferred, when attempting to isolate a human gene, to transmit the DNA fragments containing the gene of interest into mouse cells. Mouse cells are capable of being transformed by DNA preparations containing oncogenes and they do not contain human markers such as the Alu sequence. More particularly, it has previously been shown that DNA from the EJ human bladder carcinoma cell line is capable of inducing transformation of mouse fibroblast cells. See Krontiris, T. G. and Cooper, G. M., "Transforming activity of human tumor DNA," *Proc. Natl. Acad. Sci., USA* 78, pp. 1181–84 (1981) and Shih, C., Padhy, L. C., Murray, M. and Weinberg, R. A., "Transforming genes of carcinomas and neuroblastomas introduced into mouse fibroblasts," *Nature* 290, pp. 261–4 (1981).

The 3T3 cells used as recipients for the transfected human carcinoma oncogenes are an unusual cell line which take up and allow efficient, stable expression of transfected DNAs. Another suitable cell line, in this regard, is known as Rat-1 cell line. Most cell lines, however, are relatively refractory to transfected DNAs. Despite this, it is believed that other cell lines will be found which allow phenotypic expressions of transfected genes. Additionally, it is believed that novel techniques for introducing DNAs into a larger range of cells will also be developed.

After the cells have taken up the DNA fragments, they are cultured under conditions which allow phenotypic expression to occur. If any special conditions are required, such as a specific temperature, the presence of a selective medium, etc., the cells are cultured under such conditions.

After phenotypic expression has occurred, one or more of the cells showing such expression are selected. For example, a colony expressing the phenotype (e.g., transformation) can be physically picked by standard techniques and the cells of the chosen colony can then be used to seed a large scale culture.

The DNA from the original mammalian donor cell is recovered from the recipient cells which have expressed the phenotype encoded by the donor DNA. This can be done by lysing the cell and extracting and precipitating the recipient cells' DNA using the techniques mentioned above. Of course, such recipient cells will typically also contain their own endogenous DNA.

Recovered DNA is then employed in place of the original mammalian donor DNA and the steps described above are repeated, as required. By repeating all of these steps, serial transmission of the gene of interest, together with its marker, is accomplished. When transfection techniques of human oncogenes into mouse fibroblast cells are done, it has been found that two transfections are usually sufficient in order to provide a recipient cell having the gene of interest as well as its associated marker, but lacking virtually all other extraneous human DNA. Although there may be small fragments of donor DNA in addition, such small fractions should not impede expression by the gene of interest.

Although the experimental work discloses an interspecies transfection of human DNA into mouse fibroblast cells, other interspecies transfections have also been shown to be possible. For example, rabbit bladder carcinoma genes are able to transform recipient mouse fibroblast cells.

When a cell has been selected which contains essentially only the gene of interest and its associated marker, the marker is employed to recover the gene. For example, in a secondary transfectant of a mouse fibroblast cell transfected with a human bladder cancer oncogene, recovery of the gene can be done by creating a genomic library. The gene of interest, or a portion of it, may be contained within a phage also carrying a human repeated gene sequence. Since molecular clones of this human repeated gene sequence can be prepared, the phage may be identified with standard hybridization procedures. Genomic libraries in lambdaphage can be created by art recognized techniques. See Blattner, F. R. et al., Science, 196, pp. 161–169 (1977). Subsequently, the lambdaphage containing the gene of interest can be identified by its associated marker. For example, in a case where the marker is an Alu sequence, cloned DNA for Alu can be used as the probe. For example, in the examples set forth below, that fraction of human DNA which self-anneals at a rate of Cot=1 or less was employed as probe. This probe was prepared from total cellular DNA obtained from a human bladder carcinoma cell line A1663, but any human DNA might serve for making this probe. Functional equivalents to the Cot=1 probe actually employed in the examples set forth below are: (1) whole, unfractionated human DNA; and (2) a molecular clone of one highly repeated human Alu sequence, such as the BLUR8 clone. See Jelinek, W. R., et al., Proc. Natl. Acad Sci. U.S.A. 77:1398–1402 (1980).

In the case of the human bladder cancer oncogene, it has been determined that the protein coded for by this gene has a molecular weight of about 21,000 daltons. This is known because of a series of experiments which indicated that the human bladder carcinoma (EJ) oncogene is homologous to the Harvey sarcoma virus oncogene (ras). Structural analysis indicated that the region of homology was a 3.0-kilobase SacI fragment of the EJ oncogene. Both EJ and ras DNA probes detect similar transcripts in transfectants derived from bladder carcinoma cell lines. The ras genes encode proteins of molecular weight 21,000. See Shih, T. U. et al., Virology, 96:64–79 (1979). Immunoprecipitation of metabolically labelled lysate of transfected cells has detected a protein of this size.

Once isolated, the mammalian gene can be cloned into a suitable recombinant DNA vector. Such cloning employs fundamental gene splicing techniques, such as those described by Cohen and Boyer in U.S. Pat. No. 4,227,224.

Although the human bladder cancer oncogene was cloned into the bacteria plasmid pBR322 in the specific work described herein, other recombinant DNA vectors, such as phages, animal viruses and yeast vectors could be employed. In such techniques, hosts would be employed which allow the recombinant DNA vector to multiply.

To determine whether the significant difference between the oncogene and proto-oncogene was one of regulation, a comparison of the expression of the c-Ha-ras proto-oncogene (EC) from a normal human bladder epithelial cell line with the expression of the oncogene in the EJ transformed bladder cell was undertaken. The bladder epithelial cells employed, Hbl-5, were a primary tissue culture explant from a five-month old human bladder grown on inactivated NIH3T3 feeder layers. This culture was grown out from fresh human bladder tissue and was shown to exhibit several of the properties expected of transitional bladder epithelium. It was free of underlying stromal material, and consequently represented a close counterpart of the cells from which the bladder carcinoma originated.

Total cellular RNA was prepared from both normal and transformed bladder cells. Transcripts were analyzed by running the RNA on a formaldehyde gel, transferring it to a nitrocellulose filter, and probing the filter with nick-translated, EJ oncogene clone.

Figure 2A:
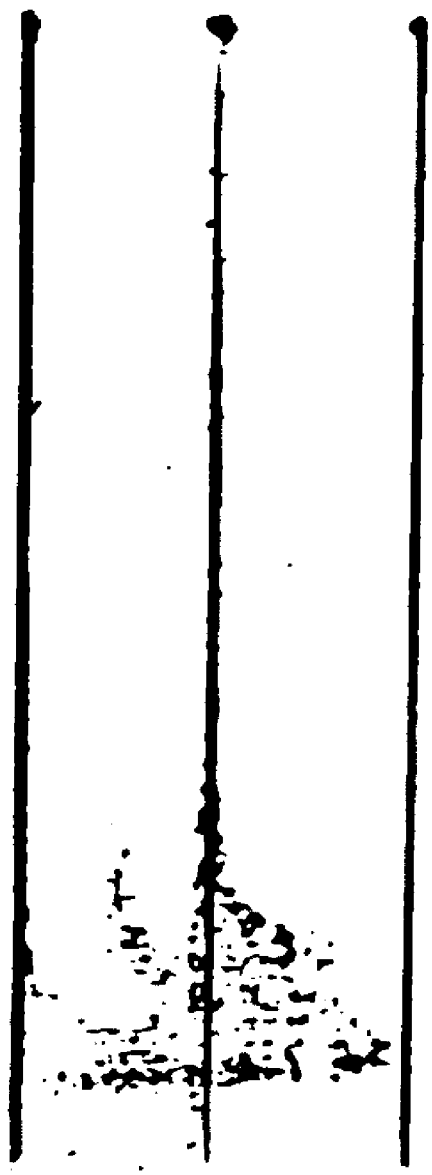
FIG. 2A presents electrophoretic gel patterns of total cellular RNA obtained from both normal and transformed bladder cells, which patterns were visualized by autoradiography.

The specific procedures employed were as follows. Total polyadenylated RNA was prepared by the technique of Varmus et al. See Varmus, H. E. et al., Cell, 25:23–36 (1981). Four micrograms of RNA was then fractionated by electrophoresis through formaldehyde-containing 2 percent agarose gels and transferred to nitrocellulose. A ras-specific probe was prepared by cutting pEJ with BamHI, fractionating the resulting fragments through a 1 percent agarose gel and extracting the 6.6 kb insert with NaI and glass beads. The nick-translated fragment ($6.6 \times 10^7$ cpm micrograms$^{-1}$) was annealed to the immobilized RNA. See Rigby, P. W. et al. J. Mol. Biol. 13: 237–251 (1977); and, Wahl, G. M. et al., Proc. Natl. Acad. Sci. USA, 76:3683–3687 (1979). Bands homologous to the probe were visualized by autoradiography. Molecular weights were determined by comparison with markers obtained from in vitro run-off transcription of the adenovirus late promoter. See Manley, J. L. et al. Proc. Natl. Acad. Sci. USA 77: 3855–3859 (1980). FIG. 2A shows the relative levels of c-Ha-ras specific RNA in the two cell types: Lane 1, RNA from EJ cells; Lane 2, RNA from Hbl-5 cells. As can be seen, similar levels of RNA were detected in the two cultures and the transcripts had a size of 1.2 kb.

The only known products of the ras genes are proteins of approximately 21,000 daltons mass, referred to as p21. Experiments were conducted to analyze mobility rates of p21 protein lysates from both EJ and normal bladder cells. Monoclonal antisera against the v-Ha-ras p21 protein were employed. See Furth, M. E. et al., J. Virol., 43: 294–304 (1982). Control experiments assured that the amounts of antibody used were in excess of that required to immunoprecipitate the antigen present. The results are shown in FIG. 2B.

Specifically, cultures were labelled with $^{35}$S-methionine for 12 hours. Lysates were then prepared and immunoprecipitated with non-immune sera (Lanes 1a and 2a), a monoclonal antisera (Y13-238) which precipitates the p21 encoded by Ha-MuSV but not the p21 encoded by Ki-MuSV (Lanes 1b and 2b) or a monoclonal antisera (Y13-259) which detects both the Ha-MuSV and Ki-MuSV p21's (Lane 1c and 2c). See Shih, T. Y. et al., *Virology*, 96:64–79 (1979). $20 \times 10^6$ cpm of lysate per sample was resolved by electrophoresis through a 12.5 percent SDS-polyacrylamide gel.

Figure 2B:
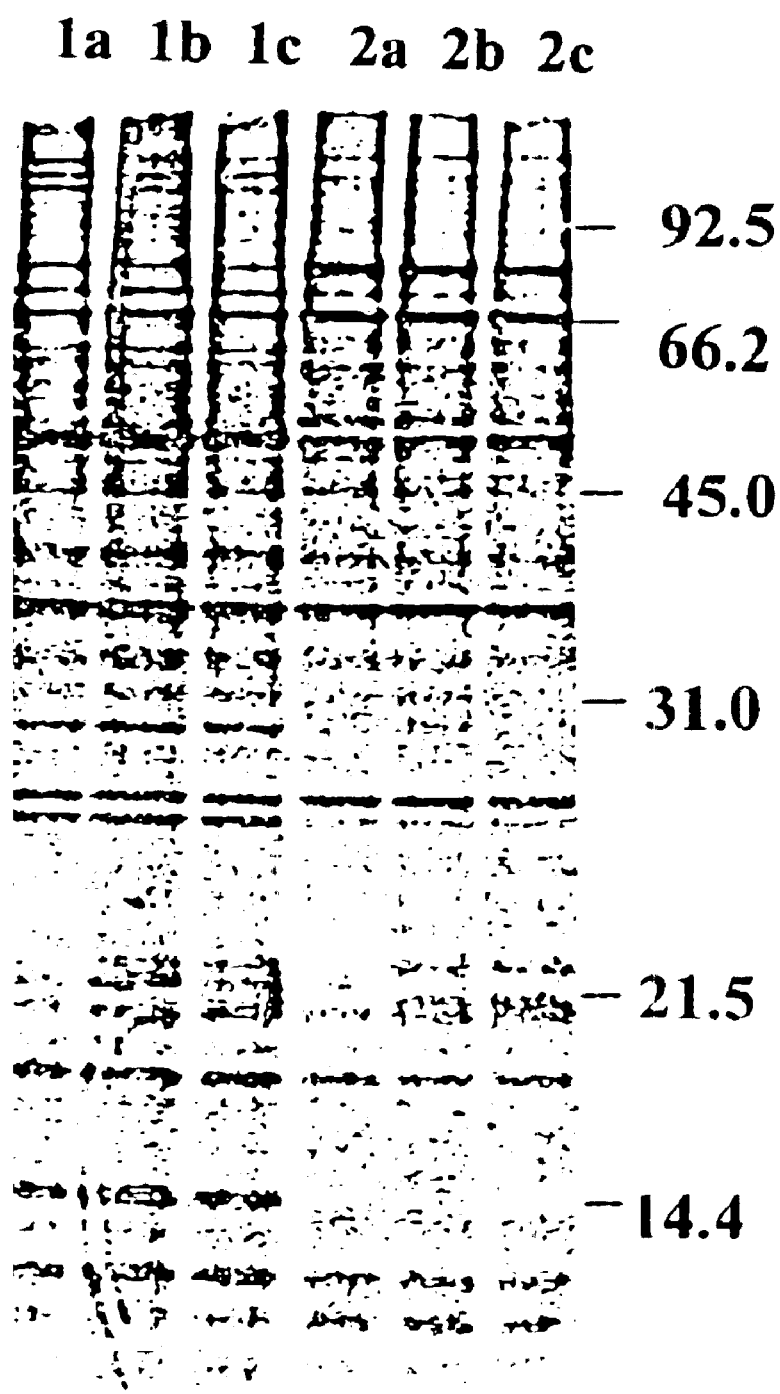
FIG. 2B presents electrophoretic gel patterns obtained by precipitation of metabolically labelled protein lysates from both EJ and normal bladder cells employing monoclonal antisera against the v-Ha-ras p21 protein.

FIG. 2B shows a comparison of p21 proteins immunoprecipitated from cell lysates of EJ cell clones (Lanes 1, a–c) and Hbl-5 cells (Lanes 2, a–c). These data indicate that at least two bands of radiolabelled protein were specifically precipitated by the anti-p21 sera from normal bladder cells. Detailed examination of the protein pattern of the bladder carcinoma seen revealed a complex array of bands: two pairs of closely spaced doublets. After comparing the intensities of the p21 bands to intensities of non-specifically precipitated background bands, it became apparent that the p21 proteins of the normal and the tumor cells were present in comparable amounts.

The above data indicate that increased levels of transcription were not responsible for the novel activity exhibited by the EJ oncogene. This conclusion rests in part on the fact that under the conditions of hybridization employed, the oncogene-probe reacted exclusively with transcripts of the human c-Ha-ras gene. Interpretation of the protein data was less clear, but it was apparent that both cells had comparable levels of proteins that were reactive with the Harvey-specific serum, and that these proteins could collectively be termed "p21."

It remained possible that the bladder epithelial cells were not representative of normal precursors of bladder carcinoma cells. Such a possibility might cloud interpretation since a ras gene could be expressed at a high level in one cell type without inducing transformation, and only achieve this phenotype when inappropriately expressed in a second cell type. Therefore, the levels of transcription and translation of the two genes in the same cellular background were measured.

Molecular clones of both genes were introduced into NIH3T3 cells. Colonies acquiring the EJ oncogene could be readily identified by their transformed morphology. However, cells acquiring clones of normal allele were not identifiable by any obvious change in behavior.

Because of this, a clone of the dominant selectable Ecogpt gene was cotransfected into NIH3T3 cells together with a 10-fold excess of either the cloned EJ oncogene or the cloned proto-oncogene (pEC). Specifically, transfections were carried out employing 75 micrograms NIH3T3 carrier DNA, 500 ng pEJ or pEC DNA, and 50 ng pSVZgpt DNA per $2 \times 10^6$ cells by known techniques. See Graham, F. L. and van der Eb, A. J. *Virology* 52: 456–471 (1973); and, Andersson, P. et al., *Cell*, 16:63–75 (1979). In each case, colonies were selected for the resistance to mycophenolic acid imparted by the acquired Ecogpt gene. See Mulligan, R. and Berg, P. *Proc. Natl. Acad. Sci. USA*, 78:2072–2076 (1981).

This strategy was employed since the introduction of a non-selected segment could be ensured by cotransfection with a selectable gene. See Wigler, M. et al. *Cell*, 16:777–785.(1979). In this instance, 75 percent of the mycophenolic acid-resistant colonies deriving from cotransfection of Ecogpt and pEJ were seen to be morphologically transformed; as expected, none of the colonies emerging after cotransfection with pEC was transformed.

Figures 3A, 3B, 3C:
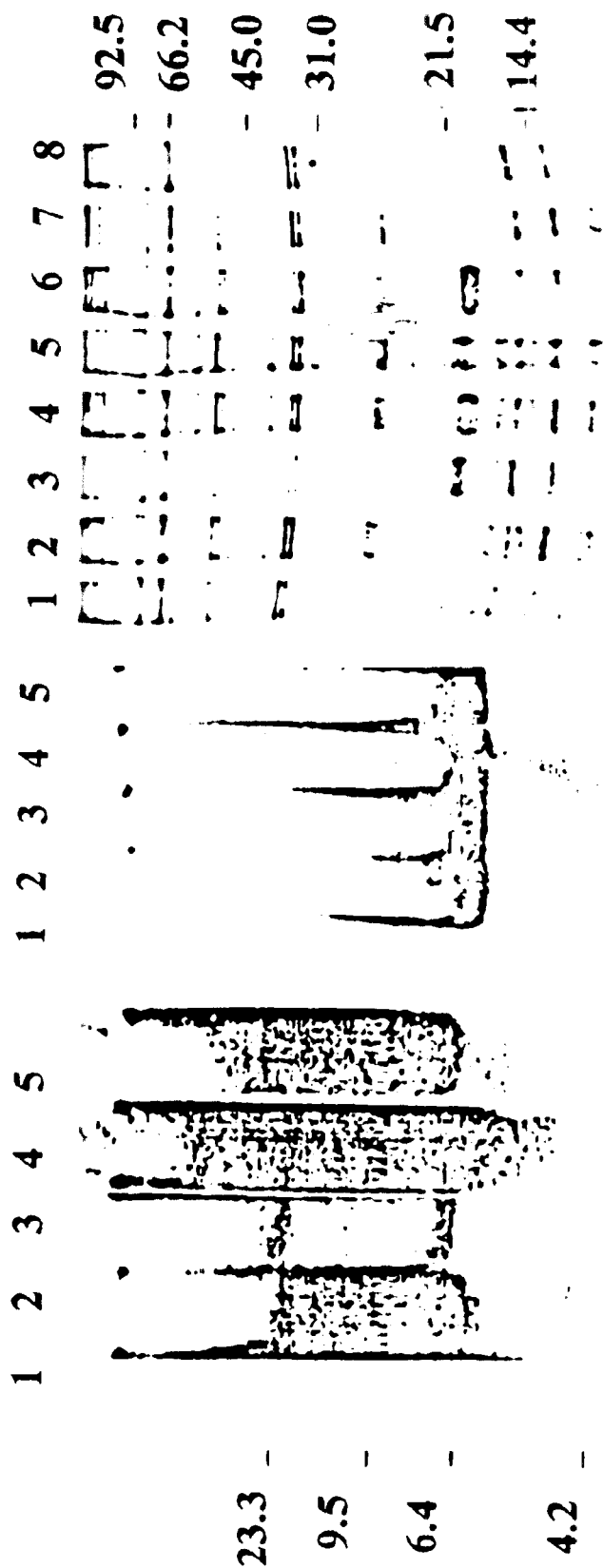
FIG. 3A presents electrophoretic gel patterns of cellular DNA from four cell lines transfected with pEJ or pEC.
FIG. 3B presents electrophoretic gel patterns of total polyadenylated RNA from the same four transfected cell lines.
FIG. 3C presents electrophoretic gel patterns of p21 protein immunoprecipitated from cell lysates of the same four transfected cell lines.

Cellular DNA of both classes of colonies was analyzed for the presence of pEC or pEJ sequences. Ten micrograms of each DNA was digested with endonuclease BamHI, which would be expected to liberate a 6.6 kb fragment from each intact copy of the cloned oncogene or proto-oncogene. The digested DNA was fractionated through a 1 percent agarose gel and transferred to nitrocellulose paper. $5 \times 10^6$ cpm of a ras-specific probe, as described above, was incubated with filter-bound DNA. The results are shown in FIG. 3A wherein the lanes are: Lane 1, NIH3T3 DNA; Lanes 2 and 3, DNA from cell lines transfected with pEJ: EJ/Gpt-2 (2) and EJ/Gpt-3 (3); Lanes 4 and 5, DNA from cell lines transfected with pEC: EC/Gpt-1 (4) and EC/Gpt-5 (5).

The normal mouse homologue of the ras gene hybridizes only weakly to the pEJ probe. See Parada, L. F. et al., *Nature*, 297:474–479 (1982). Consequently, its presence did not obscure the results. To ensure the transfected pBR322 sequences would not interfere with interpretation under data, the ras-specific sequences were prepared from pEJ and used as a probe. Seventy-five percent of the non-transformed colonies transfected with the proto-oncogene and all of the transformed oncogene-transfected colonies showed the presence of pEJ-homologous sequences migrating at 6.6 kb.

The positive colonies also had BamHI fragments of other sizes annealing to the probe. These represent copies of the clones that were broken during the transfection process.

Two cell lines containing intact copies of the oncogene and two lines containing an approximately equal of intact copies of the proto-oncogene were selected for further analysis. Photographs of these cell lines taken with a phase-contrast microscope at 500× magnification are shown in FIG. 4. Cell lines transfected with pEJ are shown at confluence (EJ/Gpt-2, photograph 4A) and subconfluence (EJ/Gpt-3, photograph 4B). Cell lines transfected with pEC are also shown at confluence (EC/Gpt-5, photograph 4C) and subconfluence (EC/Gpt-1, photograph 4D).

Total cellular RNA was prepared from all four transfected cell lines. The RNA preparations were then run on a formaldehyde gel, transferred to nitrocellulose filters, and probed with ras-specific DNA. The procedures previously described were employed and the results are shown in FIG. 3B wherein the lanes are: Lane 1, RNA from NIH3T3 cells; Lane 2, EJ/Gpt-2 cells; Lane 3, EJ/Gpt-3 cells; Lane 4, EC/Gpt-1 cells; Lane 5, EC/Gpt-5 cells.

The levels of p21 in these cells was also examined. Cell lysates were prepared, immuno-precipitated and analyzed as previously described. The results are illustrated in FIG. 3C as: immunoprecipitations with non-immune serum (Lanes 1, 2, 7, 8) or the monoclonal antiserum (Y13-238) which precipitates the Ha-MuSV p21 (Lanes 3–6). Cell lysates were prepared from EJ/Gpt-2 (Lanes 1, 3); EC/Gpt-1 (Lanes 2, 4); EJ/Gpt-3 (Lanes 5, 7) and EC/Gpt-5 (Lanes 6, 8). As can be seen, monoclonal serum against p21 precipitated similar amounts of p21 protein in pEC and pEJ transfected cells.

These data do not completely address the question of whether the two cloned genes are transcribed at the same rates in the cells, since it remained formally possible that a few of the acquired copies of the pEJ were active in these particular pEJ-transfected cells, while all copies of the transfected pEC gene in the other cells might be active. In such a case, the comparable levels of protein or RNA observed would not accurately reflect the intrinsic transcriptional activities of the two genes.

However, one point emerged with clarity: a level of EJ-specified p21 induced transformation, while a comparable level of the proto-oncogene-specified p21 had no effect on cellular phenotype. Since the p21 proteins are the only apparent gene products encoded by these genes, it was concluded that the difference in function between the EJ oncogene and the proto-oncogene must derive from structural alterations in the p21 protein. Conversely, regulatory alterations did not appear critical to the transforming activity of the oncogene.

Because of this, new importance was attached to the previously detected slight variations in migration rates of the p21 proteins from different cells (FIGS. 2b and 2c). Therefore, the p21 protein was re-analyzed under conditions in which migration differences could be more readily resolved. The results are presented in FIG. 5. Specifically, cells were metabolically labelled with $^{35}$S-methionine for three hours; cell lysates were prepared, immunoprecipitated and analyzed as previously described. Lysates from the cell line EJ/Gpt-3 (Lanes 1, 3) and-from the cell line EC/Gpt-1 (Lanes 2, 4) were-precipitated with the monoclonal anti-p21 antiserum Y13-238 (Lanes 1, 2) or with non-immune serum (Lanes 3, 4). Schematic diagrams (Lane 5: EJ/Gpt-3; Lane 6: EC/Gpt-1) show both the relative positions of the detected p21 bands and the relationships of those bands (arrows) based upon kinetic data and previously published experiments. See Shih, T. Y. et al. *J. Virol.* 42: 253–261 (1982).

Figure 5:
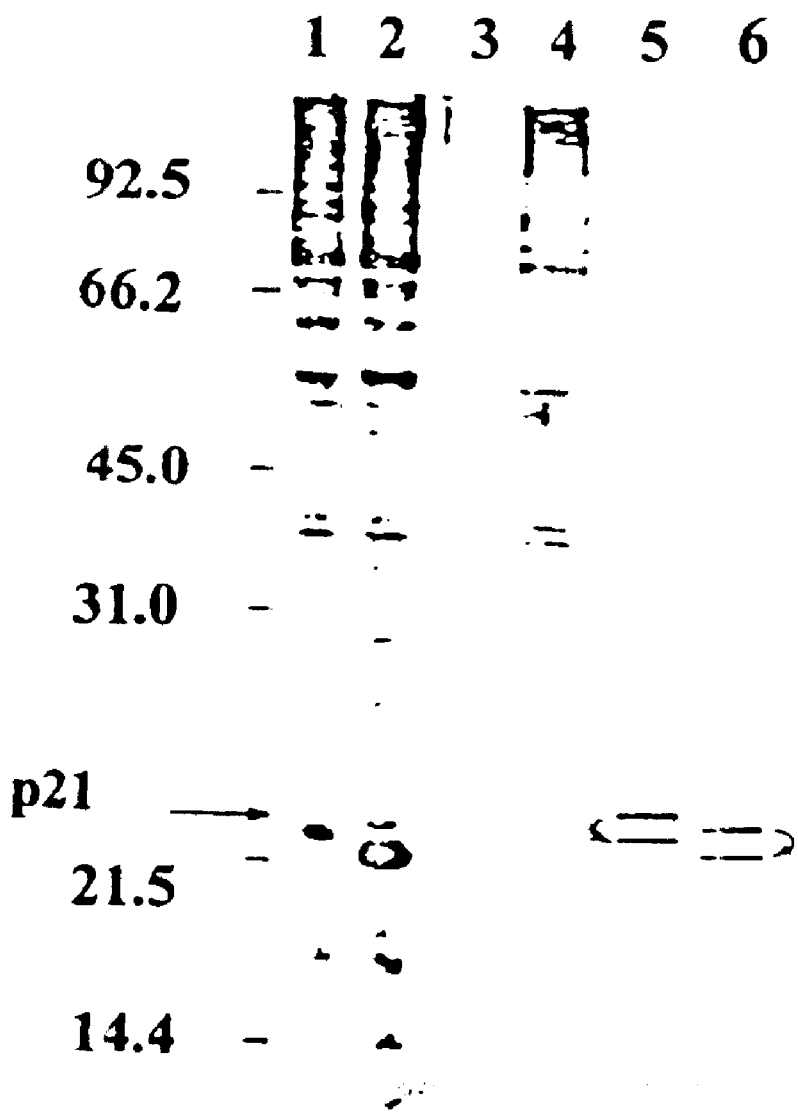
FIG. 5 presents electrophoretic gel patterns of immunoprecipitated p21 protein from cells transfected with pEJ or pEC.

The data of FIG. 5 indicate that the pEJ and pEC transfectants each exhibited two bands of p21. The higher molecular weight p21 protein of the pEJ transfectant migrated more slowly than the higher molecular weight protein of the pEC transfectant and the lower molecular weight p21 of the pEJ transfectant also migrated more slowly than the lower molecular weight p21 of the pEC transfectant. In each case the more slowly migrating band behaved as a kinetic precursor to the more rapidly migrating band. Comparable data on the p21 protein of v-Ha-ras previously indicated that the higher band underwent post-translational cleavage to yield its lower, more rapidly migrating partner. See Shih, T. Y. et al. *J. Virol.* 42: 253–261 (1982).

Since none of these p21-proteins appeared to be phosphorylated to any extent, the differences in migration rates between the pEC and pEJ proteins were most readily attributed to alterations in the number of amino acids or to changes in conformation.

The data and the schematization of FIG. 5 may provide an explanation for the complexity of p21 proteins seen in normal and transformed bladder cells (FIG. 2b): the normal cells exhibited two bands, reflective of the expression of a proto-oncogene; the carcinoma cells appeared to exhibit four bands, two being specified by the oncogene of these cells, and two by the normal, proto-oncogene of the other homologous chromosome.

The physical differences observed between p21 protein from oncogenes and proto-oncogenes might have reflected functionally important changes in the p21 protein, or alternatively, might represent differences which did not affect the process of transformation. To determine this, a series of independent experiments was designed to localize genetically the regions of the oncogene that specified the altered migration rates of the protein and the change in the gene function. These experiments depended upon in vitro homologous recombination between clones of the two genes.

Figure 6:
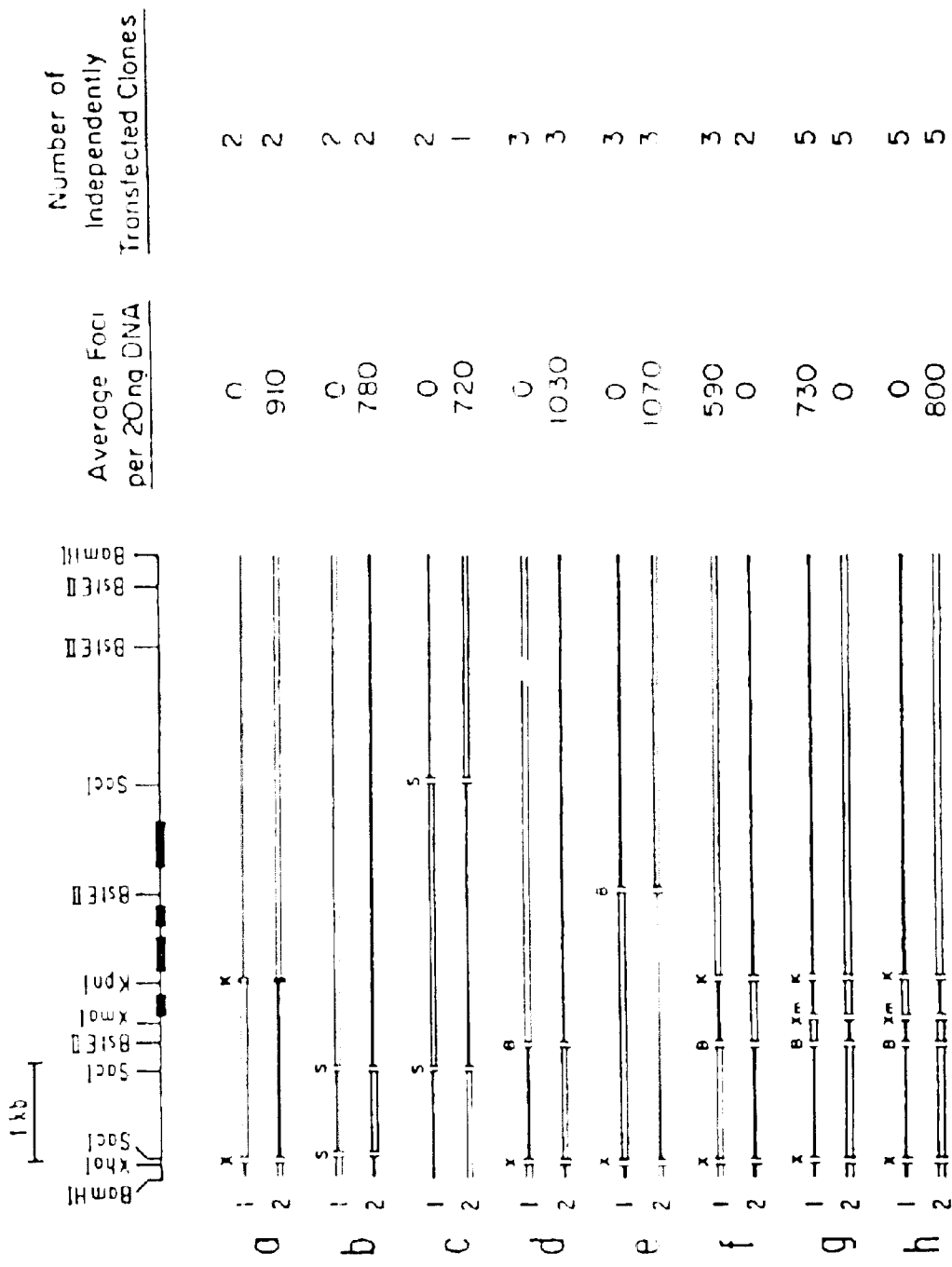
FIG. 6 is a schematic illustration of in vitro genetic recombinants constructed from the EJ transforming gene and its normal cellular homologue and also contains a summary of transfection and transformation data for experiments conducted with such genetic recombinants.

The experimental strategy was to excise a restriction fragment out of the oncogene clone (pEJ) and use it to replace the homologous piece of the proto-oncogene clone (pEC). At the same time, the reciprocal construction would be carried out by splicing the fragment of the proto-oncogene clone into the oncogene clone. These recombinant constructs were then tested for transforming ability in the transfection assay. The assay measured the ability of a fragment of the oncogene to impart transforming activity when placed in the midst of the proto-oncogene clone, and conversely, in the reciprocal recombination, for the loss of activity when the corresponding proto-oncogene fragment was inserted into the oncogene clone was determined. FIG. 6 presents a diagram of the specific constructions undertaken and a summary of the transfection and transformation data obtained.

The restriction map shows the cleavage sites for various enzymes within the 6.6 kb BamHI insert in pBR322. All sites specific for the enzymes are shown except for XmaI which acts in several other places which have not been well characterized. The site shown is the only XmaI site between the first BstEII-site and the KpnI site. The solid boxes on the map show the locations of coding exons.

In FIG. 6, pEJ/pEC chimeras are shown with segments derived from pEJ shown as solid bars and segments from pEC shown as open bars. pEJ and pEC were cleaved with the indicated enzymes either to completion or in a partial digest as required to obtain each indicated fragment. The products were separated by electrophoresis through 1.2 percent agarose and eluted by melting a NaI and absorbing to glass beads. The fragment containing pBR322 was then treated with calf intestinal phosphatase. The indicated fragments were joined either with the enzyme T4-DNA ligase or in a mock ligation without enzyme. Constructs a–e were made in bimolecular ligations. Constructs in f were made by mixing the three fragments simultaneously and in g and h by mixing the four fragments simultaneously. The ligation mixtures were directly transformed into the HB101 strain of *E. coli*. Only when colonies from mock ligations were less than 2 percent of the ligations were colonies analyzed for the presence of clones having appropriate restriction maps. Twenty ng of each clone was transfected into NIH3T3 cells as previously described and then carried without selection until foci were visualized in 10–14 days. Results of the transfections are shown in the first column. The second column shows the number of independent bacterial colonies screened and then transfected into NIH3T3 cells.

It was vital to verify that the transforming clones were indeed chimeras of the mixed pEJ and pEC origin, rather than contaminants of one origin or the other. This was done in three ways. In the simpler constructions, involving ligations of two fragments at a time, the results obtained with amplified recombinant clones were verified by directly transfecting the unamplified products of ligation reactions and of mock ligations containing isolated fragments not treated with the ligase. A second confirmation depended on the fact that the plasmids pEJ and pEC contained their respective cellular genes inserted in the pBR322 plasmid vector in opposite orientations. Thus, the origin of one parent of a recombinant could be determined by diagnostic restriction digests of the flanking plasmid regions. Since contaminating pEC could itself not give a false positive result, any active clone carrying proto-oncogene flanking sequences must have arisen as a consequence of the acquisition of portions of the transforming gene. Finally, the results were confirmed with several independent clones obtained from a ligation reaction.

As seen in FIG. 6, a genetic region 350 nucleotides long was ultimately identified which, when transferred from the oncogene to a corresponding region in the proto-oncogene, was able to impart activity to the latter. This region extended from the first XmaI endonuclease site to the KpnI site.

Fifty-five percent of this region consists of the first coding exon, 10 percent is 5' to the exon and 35 percent is part of the first intron.

Prior experiments had identified a difference in the migration of the p21 protein encoded by the oncogene and the proto-oncogene. Having now determined a short region of the gene which contained the transforming lesion, it became important to ascertain whether the region also contained the specificity for the altered protein. Therefore, immunoprecipitation of cells transfected with the products of the in vitro recombinants were performed.

NIH3T3 cells transformed with the EJ bladder tumor oncogene, its normal proto-oncogene, or recombinants between the two genes were first biologically cloned in 0.35 percent agar and then metabolically labelled with $^{35}$S-methionine for 18 hours. Lysates were prepared and immunoprecipitated ($5 \times 10^6$ cpm of TCA-precipitable counts) by a monoclonal antibody which detected the p21 encoded by Ha-MuSV but not the p21 encoded by Ki-MuSV (Y13-172). See Furth, M. E., David, L. J., Fleurdelys, B. and Scolnick, E. M. *J. Virol.* 43: 294–304 (1982); and, Shih, T. Y., Weeks, M. O., Young, H. A. and Scolnick, E. M. *Virology* 96: 64–79 (1979). Dissolved immunoprecipitates were then resolved by electrophoresis in a 12 percent SDS-polyacrylamide gel, and the results are presented in FIG. 7 as: Lanes 1–7a, No antibody; Lanes 1–7b, Anti-Harvey p21 monoclonal antibody. Cell lysates were from: NIH3T3 cells (Lane 1); cells transformed with the proto-oncogene [the LTR-activated 3 kb SacI fragment described in Payne, G. S. et al., *Cell*, 23:311–322 (1981)] (Lane 2); clone 504-17, transformed with the EJ oncogene (6.6 kb fragment in pBR) (Lane 3); clone 511-74, transformed with the ligation of proto-oncogene 1 kb SacI fragment to EJ oncogene 3 kb SacI fragment (Lane 4); clones 510-9 and 510-13, transformed with ligations of a fragment of the EJ oncogene extending from the XhoI site to the second BstEII site to a clone of the proto-oncogene from which the homologous fragment had been removed (Lanes 5, 6); and clone 508-8, transformed with the ligation of the EJ oncogene to the left of the KpnI site to the proto-oncogene to the right of this site (Lane 7).

Figure 7:
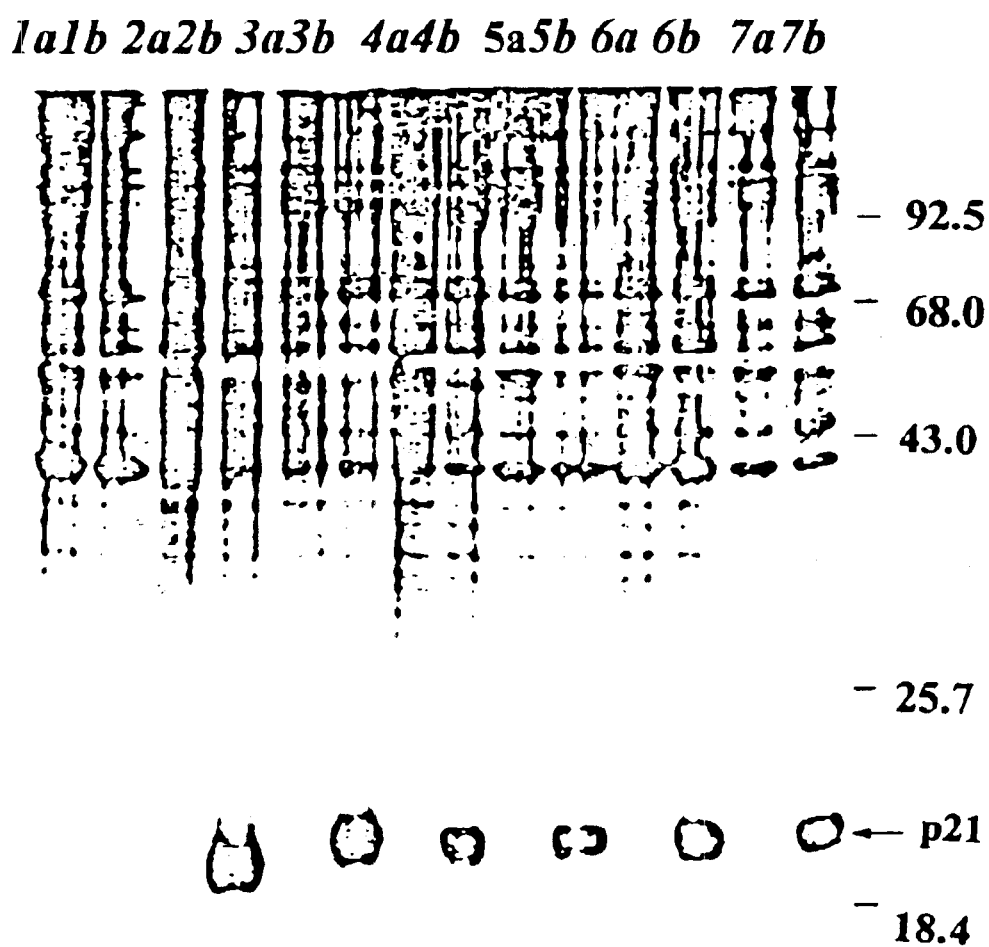
FIG. 7 presents electrophoretic gel patterns for migration of p21 proteins immunoprecipitated from cells transfected with in vitro recombinants of the EJ oncogene clone (pEJ) and its homologous proto-oncogene clone (pEC).

As can be seen in FIG. 7, the protein brought down in lysates from Xho-BstEII, SacI-SacI, and BstEII-KpnI recombination transfectants all comigrated with the EJ protein and had a mobility which differed from that of the EC protein. Labelling the cultures for 18 hours resulted in high levels of label in the lower molecular weight forms of the p21, and indetectable amounts of label in the kinetically unstable higher molecular weight forms. From the data obtained, it was concluded that the phenotypes of oncogenic transformation and altered electrophoretic-migration cosegregate, and the two were encoded by the same 350 nt segment of DNA. The altered migration rate was considered likely to be a reflection of a functionally important alteration of a protein.

Figure 8:
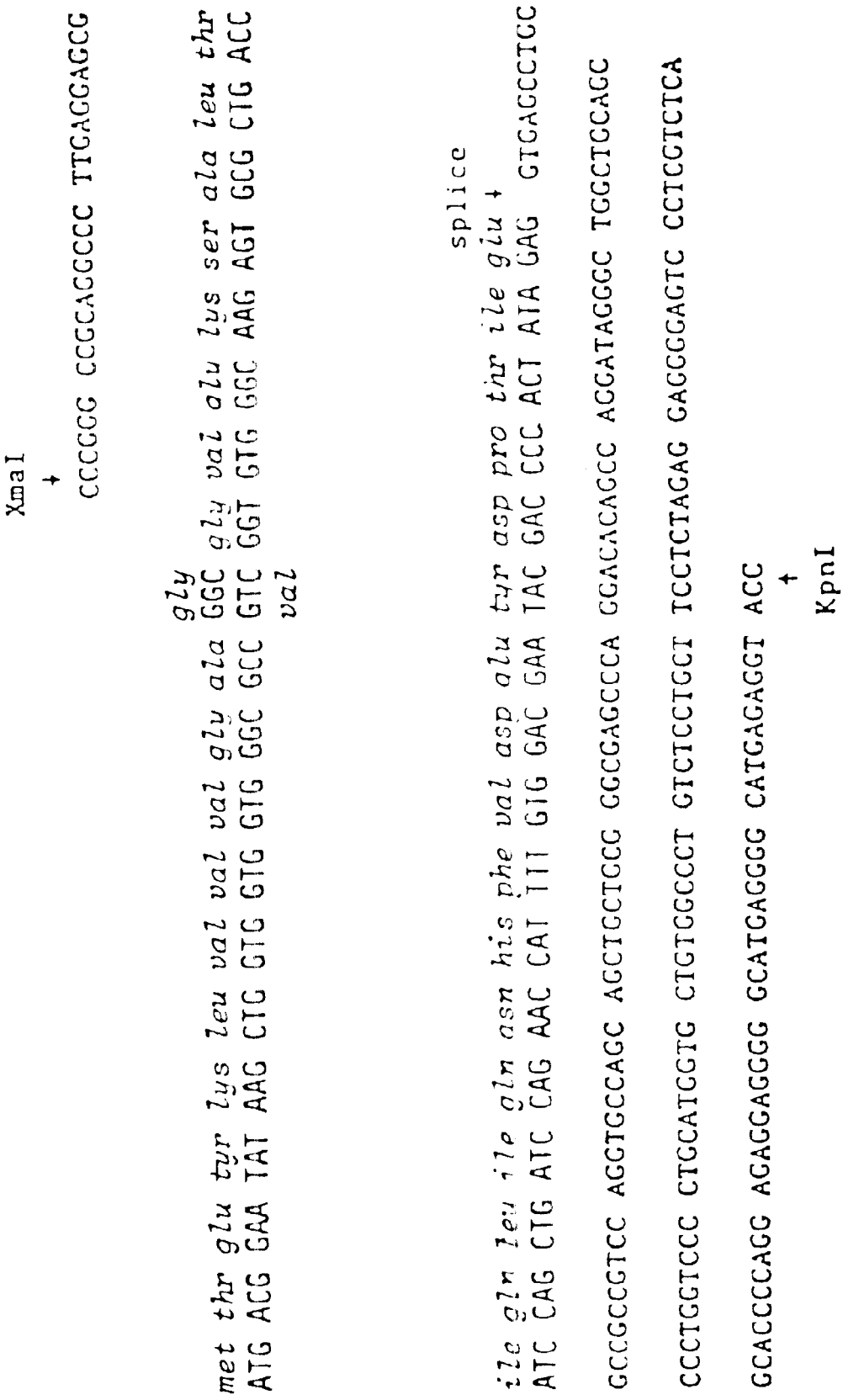
FIG. 8 illustrates a comparison of the DNA sequence of the molecular clone of the EJ transforming gene and its non-transforming cellular homologue and also sets forth the amino acid sequence expressed for each.

The short (350 kb) fragment shown to have biological significance was sequenced for DNA from the oncogene and the proto-oncogene. Sequences were determined by the forward and backward dideoxy DNA sequencing technique of Seif et al. and by the chemical procedure of Maxam and Gilbert. See Seif, I. et al., *Nucl. Acid Res.* 8: 2225–2238 (1980); and, Maxam, A. H. and Gilbert, W. *Proc. Natl. Acad. Sci. USA* 74: 560–564 (1977). The results are illustrated in FIG. 8 wherein the coding DNA strand is shown together with the inferred amino acid sequence. Where EJ and the proto-oncogene differ, both codons and amino acids are indicated.

As can be seen in FIG. 8, the only difference between the two DNA segments is in the p21 encoding region of the first known exon, specifically 60 nucleotides from the Xma cleavage site. It occurs in a triplet that encodes glycine in the normal rat and human c-Ha-ras genes. The sequence observed in the EJ oncogene encodes for valine. Thus, this alteration is responsible for the alteration in function of the p21 protein, and for the oncogenic activation of the c-Ha-ras gene that occurs in the EJ bladder carcinoma.

One consequence of the single base change is the alteration in the cleavage site of two different site-specific endonucleases. The sequence GCCGGC occurs in the proto-oncogene, and thus represents a recognition site for the endonuclease NaeI. This sequence also contains the CCGG recognition site of the endonuclease HpaI. Both of these are changed in the oncogene, whose sequence in the region reads GCCGTC.

NaeI endonuclease was used to independently verify the differences between the two sequences. NaeI was used instead of HpaI because NaeI cleaves DNA less frequently than HpaI. As expected, the pEC clone exhibited one more cleavage site in its inserts than its pEJ counterpart. This also provided, retrospective verification of the in vitro recombinant clones. The allele specifying transformation and abnormal p21 migration was seen to precisely co-segregate with the allele disallowing NaeI cleavage at this site.

Figure 9:
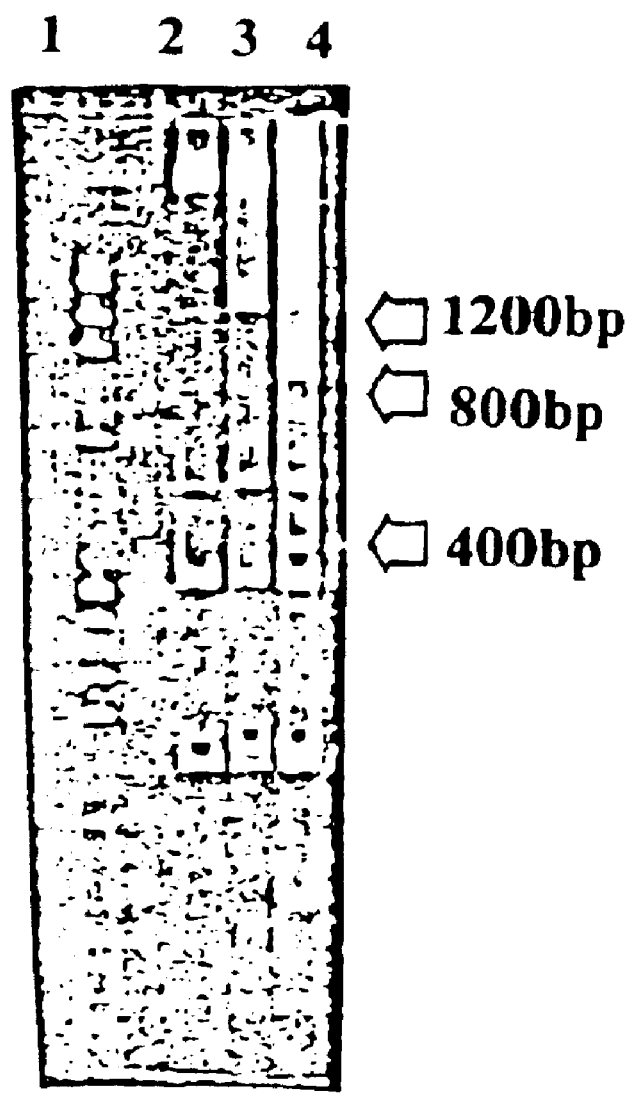
FIG. 9 presents electrophoretic gel patterns illustrating differences in fragments of clones of the EJ and EC genes created by the NaeI restriction enzyme.
Figure 10:
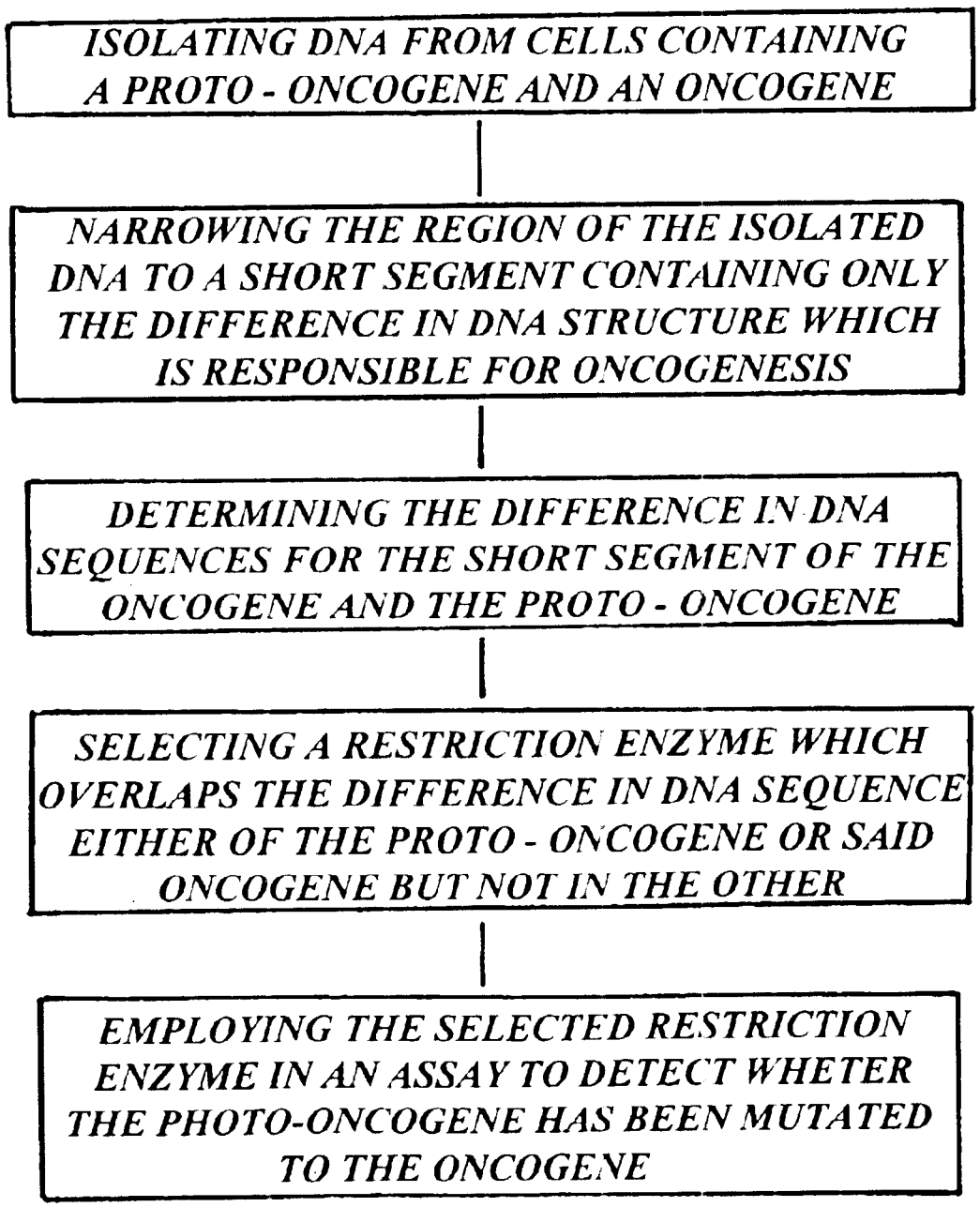

FIG. 9 presents the results of an NaeI restriction enzyme assay of the EJ oncogene and its corresponding proto-oncogene. According to the methods described it was determined that there should exist an NaeI restriction site in the proto-oncogene which should be lost in the alteration which produced the oncogene. Molecular clones of the oncogene (pEJ) and proto-oncogene (pEC) and the plasmid into which each was cloned (pBR322) were each purified by known methods. One microgram of each was cut with the enzyme NaeI and the resultant fragments were resolved by electrophoresis through a 15 percent bis-acrylamide gel. The gel was stained by the intercalating dye ethidium bromide and photographed under ultraviolet light.

In FIG. 9, the lanes are: Lane 1 is Øx174 DNA cut with the enzyme HaeIII as a marker lane producing bands of known size; Lane 2 is pBR322 cut with NaeI showing fragments originating in the plasmid vector; Lane 3 is NaeI cleaved pEJ DNA; and, Lane 4 is NaeI cleaved pEC DNA.

The pEJ DNA contains a band migrating with a molecular weight of 1200 base pairs which is missing in the pEC lane. The pEC lane, however, has two extra bands, one of 400 bases and the other of 800 bases in length which are missing in pEJ lane. Thus, the NaeI site in pEC, which allows cleavage of the 1200 bp band into two bands of 400 and 800 bases, is lost in the creation of the EJ oncogene.

The simple substitution of valine for glycine on the p21 protein might not be expected to have such a profound change in the function of the p21 protein. Nevertheless, several considerations appear to confer importance on this structural alteration. The first stems from comparison of this domain of the p21 encoded by the human c-Ha-ras gene, the rat c-Ha-ras gene and the v-Ha-ras oncogene of Harvey sarcoma virus. The 37 residue long amino acid sequences encoded by the first exons of the two cellular genes are identical, indicating great evolutionary conservation of this region. Analysis of the Harvey sarcoma virus oncogene, however, has revealed that it deviates from its direct rat cellular antecedent in only one position in this domain, a glycine to arginine conversion at precisely the same residue that is altered in the EJ oncogene. Consequently, it can be speculated that alteration of this critical residue was important in both the activation of the v-Ha-ras gene from its rat cellular precursor, and in the activation of the EJ bladder oncogene from its normal human counterpart. A similar alteration may have been significant in the oncogenic activation of another member of the ras gene family, the v-Ki-ras gene of Kirsten murine sarcoma virus. The Kirsten transforming gene is closely related to the v-Ha-ras gene. See Dhar, R. et al., *Science*, 217:934–936 (1982). The only difference between the p21of v-Ki-ras and that of v-Ha-ras in the first 36 amino acids is at position 12 where the residue in Kirsten is serine. See Tsuchida, N., et al., *Science*, 217:937–939 (1982). This is the precisely the same site as altered in the EJ and Harvey sarcoma virus encoded p21s. While sequence information is not available on the cellular homologue of the v-Ki-ras, it can be speculated that a conversion from the glycine to a new amino acid residue at position 12 may also have been involved in the activation of this ras oncogene.

A second consideration stems from examination of the specific amino acid changes observed. In both cases, glycine is replaced by an amino acid having a relatively bulky side chain. Glycine represents an anomaly among the 20 amino acids because it lacks a side chain. Consequently, it is able to participate in extremes of bending and folding of the polypeptide backbone and is the strongest breaker of alpha-helices. See Cantor, C. R. and Schimmel, P. R. *Biophysical Chemistry*, Vol. I, p. 303, W.H. Freeman and Co., San Francisco (1980). Thus, replacements of glycine by valine or arginine represent abrupt changes in the local stereochemistry of a protein.

It is believed that loss of glycine at residue 12 represents a significant change in an essential domain of the p21 protein. A consequence of this change may be a conformational shift of the protein, leading in turn to the aberrant electrophoretic migration or processing of p21 proteins. A second, more important consequence is a profound effect on the function of the p21 protein. It is likely that this alteration affects interaction of the p21 with cellular targets. Precedent exists for other single amino changes having profound effects on cellular and organismic physiology. The most well-known of these is the sickle-cell syndrome, in which a glutamine to valine conversion affects the solubility of hemoglobin within erythrocytes.

The findings described herein seem to contradict a series of experiments of recent years indicating upregulation as the pivotal event in carcinogenesis. Such experiments include the activation of the myc proto-oncogene occurring during leukemogenesis of avian retroviruses [see Neel, B. G. et al., *Cell*, 23:323–334 (1981); and, Payne, G. S. et al., *Cell*, 23:311–322 (1981)]; and the demonstration that in vitro fusion of a retroviral LTR promoter and a cellular proto-oncogene results in an actively transforming gene [see DeFeo, D. et al., *Proc. Natl. Acad. Sci. USA* 78:3328–3332 (1981); Blair, D. G. et al., *Science*, 212:941–943 (1981); and, Change, E. J. et al., *Nature*, 297:479–483 (1982)]. These latter results are particularly germane, since some of them demonstrate activation of clones of the rat and human c-Ha-ras proto-oncogenes. It is unlikely that the protein-encoding sequences of these c-Ha-ras genes have undergone any structural changes during construction of these viral-cellular chimeras. Rather, it appears that the only essential difference between the proto-oncogenes and their LTR-activated counterparts lies in rates of expression. This means that the ras proto-oncogene can be activated by a second independent mechanism, in principle as effective as creating an oncogene as the one described herein.

Oncogenes of other tumors have also been traced to ras genes. Specifically, colon and lung carcinomas have been found to carry oncogenes derived from activation of cellular Ki-ras genes. See Der, C. et al., *Proc. Natl. Acad. Sci. USA*, 79:3637–3640 (1980). Therefore, it is likely that activation of many of these oncogenes also depend upon structural alterations similar to those reported above.

As described previously, alteration of the $Gly_{12}$ codon in the EJ oncogene makes possible a simple diagnostic assay for carcinogenesis or transformation caused by alteration of this codon in the oncogene. Any mutation of the $Gly_{12}$ codon which occurs during carcinogenesis or related processes alters the cleavage recognition site for the NaeI and HpaI endonucleases, and render the altered DNA of the oncogene resistant to cleavage of this site. Thus, any test of the cleavability of the DNA at this site by these endonucleases constitutes a diagnostic test for the mutational alteration of this region of the proto-oncogene.

This test can be performed by treating DNAs of interest with NaeI, for example, resolving the resultant fragments by agarose gel electrophoresis, transferring the resolved fragments to a cellulose nitrate filter, and detecting the transferred fragments by incubation of the filter with a radiolabelled, sequence-specific probe followed by radioautography. The procedures are well known. See Southern, *J. Mol. Biol.*, 98, 503–17 (1975).

The sequence probe used in such experiments can derive from any one of a number of DNA segments which overlap the region of the proto-oncogene, or which lie closely adjacent to this region of the proto-oncogene. In the example described, the sequence probe could be the NaeI fragment of the oncogene beginning at the NaeI site to the left of the altered codon and ending at the NaeI site to the right of it. DNA of a cell carrying the normal proto-oncogene would be cleaved into two parts at this site by the NaeI, while DNA of the EJ bladder carcinoma oncogene is unaffected at this site by treatment with a NaeI endonuclease.

This assay may be made general for the alteration of DNA of a proto-oncogene for its corresponding oncogene. Sensitivity to cleavage by a restriction endonuclease at a DNA sequence of either the proto-oncogene or oncogene, but not the other, is the fundamental concept.

A difference between one or more bases in the proto-oncogene and oncogene provides a basis for employing polynucleotide probes in assays to detect carcinogenesis of cells. Polynucleotide probes are segments of single-stranded DNA that will seek out and bind to complementary sequences of DNA or RNA in a sample. Polynucleotide probes have typically contained a small number of bases, e.g., 15, but more or less could be employed to achieve the desired specificity for detecting a nucleotide sequence specific for a particular proto-oncogene or oncogene.

A specific illustration of a polynucleotide probe resulting directly from the work described herein could be based upon the single base change noted between the DNA sequences of pEC and pEJ. As noted above, a portion of the proto-oncogene is the sequence GCCGGC whereas the corresponding portion of the oncogene is the sequence GCCGTC. Thus, a polynucleotide probe specific for one of these sequences, but not the other, could be used in an assay to detect whether DNA from test cells contained the proto-oncogene or the oncogene. This would indicate the presence or absence of bladder cancer.

The polynucleotide probes can be produced by cloning procedures. In such cloning procedures, a vector, such as a virus or bacterial plasmid, is recombined with the desired DNA fragment which forms the probe. The vector is then introduced into cells in which the recombined vector is amplified by the cellular machinery thereby allowing cellular production of the probe.

These polynucleotide probes could be labelled with radioactive labels or non-radioactive (non-isotopic) labels. Typical radioactive labels include isotopes of hydrogen ($^3$H), phosphorus ($^{32}$P), carbon ($^{14}$C) or iodine ($^{125}$I). Non-isotopic labels include labels which fluoresce or can be made to fluoresce, as well as enzyme labels. Specific non-isotopic labelling techniques involving biotin groups are described by Langer et al., *Proc. Natl. Acad. Sci. USA* 79, 6633–7. (1981) and Singer et al., ibid. 79, 7331–35 (1982), the teachings of which are hereby incorporated by reference.

Polynucleotide probes are annealed with denatured DNA employing various blotting techniques, or are hybridized with RNA isolated from test cells. Such techniques are known to those skilled in the art. See, for example, *Molecular Biology of the Cell*, eds. Alberts et al., Garland Publishing, Inc., New York (1983), pages 185–194, the teachings of which are incorporated by reference.

Thus, an assay for detecting carcinogenesis caused by mutation of a proto-oncogene into an oncogene comprises employing a labelled polynucleotide probe specific for a nucleotide sequence present in or transcribed from one of the proto-oncogene or the oncogene but not the other. An assay for carcinogenesis in human cells can be performed by isolating DNA or RNA from the test cells and thereafter contacting the DNA or RNA with a labelled polynucleotide probe specific for either an oncogenic or proto-oncogenic sequence in the DNA or RNA transcribed therefrom and thereafter determining whether the probe hybridizes to the DNA or RNA.

Reagents for employing these polynucleotide probes can be assembled into a kit. Thus, a kit might contain, in addition to the probe, one or more buffers, reagents for labeling the probe, reagents employed in Southern or other blots, etc.

Another consequence of the change in amino acid sequence of the p21 protein encoded by the proto-oncogene from the p21 protein coded by the oncogene relates to detection of either by specific serological reagents. The serological reagents can be specific for the normal, proto-oncogene-specified amino acid sequence at this site of the protein, or be specific for the altered oncogene-specified amino acid sequence at this site of the protein. Other serological reagents could be employed that are reacted with a region of the protein that is unaltered, and consequently reactive with either normal or abnormal forms of the p21 protein.

Using cloning techniques, significant amounts of p21 protein encoded for by the normal site of the proto-oncogene, or by the altered site of the oncogene, can be isolated. Such protein segments could be used to produce antibodies by standard antibody production techniques. Thus, for producing polyclonal antibodies, such proteins would be employed to immunize a host, such as a rabbit or a rat, and antibodies to the protein would be collected from serum obtained from the host.

Alternatively, monoclonal antibodies could be produced employing cells which produce antibodies to the protein produced by the isolated gene segment, in typical fusion techniques for forming hybridoma cells. Basically, these techniques involve the fusing of the antibody producing cell with a cell having immortality, such as a myeloma cell, to provide a fused cell hybrid which has immortality and is capable of producing the desired antibody; in this case, an antibody to the normal or altered segment of p21 protein coded for by the isolated gene segment. The hybrid cells are then cultured under conditions conducive to the production of antibody after which antibody is collected from the cell culture medium. Such techniques for producing monoclonal antibodies have been well described in the literature. See, for example, U.S. Pat. Nos. 4,172,124 and 4,196,265, issued to Hilary Koprowski et al., the teachings of which are hereby incorporated by reference.

More specifically, such serological reagents can be developed by the known methods. See Walter, G. et al., *Proc. Nat'l. Acad. Sci. USA*, 77:5197–5200 (1980); Lerner, R. A. et al., *Proc. Nat'l. Acad. Sci. USA*, 78:3403–3407 (1981).

In practice, a peptide segment can be synthesized by a standard organic synthetic technique, the sequence of this peptide corresponding precisely with the amino sequence of the region of interest of the protein to be studied. This peptide can then be coupled to a carrier protein and injected into a suitable host (e.g., mouse) to illicit an immune response. The serum of the animal immunized in this fashion is then used to immune-precipitate both the immunizing peptide, and more importantly, the protein carrying this amino acid sequence in one of its domains. Consequently, a serum can be made against an oligopeptide sequence (e.g., decapeptide) spanning the amino acid residue site that is altered during the conversion of the normal proto-oncogene to the oncogene. Such serum can be made against the normal peptide sequence, or alternatively, against the altered sequence. The specificity of the immunoglobulin-antigen interaction will insure that the serum reacting with one oligopeptide will only react with the protein bearing the same, corresponding sequence in one of its domains and not cross-react with a protein bearing an altered version of this sequence in one of its domains.

P21 protein can be immune-precipitated from a tumor sample or from a tissue homogenate or from fluid released by an autolysing tumor fragment by use of the general, non-specific p21 serum that cross-reacts with domains of the protein (e.g., C-terminal) that are unaffected by the mutation-induced alterations described here. Independently, the serum with specificity against the N-terminal normal peptides surrounding residue 12 can be used to immune-precipitate protein from the same lysate. If this N-terminal specific serum, which is able to immune-precipitate normal p21 from the non-pathological tissue, is unable to immune-precipitate p21 from a test tissue of interest, then the p21 of this test tissue can be presumed to be altered in a fashion affecting its ability to react with serum reactive with the normal N-terminal sequence. The amount of p21 immune-precipitated from this tissue by the general, non-specific serum serves as a control for the amount of p21 which should be precipitable by the serum reactive with the normal N-terminal sequence.

The above immune-precipitation can be used as a measurement of the presence of altered p21 in a tissue sample. Independent of this, a series of peptide specific sera can be developed to diagnose which type of specific alteration has occurred to alter the normal amino acid sequence of this region into an abnormal sequence. For example, a list can be made of the amino acid replacements that can occur by simple point mutation at the codon encoding residue 12. For each of these replacements, a new version of the oligopeptide sequence of this region can be deduced, and a corresponding peptide synthesized for use as described above. Each one of these sera would be specifically reactive with the altered p21 corresponding to the oligopeptide fragment used to induce the serum in question.

The term "immune-precipitation" is further described by a series of alternate technical procedures. A commonly used technique is that of immune-precipitation of metabolically labelled proteins, followed by gel electrophoresis and autoradiography of the resulting gel. Because of difficulties in metabolically labelling tissue samples, an alternative is preferred here, that being the use of gel-electrophoresis of non-labelled proteins, transfer of the resolved proteins to a nitrocellulose filter, and detection of proteins of interest by incubation of the filter with radio-labelled immunoglobulin. The immunoglobulin can be radiolabelled either by direct iodination, or indirectly, by incubation of the immunoglobulin with a second, radiolabelled immunoglobulin that reacts with constant regions of the first immunoglobulin.

Although the discussion in this application, and much of the experimental work, has been devoted to detecting differences in the EJ gene for human bladder cancer and the proto-oncogene, c-Ha-ras, the techniques for detecting these differences, as well as the assays based thereon, are much more general in nature. In fact, it is believed that such techniques and assays apply to any wild-type gene or allele which has been mutated to create a mutant allele or gene which has a dramatically different function from the wild-type allele. For example, such techniques and assays would be expected to be suitable for use in detecting differences in the wild-type gene and the mutant gene responsible for Lesch-Nyan Syndrome.

The techniques have particular application and advantage, of course, in detecting differences between oncogenes and proto-oncogenes. Members of the ras family of genes have been discussed previously. However, the techniques described herein also lend themselves to finding differences between proto-oncogenes and oncogenes other than members of the ras family. For example, differences between the oncogene present in the HL-60 cell line, known to be responsible for promylocytic leukemia, certain colon cancers, and Hairy cell leukemia, and its proto-oncogene could be determined using procedures described herein. These differences could then be employed in assays of the type described.

A very general protocol for assaying for differences in a wild-type gene and its correspondent mutant gene is as follows:

A. Develop an in vitro assay for the activity of a gene, the functioning or malfunctioning of which is responsible for the phenotype of a genetic disease. Such in vitro assay will, in general, depend upon an observable alteration in behavior of a cultured cell that has acquired the gene via gene transfer.

B. Use the in vitro assay to isolate as a molecular clone an allele of the above gene. Such allele may either by a wild-type allele or a malfunctioning allelic variant of the wild-type allele.

C. Use the isolated allele from Section B to isolate other allelic forms of the gene using recombinant DNA techniques. Thus, the normal allele could be used as sequence probe to enable identification and isolation of a variant, non-wild-type allele.

D. Demonstrate the observably different and distinct behaviors of the wild-type allele and a non-wild type variant in the in vitro assay system.

E. Perform in vitro genetic recombination between the clones of the wild-type and non-wild-type allele followed by testing of the recombinants in the in vitro assay system, assaying for the phenotype induced by a wild-type or non-wild-type allele in this system (Part D). In this fashion, map genetically the region of the non-wild-type allele that is responsible for the differences in function between the two alleles.

F. Perform structural sequence analysis of the region of the non-wild-type allele demonstrated (Part E) to encode the functional difference between the two alleles.

G. Having identified a crucially altered sequence (Part F), the existence of which determines the altered phenotype of the non-wild-type gene, identify one or more site-specific endonucleases (restriction enzymes) the cleavage recognition site of which was altered during the processes which converted a wild-type allele into a non-wild-type allele.

H. Use the cloned wild-type gene as sequence probe to screen to DNAs of test samples or test tissue to determine whether or not said test DNA carries a sequence alteration in that gene, and that portion of said gene which has been previously shown (Part E) to be critical in affecting function of said gene and its non-wild-type allelic variants, screening for the presence or absence of the restriction endonuclease site (Part G) the alteration of which has previously been shown to affect functioning of the gene.

I. Deduce the amino acid sequences encoded by the normal wild-type allele of the gene and its non-wild-type variant forms. Determine whether the previously mapped nucleotide sequence difference, which has previously been shown to affect functioning of the gene (Part F), affects as well the amino acid sequence of the proteins encoded by wild-type and non-wild-type alleles.

J. Should amino acid sequences be affected, develop antisera specific for the wild-type and non-wild-type proteins. For example, one could synthesize an oligopeptide fragment, the sequences of which reproduce the sequence of that domain of the non-wild-type protein which distinguishes it functionally from the wild type protein (Part I); synthesize the corresponding wild-type oligopeptide; use both as immunogens to elicit antisera that are specific for reacting with the wild-type or non-wild-type proteins.

K. Utilize said specific antisera (Part J) to screen proteins of test cells or test tissue for the presence of wild-type or non-wild-type versions of said protein.

L. Utilize said protein screening (Part K) to diagnose for the presence of proteins whose structure is important in mediating the phenotype of a genetic disease.

Activation and Characterization of the Rat Neu Oncogene

It has also been shown now that cellular genes other than the ras genes can be converted into oncogenes by point mutations. It has been shown that the rat neu proto-oncogene, which encodes a protein resembling a growth factor receptor, can also be converted into an oncogene by a single nucleotide alteration. Thus, it has been shown that the neu proto-oncogene (i.e., the nucleotide sequence present in the normal genome of normal non-tumor cells) can undergo mutational activation into its corresponding oncogene (i.e., the nucleotide sequence whose expression within a cell causes its conversion from a normal cell into a tumor cell) by a single nucleotide substitution. This point mutation, initially demonstrated in a rat neuroblastoma induced by transplacental exposure to ethylnitrosourea, has also been shown to occur in seven other neu oncogenes, each of which arose in a separate, independently induced by ethylnitrosourea exposure. Detection of the point mutations relied on the use of oligonucleotide probes specific for the region initially shown to contain the activating mutation. In all cases, the same amino acid substitution resulted: a valine normally present in the transmembrane region of the encoded p185 protein was replaced by a glutamic acid residue. This finding suggests that nucleotide substitution at only a limited number of sites in the neu proto-oncogene will result in its becoming an active oncogene.

Transfectants which arose from DNAs from ten methylnitrosourea-induced nervous system tumors which contained activated neu genes have also been shown to have the identical alteration in their DNA and are presumed to have the same sequence change as that present in the ethylnitrosourea-induced tumors, based on their differential hybridization to an oligonucleotide probe corresponding to the transforming gene. Thus, oligonucleotide probes homologous to the neu gene have been shown to be able to detect activated neu genes in tumors induced by exposure or second mutagen by exposure to methylnitrosourea. In addition, this demonstrates that both mutagens cause activation of neu genes at the same position and that activated neu genes can arise in both BDIX rats (ethylnitrosourea-induced tumors) and Buffalo rats (methylnitrosourea-induced tumors). This is described in detail in Example 9; also described below is its relationship to human homologs of the rat neu gene. Also described are nucleic acid probes and monoclonal antibodies which recognize the neu proto-oncogene or the neu gene-encoded product and can, thus, be used to determine the level of expression of the oncogene mRNA and gene product and methods for their use.

Human versions of the rat neu genes have been isolated and are also referred to as c-erbB2 or HER2. Yamamoto, T. et al., Nature, 319:230–234 (1986); Coussens, L. et al., Science, 230:1132–1139 (1985). The DNA sequences of both the rat and the human clones predict a 1260 amino acid protein product of the neu gene.

Mutational activation of the human homologs of the rat neu genes, referred to here as the human neu oncogenes, is thought to occur through a similar mechanism: single nucleotide substitution or point mutation in the human neu gene. It is highly likely that the single nucleotide substitution occurs in the region of the human neu proto-oncogene that corresponds with the region in the rat neu oncogene shown to contain the activating mutations. It is possible to determine the presence or absence of the activating lesion in the DNA of a variety of spontaneously arising human tumors through the use of oligonucleotide probes specifically reactive either with regions unique to the neu oncogene or with regions unique to the corresponding neu proto-oncogene. That is, hybridization probes can be constructed which will react (hybridize) with a nucleotide sequence occurring in either a neu oncogene or its corresponding proto-oncogene (but not in both). Such probes can be used to test human tumor DNAs for the occurrence of a point mutation responsible for activation of the neu oncogene. For example, radiolabelled oligonucleotide probes can be used in the Southern blot hybridization procedure to detect activation of the neu oncogene in human tumors of clinical interest.

Because the p185 proteins encoded by neu oncogenes are different from those encoded by their corresponding proto-oncogenes, it is also possible to develop serological reagents, such as polyclonal antibodies or monoclonal antibodies, which are specific for the altered or the normal amino acid sequences in such proteins. These reagents can be used to provide highly sensitive test cells for the presence or absence of neu oncogenes by detecting the occurrence of the mutated or altered gene products they encode.

As described below, the approach described has been used successfully in identifying the point mutation which causes activation of the neu proto-oncogene in DNA from a chemically induced (i.e., ethylnitrosourea-induced) rat neuroblastoma. It has also been used to verify the occurrence of the same activating point mutations, suspected to be present, in seven other neu oncogenes (each having arisen in a separate, independently (chemically) induced tumor).

In addition the approach has been used to detect the presence in DNAs from methy(nitrosourea-induced nervous system tumors of Buffalo rats. It has been demonstrated that all of the transfected neu genes bore the identical alteration as occurs in the DNA from the ethylnitrosourea-induced tumor. The approach described can be used, with modification, in identifying point mutations which cause activation of human neu oncogenes. In addition, it is possible to develop serological reagents, such as polyclonal antibodies or monoclonal antibodies specific for the altered or the normal amino acid sequences of the proteins encoded, respectively, by a neu oncogene or its corresponding proto-oncogene. These reagents can be used to test cells for the occurrence of the encoded protein and thus for the presence or absence of the neu oncogene.

This invention will now be further and more specifically described in the following examples.

EXAMPLE 1

Preliminary Characterization of the Bladder Cancer Transforming Sequences

In order to ascertain whether the transforming trait induced by EJ bladder carcinoma DNA was encoded by sequences carried within a single, contiguous segment of DNA, the yield of foci as a function of the amount of EJ tumor cell DNA used in a transfection assay was measured.

Genomic DNA was prepared from confluent cultures of cells which were washed twice with phosphate buffered saline (PBS). Lysis buffer (0.5% SDS 0.1 M NaCl, 40 mM Tris-Cl, 20 mM EDTA pH 7.0) containing 0.2 mg/ml proteinase K (Boehringer) was then applied onto cells directly. Cells were lysed completely, and the viscous lysate was incubated at 37° C. with gentle shaking for at least two hours. This was extracted twice with an equal volume of redistilled phenol, followed by two extractions with chloroform/isoamyl alcohol (24:1). The DNA preparation was then adjusted to 0.2 M NaCl final concentration before ethanol precipitation. Clumps of DNA precipitate were then removed with a Pasteur pipette and transferred to 10 mM Tris-Cl 1 mM EDTA (pH 8.0).

DNA from the human bladder carcinoma cell line EJ was applied to monolayer cultures of NIH3T3 mouse fibroblast and resulting foci were scored 14–21 days later. DNA transfection of NIH3T3 was carried out by the calcium phosphate precipitation technique of Graham and van der Eb as modified by Andersson et al. See Graham, F. L. and Van der Eb, A. J., Virology, 52:456–67 (1973); Andersson, P., Goldfarb, M. P. and Weinberg, R. A., Cell, 16:63–75 (1979). High molecular weight donor DNAs were sheared through a 20 gauge needle once. 75 ug aliquots of such sheared DNA was ethanol precipitated in 15 ml tubes and resuspended in 2.5 ml transfection buffer (0.7 mM $Na_2HPO_4$ 0.7 $H_2O$, 21 mM HEPES, 0.145 M NaCl pH 7.0). 125 ul of 2.5 M $CaCl_2$ was added and mixed by vortexing immediately. As soon as a blueish fine precipitate was apparent, 1.25 ml was applied onto $7 \times 10^5$ NIH3T3 cells in the presence of 10 ml 10% calf serum in Dulbecco's modified medium. To increase transfection efficiency, recipient NIH3T3 cells were plated 12–20 hours before use.

The calcium-phosphate DNA coprecipitate was removed from the dish by changing medium. Subsequent splitting of NIH3T3 cells into subcultures was found not to be necessary. Medium was changed twice per week. 14–21 days later, morphologically transformed foci were scored as described by Shih et al. See Shih, C., Shilo, B., Goldfarb, M. P., Dannenberg, A. and Weinberg, R. A., *Proc. Natl. Acad. Sci. USA*, 76:5714–18 (1979). A fluctuation of transfection efficiency with two fold range was observed. DNA transfection of cloned DNAs, 50–100 ng of DNA were mixed with 75 ug carried DNA (usually NIH3T3 or FS4 human diploid fibroblast DNA) before ethanol precipitation.

The results were:

| Dose of Transforming DNA | Dose of Added Carrier DNA | No. of Foci Induced by | |
|---|---|---|---|
| | | EJ DNA | EJ-6-2 DNA |
| 5 ug | 70 ug | 2 | 6 |
| 10 ug | 65 ug | 3 | 13 |
| 19 ug | 56 ug | 4 | 25 |
| 38 ug | 38 ug | 10 | 60 |
| 75 ug | — | 20 | 73 |

"EJ-DNA" was prepared directly from a culture of the tumor cell line. "EJ-6-2 DNA" was prepared from a culture grown up from a secondary focus.

The dose response of foci was roughly linear, as can be seen, which strongly suggests that the foci were not being induced by two or more unlinked, cooperating DNA sequences whose concomitant transfer was required for transformation.

EXAMPLE 2

Definition of DNA Fragment Containing Transforming Sequences

Transforming DNAs, obtained from the EJ cell line as described in Example 1, were exposed to various restriction endonucleases prior to transfection and tested to see whether the biological activity of the DNA survived enzyme treatment. Survival of biological activity would indicate that the functionally essential sequences were carried entirely within one of the many DNA fragments generated after enzyme treatment.

KpnI and PvuII were found to inactivate the transforming potency of DNAs prepared from EJ tumor cells. EcoRI was found to spare the biological activity. Identical results were obtained when cultures were grown up from transfected foci and their DNAs tested by enzyme treatment prior to a second round of transfection. It was concluded, therefore, that the transforming sequences were contained entirely within one EcoRI-generated fragment of EJ bladder carcinoma DNA.

EXAMPLE 3

Detection and Identification of the Transforming DNA Segment for Sequence Hybridization That fraction of human DNA which self-anneals at a rate of Cot=1 or less was employed as a probe. This probe was prepared from total cellular DNA from a human bladder carcinoma cell line A1663. The DNA concentration was adjusted to 125 ug per ml in 0.01 M PIPES buffer (pH 6.8), and sonicated to ca. 400 bp size fragments. Denaturation was done by boiling at 100° C. for ten min. The NaCl concentration was adjusted to 0.3 M and reannealing performed at 68° C. for 40 min. The solution was quenched on ice, equal volumes of 2×S1 buffer (0.50 M NaCl, 0.06 M NaOAc, 2 mM $ZnSo_4$, 10% glycerol, pH 4.5) was added, followed by addition of 20 ul S1 enzyme (Boehringer, $10^3$ units per ul). This was incubated at 37° C. for one hour. 1 M Na-phosphate buffer (equimolar mixture of $Na_2HPO_4$ and $NaH_2PO_4$) was added to 0.12 M Na-phosphate final concentration and the solution was passed through a hydroxylapatite column at 60° C. Double stranded DNA was then eluted with 0.4–0.5 M Na-phosphate buffer at 60° C. High salt was removed by extensive dialysis against 10 mM Tris-Cl, 1 mM EDTA (pH 8.0). This DNA was termed Cot=1 DNA.

1° (primary) and 2° (secondary) foci-were induced by serial passage of the EJ transforming sequence through NIH3T3 cells. Cultures were grown out from select foci and 11 ug of DNA of each culture were digested by endonuclease EcoRI, resolved by agarose gel electrophoresis, and transferred to a nitrocellulose filter. As mentioned above, a human repetitive sequence DNA (Cot=1) was used as a probe in sequence hybridization. DNA of 1° focus was termed EJ-3. DNAs of five different, independently induced secondary foci, were termed EJ-3-1, EJ-3-2, EJ-6-1, EJ-6-2, and EJ-6-3.

Two cycles of transfection through mouse cells assured that virtually the only human sequences present in a 2° transformant were those which were closely linked to the gene encoding the scored transforming trait. The sequence hybridization showed that a primary transfectant, which picked up the EJ transforming sequence after transfection of EJ tumor cell DNA, acquired concomitantly a large number of other human DNA sequences. But serial passage of the transforming sequence in a second round of transfection led to 2° foci, whose DNAs carried only a single large EcoRI fragment which was reactive with the human specific probe (i.e., the Cot=1 probe).

The large EcoRI fragment, of about 25 kb, represented a characteristic signature of the presence of the introduced bladder carcinoma gene. All cells which acquired the gene carried this fragment or one of very similar size. This co-segregation of large EcoRI DNA fragment and transforming sequences indicated that the two elements were closely linked.

To determine whether or not the transforming sequence was carried within the large Alu-containing EcoRI segment, the DNA of 2° transfectant EJ-6-2 was treated with EcoRI prior to a third round of transfection. DNA of 2° focus EJ-6-2 was treated with endonuclease EcoRI prior to a round of transfection used to induce a series of 3° foci. These 3° foci were picked and grown into mass cultures. The DNAs of these cultures were cleaved by endonuclease PvuII prior to Southern blot analysis as above. The Southern blot analysis indicated that all 3° foci still contained Alu sequences. Since the linkage between the oncogene and these Alu sequences could not be broken by EcoRI, it was concluded that these Alu blocs and the transforming sequences resided within the same EcoRI fragment. This fragment was, by necessity, the single large Alu-positive fragment which had been seen in the Southern blot analysis.

EXAMPLE 4

Molecular Cloning of a Transforming Segment

The strategy for molecular cloning of the large EcoRI fragment and associated oncogene began with insertion of EcoRI fragments of a 2° transfectant into lambdaphage vectors. The plan was to screen for components of the resulting library that exhibited sequences reactive with the Cot=1 probe. However, the EcoRI fragment containing the oncogene seen in the Southern blot had a size of about 25 kb, which exceeded the carrying capacity of available lambdaphage vectors. Nevertheless, in occasional 2° transfectants, smaller versions of the large Alu-containing EcoRI fragments had been observed. Such smaller fragments appeared to have resulted from mechanical breakage of the DNAs prior to transfection. Thus, truncated DNA fragments carrying the transforming and Alu sequences appear to have been become fused after transfection with new arrays of EcoRI sites present in co-transfected DNA.

An example of such DNA of the 2° focus line was EJ-6-2, found to carry an Alu-positive EcoRI segment of only 15–20 kb in the Southern blot, a size within the length limits of inserts allowed by the lambdaphage vector Charon 4A. This DNA fragment was the only human segment which could be detected in this cell line. Moreover, the DNA of this cell line was shown to be potent upon transfection, yielding as much as one focus per 2 ug of transfected DNA.

DNA of this cell line was prepared as follows. 280 ug of EJ-6-2 EcoRI cleaved DNA was extracted with phenol, cloroform, and then precipitated with phenol, chloroform, and then precipitated with ethanol. The total DNA pellet was then resuspended in 3 ml 10% w/v sucrose, 20 mM Tris-HCl (pH 8.0), 10 mM EDTA, 1 M NaCl. A 0.75 ml aliquot (70 ug) was then layered onto a 15–40% linear sucrose gradient (1 M NaCl, 20 mM Tris-Cl, pH 8.0, 10 mM EDTA) in Beckman SW27 centrifuge tube. The gradient was centrifuged at 23,000 rpm for 30 hours at 20° C. 1.5 ml fractions were collected and resolved on 1% agarose gel. DNA fragments were then transferred to a nitrocellulose filter via the Southern blot procedure. See Southern, E. M., "Detection of specific sequences among DNA fragments separated by gel electrophoresis," *J. Mol. Biol.* 98, pp. 503–518 (1975). Cot=1 DNA was used as a hybridization probe. Fractions containing the strongest signal were pooled, concentrated by ethanol precipitation and resuspended in 10 mM Tris-Cl, 1 mM EDTA (pH 7.0).

The enriched fragment mixture was linked to the genomic ends of the Charon 4A bacteriophage vector and packaged in vitro employing the Blattner et al. techniques mentioned above. An estimated $5 \times 10^5$ plaque forming units were plated and screened with Cot=1 probe for Alu-containing phage using the procedure of Benton and Davis. See Benton, W. D. and Davis, R. W., "Screening gt recombinant clones by hybridization to a single plaques in situ," *Science* 196, pp. 180–182, (1977).

Two phage stocks were isolated that retained reactivity with the human probe through three cycles of plaquing. These two phage stocks had identical inserted DNAs and only one will be further described. The Figure illustrates the cleavage site map of the inserted DNA along with the location of the human repetitive sequence blocs. A 6.6 kb biologically active sub-clone carried by a pBR322 plasmid vector is shown in the lower portion of the figure. The positions of the two Alu blocs were not precisely mapped within the BamHI-BamHI and BamHI-KpnI fragments in which they were found. The 6.6 kb insert is not cleaved by HindIII, BglII, SalI and SacII endonucleases.

DNA of this phage stock was able to induce foci at a frequency of ca. $10^4$ foci per microgram of transfected DNA. DNAs of several of these foci were analyzed. These DNAs carried copies of the transfected chimeric phage DNA, thus assuring that the observed foci did not arise from spontaneous transformation of cells in the transfected monolayer. Moreover, these acquired cloned DNAs carried arrays of restriction sites indistinguishable from those seen in the homologous DNA fragment present in the EJ-6-2, the cell line from which the genomic library was constructed. This confirmed the fidelity of the molecular cloning process.

EXAMPLE 5

Subcloning of the Inserted Sequences of the Bacteriophage

The 16 kb insert present within the bacteriophage was suspected to carry far more sequences that those necessary to induce transformation. Thus, sub-cloning of this segment was attempted in order to localize the essential transforming region and to discard sequences which were irrelevant to further analysis of the gene. Among the several restriction enzymes previously used to treat uncloned cellular DNAs, BamHI was seen to spare the transforming activity. It was also found that BamHI did not reduce the biological activity of the cloned phage DNA (data not shown). This indicated the presence of the functionally essential region of the gene entirely within one of the 4 BamHI fragments of the insert shown in the figure.

These four fragments were sub-cloned by excision from the bacteriophage with BamHI and ligation to BamHI-treated pBR322 plasmid DNA.

BamHI digested phage clone DNA was incubated with a 2 molar excess of calf intestinal phosphotase treated, BamHI cleaved pBR322 in the presence of T4 DNA ligase (New England Biolabs). This DNA was used to transform *E. coli* strain C600 according to procedure of Cohen et al. See Cohen, S. N., Chang, A. C. Y. and Hsu, L., *Proc. Natl. Acad. Sci., USA* 69:2110–14 (1972). Recombinant clones were selected for ampicillin resistance (50 ug/ml of tetracycline). Colonies responding appropriately to drugs were screened with both Cot=1 and phage DNA probes according to the protocol of Grunstein and Hogness. See Grunstein, M. and Hogness, D. S., *Proc. Natl. Acad. Sci., USA* 72:3961–65 (1975). Different sized subclones were picked. BamHI cleaved chimeric plasmid DNAs were analyzed on 1% agarose gels, and the identity of each subclone was determined by the size of the inserted sequences.

Since the transforming activity was inactivated by KpnI endonuclease, it was suspected that either BamHI fragments A or B carried the transforming sequence. Moveover, the gene could occasionally become unlinked from Alu sequences, by mechanical shearing which suggested that it was located on the more distantly linked BamHI fragment A.

These predictions were vindicated by transfection assay of plasmids carrying different BamHI fragments. On the chimeric plasmid DNA of 6.6 kb BamHI fragment was found to have biological activity, which was measured at ca. $10^4$ focus inducing units per ug. The chimeric plasmid DNA was of great utility since it carried no repeated sequences and could be used as a specific probe for the transforming gene.

FIG. 1 is an endonuclease cleavage map for the transforming DNA segment isolated from EJ human bladder carcinoma DNA. A map of the 15.5 kb insert present in the Charon 4A vector is shown in the upper portion. A 6.6 kb biologically active sub-clone carried by a pBR 322 plasmid vector is shown in the lower portion of FIG. 1. The positions of the two Alu blocks was not precisely mapped within the BamHI-BamHI and BamHI-KpnI fragments in which they were found. The 6.6 kb insert was not cleaved by HindIII, BglII, SalI and SacII endonucleases.

EXAMPLE 6

Presence of the Active Bladder Oncogene in EJ DNA Before Transfection

In order to rule out the possibility that the cloned sequence represented an oncogene which was inadvertantly activated either during the derivation of the EJ-6-2 transfectant or the subsequent cloning, the DNAs of a series of independently induced transfectants were analyzed for the presence of this gene.

DNAs were prepared from foci, cleaved with endonuclease BamHI, and analyzed in the Southern procedure using the plasmid-borne 6.6 kb sub-clone as probe. DNAs analyzed were from: (a) parental EJ bladder carcinoma line; (b) 2° focus EJ-1-1, a derivative of 1° focus EJ-1; (c) 2° focus EJ-3-1, a derivative of 1° focus EJ-3; (d) NIH3T3 cells; (e) 2° focus EJ-6-2, a derivative of 1° focus EJ-6; and (f) 1° focus EJ-7.

Southern blot analysis showed that these DNAS all carried copies of the acquired EJ bladder carcinoma oncogene. Since these transfectants derived originally from 4 independent primary transfection events, it was concluded that the active oncogene existed in the EJ bladder carcinoma DNA prior to the experimental manipulations which led to the derivation of these transfected cell lines.

EXAMPLE 7

Use of Cloned Sequence to Examine Normal Human DNA

The plasmid sub-clone was used to examine normal human DNA for the presence of homologous sequences. DNAs were cleaved with endonuclease EcoRI prior to Southern analysis, using the 6.6 kb plasmid-amplified sub-clone as probe. Hybridization was performed (part A) at normal stringency conditions in the presence of 50% formamide, or (part B) at lowered stringency (45% formamide). DNAs analyzed were from cultures of: Part A. (a) FS4 normal human diploid fibroblasts; (b) EJ human bladder carcinoma; (c) EJ human bladder carcinoma, (d) T24 human bladder carcinoma obtained from J. Fogh. Part B. (a) FS4 normal human diploid fibroblasts; (b) EJ human bladder carcinoma; (c) EJ-(RI, religated)2 1° focus prepared by EcoRI cleavage of EJ tumor cell DNA followed by religation before transfection; (d) T24 human bladder carcinoma cell line; (e) J82 human bladder carcinoma cell line; and (f) HT1376 human bladder carcinoma cell line.

It could be seen in the Southern blot analysis that normal human diploid fibroblast DNA contains a DNA fragment which is strongly reactive with the bladder carcinoma oncogene probe. This indicated that the active oncogene could derive from a very closely related sequence which is present in the normal human genome. The result argued against the possibility that the oncogene was of exogenous origin, such as a sequence introduced into the cell by viral infection. This conclusion was reinforced by further structural analysis described below.

The survey of the normal human genome revealed that the cross reacting EcoRI fragment was of a size which was similar to that which had been acquired from the tumor cell transfection. Moreover, a similarly sized, large EcoRI fragment was detected in a variety of human tumor DNAs, including the EJ, T24, J82 and HT1376 bladder carcinoma cell lines.

Of additional interest is the presence of homologous fragments of 9.2 kb and 11 kb which were present in normal human DNA. These presumably represented related sequences present in the human genome. These related sequences were not detected after more stringent hybridization and washing conditions. As expected, these two other fragments were not present in the DNA of a transfection-derived focus.

Comparisons between the normal and EJ tumor DNAs using the cloned oncogene sequence as probe were undertaken. DNAs of EJ and FS4 origin were treated with the indicated endonucleases prior to Southern analysis using the plasmid-borne 6.6 kb sub-clone as probe. BamHI digested FS4 and EJ DNAs; XbaI and BamHI doubly digested FS4 and EJ DNAs; KpnI and BamHI doubly digested FS4 and EJ DNAs; SacI and BamHI doubly digested FS4 and EJ DNAs. These data revealed no difference between the following restriction sites which surround or are embedded within the gene: EcoRI, BamHI, SacI, KpnI, XbaI and PvuII. Thus, any differences between the normal sequence and its transforming counterpart are subtle and elude detection by such rough structural analyses.

EXAMPLE 8

Relation of the EJ Transforming Gene to Other Tumor Transforming Genes

1° and 2° foci were induced by transfection of DNAs from a variety of human tumor cell lines. Cultures were expanded from these foci and their DNAs analyzed in the Southern procedure using the 6.6 kb oncogene sub-clone as probe.

Part A. DNAs were treated with endonuclease BamHI prior to Southern analysis. Sequence hybridization was performed at low stringency (35% formamide). DNAs analyzed were prepared-from (a) SW-2-2, a 2° transfectant induced by DNA of SW480, a human colon adenocarcinoma cell line; (b) Lx1-2, a 1° transfectant induced by DNA of Lx1, a human small cell lung carcinoma cell line; (c) A549-1, a 1° transfectant, induced by DNA of A549 human lung adenocarcinoma cell line; (d) EJ-6-2, a 2° transfectant, induced by DNA of EJ human bladder carcinoma cell line; (e) SH-1-1, a 2° transfectant induced by DNA of SK-N-SH, a human neuroblastoma cell line; (f) T24-8-5, a 2° transfectant induced by DNA of T24 human bladder carcinoma cell line; and (g) HL60-1-6, a 2° transfectant induced by DNA of HL60 human promyelocytic leukemia cell line.

Part B. DNAs were treated with endonuclease EcoRI before Southern analysis. Sequence hybridization was performed at high stringency conditions (50% formamide). DNAs were from independent 1° and 2° foci induced by passing the transforming sequence of the T24 human bladder carcinoma cell line. These foci were termed T24-8, T24-7, T24-6, T24-5, T24-8-2 and T24-8-5.

The cloned probe detected a newly acquired 6.6 kb segment in cells transfected with EJ-bladder carcinoma DNA. This positive control demonstrated the reactivity of the cloned probe with the transfected gene from which it was derived. In contrast the probe was not reactive with DNA of cells which had acquired oncogenic sequences from the following human tumor cell lines: colonic adenocarcinoma, small cell lung carcinoma, lung adenocarcinoma, neuroblastoma, and promyelocytic leukemia, even at low stringency conditions.

An exception to this group of negative correlations was the detection of a novel DNA fragment in mouse cells transfected with the T24 human bladder carcinoma sequences. It had previously been found that a DNA of this cell line to be active in focus induction. The present result indicated that the oncogenic sequence of this tumor cell line was either structurally related or extremely closely linked to the oncogene of the EJ bladder carcinoma cell line.

Further analysis of the DNAs of the primary and secondary transfectants induced by passing the T24 bladder carcinoma sequence indicated that they all carried a DNA fragment reactive with the EJ bladder carcinoma probe, and that the sizes of these fragments were reminiscent of those seen in EJ-derived transfectants. In both cases, a single high molecular weight EcoRI segment was seen, a pattern which was distinct from that seen with a variety of other types of human oncogenes. See Murray, M. J. et al., *Cell* 25:355–361 (1981). Since the two oncogenic sequences appear to be resistant or sensitive to inactivation by the same restriction enzymes, it appears that the two oncogenes derived from activation of the same normal cellular sequence. This suggests that all tumors of a given type carry the same, tissue-specific oncogene.

EXAMPLE 9

Activation and Characterization of the Rat Neu Oncogene

The Neu Gene Family

Exposure of perinatal BDIX rats to a single dose of the alkylating agent ethylnitrosourea leads to a high incidence of neuroectodermal tumors. Rajewsky, M. F. et al., In: *Origins of Human Cancer*, Cold Spring Harbor Laboratory, 709–726 (1977); Rajewsky, M. F., In: *Recent Results in Cancer Research* 84:63–76 (1983). Up to 95% of animals mutagenized transplacentally after the fifteenth day of gestation or injected directly with ethylnitrosourea up to ten days after birth will develop central and peripheral nervous system tumors after a dose- and strain-dependent latency time. These tumors and the cell lines derived from these tumors display the characteristics of a wide variety of neural and glial cell types. Schubert, D., *Nature*, 249:224–227 (1974).

DNA isolated from four independently derived tumor cell lines of this type contains activated oncogenes which can be detected in an NIH 3T3 focus forming assay. The majority of oncogenes detected in this assay have been shown to be genetically altered versions of one of the three closely related ras genes. (Varmus, 1984). However, the gene transferred from these neuro/gliobastomas is unrelated to the ras genes and has been designated neu.

Neu was first recognized to be a distinct gene by its association with the 185,000 dalton tumor antigen, p185, which is displayed on the surface of transfected cells. Neu is related in DNA sequence to the erbB gene, which encodes the epidermal growth factor (EGF) receptor, and antisera raised against the EGF receptor show some cross-reactivity with p185. However, detailed analysis has shown that neu bears only limited homology to erbB and that the two genes reside on different chromosomes. Schechter, A. L. et al., *Science*, 229:976–978 (1985). Thus, the neu gene is related to, but distinct from, the gene which encodes the EGF receptor.

cDNA clones of the neu oncogene have been isolated from cell lines transformed by this gene. Bargmann, C. I. et al., *Nature*, 319:226–230 (1986). Human versions of the same gene have also been isolated and termed variously c-erbB2 or HER2. The DNA sequences of these rat and human clones predict a 1260 amino acid protein product of the neu gene which is colinear with and 50% identical to the predicted amino acid sequence of the EGF receptor. By analogy to the EGF receptor, the neu product appears to be a transmembrane protein consisting of a cysteine-rich extracellular region of 650 amino acids, a transmembrane domain, and an intracellular portion of 580 amino acids consisting in part of a tyrosine kinase domain.

Biochemical studies of the p185 protein support these conclusions. p185 is glycosylated and accessible to antisera in intact cells, which is consistent with its being localized at the cell surface. It also has an associated tyrosine specific protein kinase activity. p185 does not, however, bind EGF and thus appears to be the receptor for an as yet unidentified growth factor.

Isolation of Clones of Normal and Transforming Alleles of the Rat Neu Gene

Biologically active genomic clones of normal and transforming alleles of the rat neu gene have recently been isolated. Hung, M.-C, et al., *Proceedings of the National Academy of Sciences, U.S.A.*, 83:261–264 (1986). Structural comparison of these clones revealed no evidence of gross rearrangements, suggesting that subtle genetic alterations were responsible for activation of the neu oncogene. Comparable levels of p185 were shown to be expressed in nontransformed cell lines containing the normal allele and in transformed cell lines containing the mutant allele, suggesting that the alteration responsible for the activation of neu did not lead to deregulation of expression of the gene. Such results implicate a transforming lesion within the encoded protein p185, which should be represented in cDNA versions of the gene.

Comparison of cDNA Clones of the Normal Neu Gene and Transforming cDNA Clones

To determine the effect of the alteration responsible for activation of the neu gene, a comparison was made of the previously isolated transforming cDNA clone, DNAs from three other ethylnitrosourea-induced activations of the neu gene and a cDNA clone of the normal allele of neu.

Isolation of a Normal Neu cDNA Clone

It was first necessary to isolate a normal neu cDNA clone. To do so, a cDNA library was constructed using RNA from the cell line DHFR G8. Hung, M.-C., et al., *Proceedings of the National Academy of Sciences, U.S.A.*, 83:261–264 (1986). The DHFR cell line was made by transfecting a genomic cosmid clone containing a complete normal neu gene from the BDIX strain of rat into NIH 3T3 cells. These cells express high levels of the neu gene product, p185, and a high level of the neu RNA transcribed from the transfected gene. cDNA clones were made by the S1 snapback technique, tailed with dCTP using terminal transferase, and inserted into dG-tailed pBR322 at the PstI site. Thirty recombinant plasmids reactive with neu probes were isolated.

These plasmid clones were compared by restriction mapping to a full length cDNA clone of an activated neu oncogene. While these normal cDNA clones have common sequences with the previously identified transforming cDNA clones, none contained the entire coding region of neu. A clone containing the entirety of the neu coding region was constructed, however, by in vitro recombination of two partial, overlapping clones which share a unique NaeI site. The 5' end of the resulting clone was sequenced to verify the presence of the initiation codon for the neu-encoded p185 protein.

Figure 12:
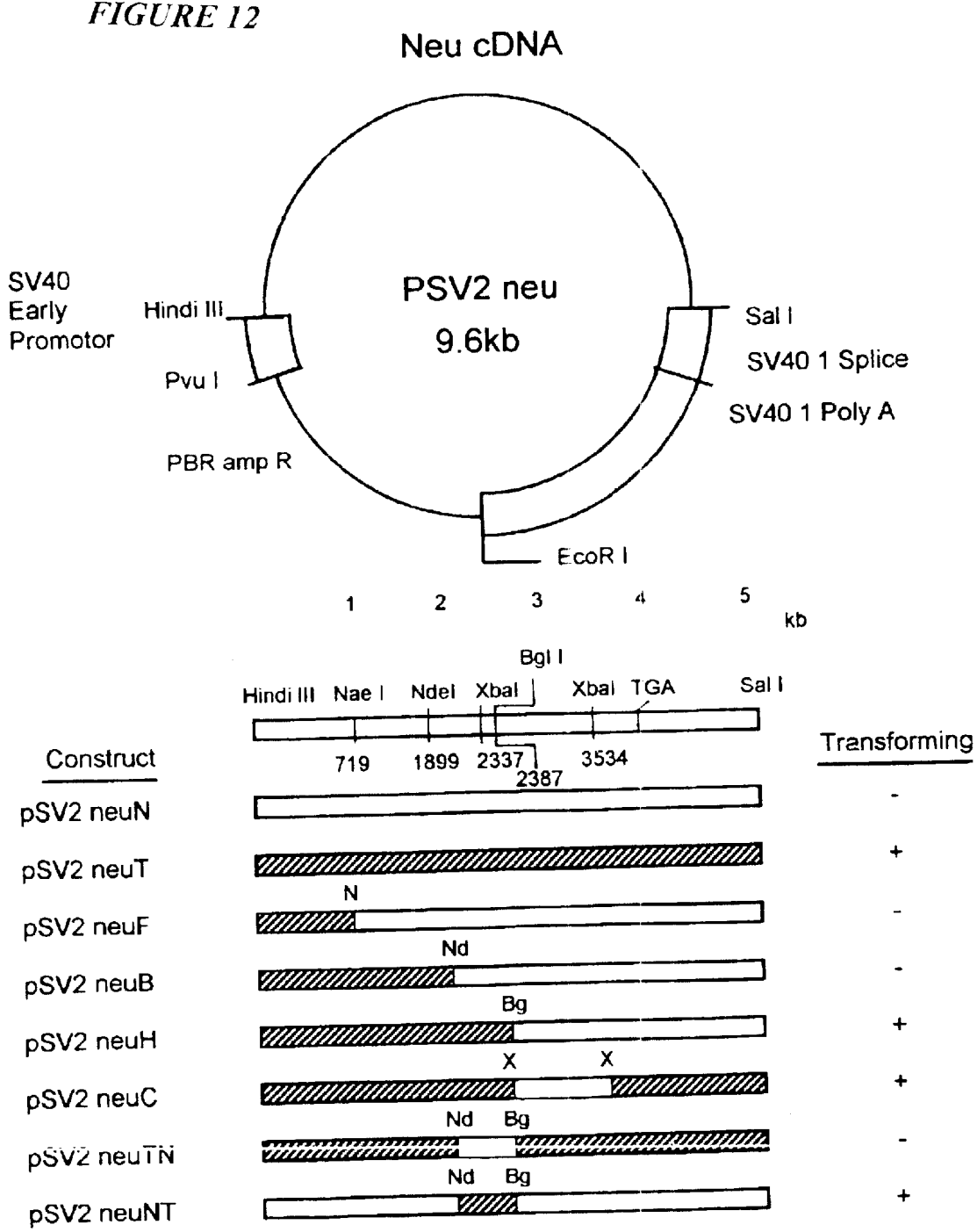
FIG. 12 is a schematic representation of pSV2neu, created by inserting the neu gene cDNA indicated into the pSV2 expression vector.

This normal neu clone was inserted into the pSV2 expression vector to create pSV2neuN, as shown in FIG. 12. Mulligan, R. C. et al., *Nature*, 277: 108–114 (1979). A transforming neu cDNA clone derived from the B104-1-1 cell line, which is a secondary transfectant of an activated rat neu gene, was inserted into pSV2 to create a plasmid designated as pSV2neuT (FIG. 1). pSV2neuT was highly active in a focus-forming assay on, NIH 3T3 cells or Rat 1 fibroblasts. This assay measures the ability of DNA molecules that have been introduced into cells by the transfection to convert such cells, growing in monolayer culture to a transformed state, causing descendants of these cells to form a cluster or focus of morphologically transformed cells in an area of the cell monolayer. However, when the normal neu cDNA, also inserted into the pSV2 vector, was transfected into NIH 3T3 cells using identical conditions, no foci were observed.

Comparison of p185 Production by Transformed and Non-transformed Cells

Cell lines containing the pSV2neuN or pSV2neuT plasmids were isolated by cotransfection with pSV2neo (referred to hereafter as the neo-r marker) and selection of G418. Southern, P. J. and P. Berg, *Journal of Molecular and Applied Genetics*, 1:327–341 (1982). Cell lines expressing the pSV2neuT construct were morphologically transformed and refractile; those containing pSV2neuN were flat and nontransformed in morphology. These cell lines were metabolically labeled with $^{32}$P orthophosphate and their lysates incubated with a monoclonal antibody that specifically precipitates the rat neu gene product. As shown in FIG. 13, lanes c, d, and i, the levels of labeled p185 were comparable in the transformed and nontransformed cells. These results are consistent with earlier work suggesting that neu has been activated by a mutation in the coding region of the gene rather than one which deregulates expression. Hung, M.-C. et al., *Proceedings of the National Academy of Sciences, U.S.A.*, 83:261–264 (1986).

Identification of the DNA Sequences Responsible for Neu Gene Activation

Identification of sequences responsible for the transforming activity of the pSV2neuT clone was carried out by using recombinants between this clone and the pSV2neuN clone-carrying the normal allele. The recombinants were constructed by ligation of appropriate cloned DNA segments. FIG. 12 shows the structure of a series of clones which delineate the region of neu that carries the activating mutation. The structure of each recombinant clone shown was verified by restriction mapping. In each case, at least two independent plasmid isolates were tested for the ability to morphologically transform NIH 3T3 cells. All recombinant clones were cotransfected with the neo-r marker and the morphology of the resulting G418-resistant colonies was scored. Morphologically nontransformed colonies were tested to ensure that they were expressing structurally intact p185 protein from the acquired cDNA clones.

Clones pSV2neuF and pSV2neuB, which contain the first 719 and 1899 nucleotides, respectively, of the transforming clone fused to the remaining sequences of the normal clone (FIG. 12), were not transforming, although they did direct the synthesis of p185. Clone pSV2neuH, which contained transforming neu sequences from the 5' end of the gene up to nucleotide 2387 and normal neu sequences thereafter, gave foci upon transfection and yielded transformed colonies indistinguishable from those generated by the parental pSV2neuT clone. pSV2neuC was also transforming. It contained an XbaI fragment from nucleotide 2337 to nucleotide 3534 of the normal neu gene, which replaced the corresponding portion of the transforming cDNA. These results indicate that the normal cDNA and the transforming cDNA differ in a sequence between nucleotides 1899 and 2337 and that the presence of this sequence in the transforming clone is necessary for transformation.

In order to prove that this sequences is also sufficient for transformation, the reciprocal constructs pSV2neuTN and pSV2neuNT (FIG. 12) were constructed and tested by transfection into NIH 3T3 cells and Rat 1 fibroblasts. pSV2neuTN contained the entire transforming cDNA with the exception of nucleotides 1899 to 2387, defined by NdeI and BglI sites, which are derived from the normal neu clone. pSV2neuNT contained the entire normal neu cDNA sequence except for the corresponding 488 nucleotides, which were replaced by those from the transforming clone. In parallel experiments, pSV2neuNT gave comparable numbers of foci to pSV2neuT, the parental transforming clone; pSV2neuTN, pSV2neuN, and mock transfected controls yielded no foci. These experiments demonstrate that the essential genetic differences between the normal and transforming clones reside within this 488 nucleotide fragment.

Figure 13A:
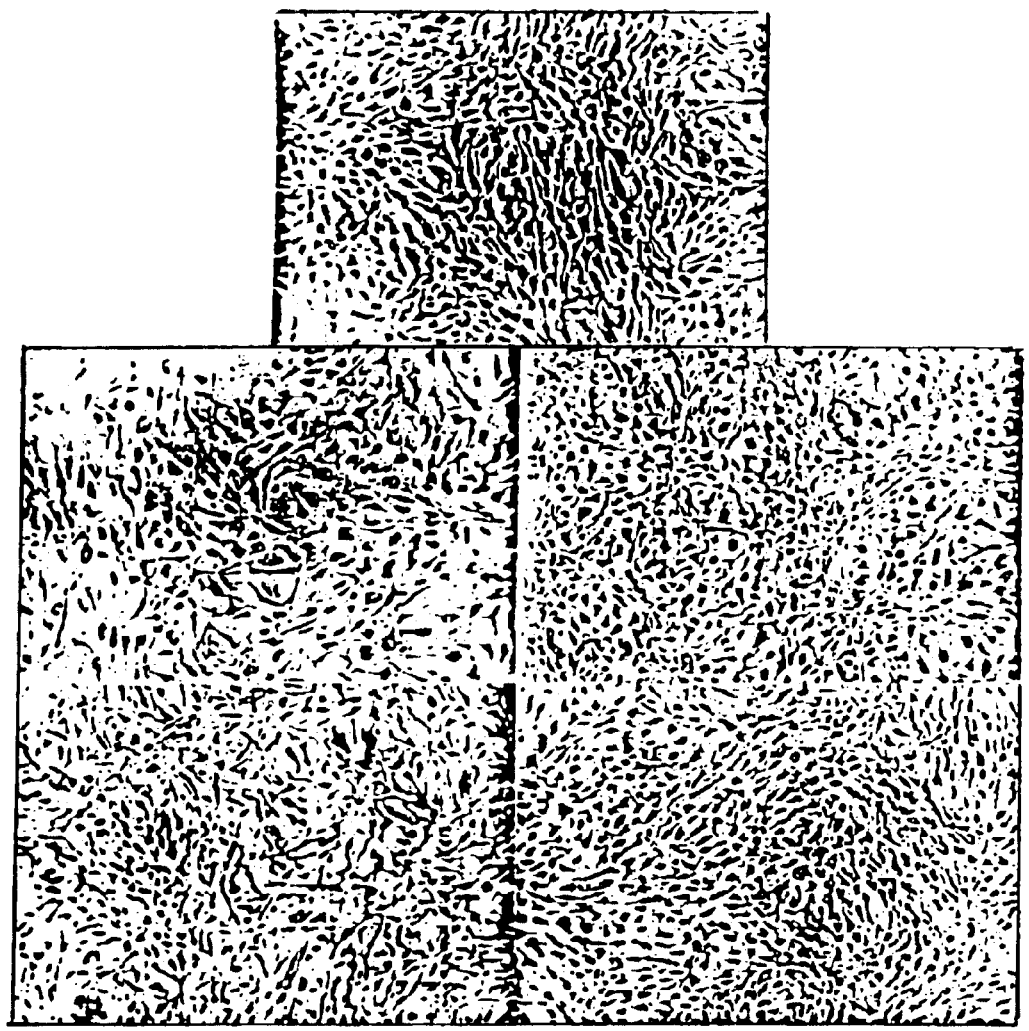
FIG. 13 presents electrophoretic gel patterns characteristic of cell lines containing pSV2neu constructions.
Figure 13B:
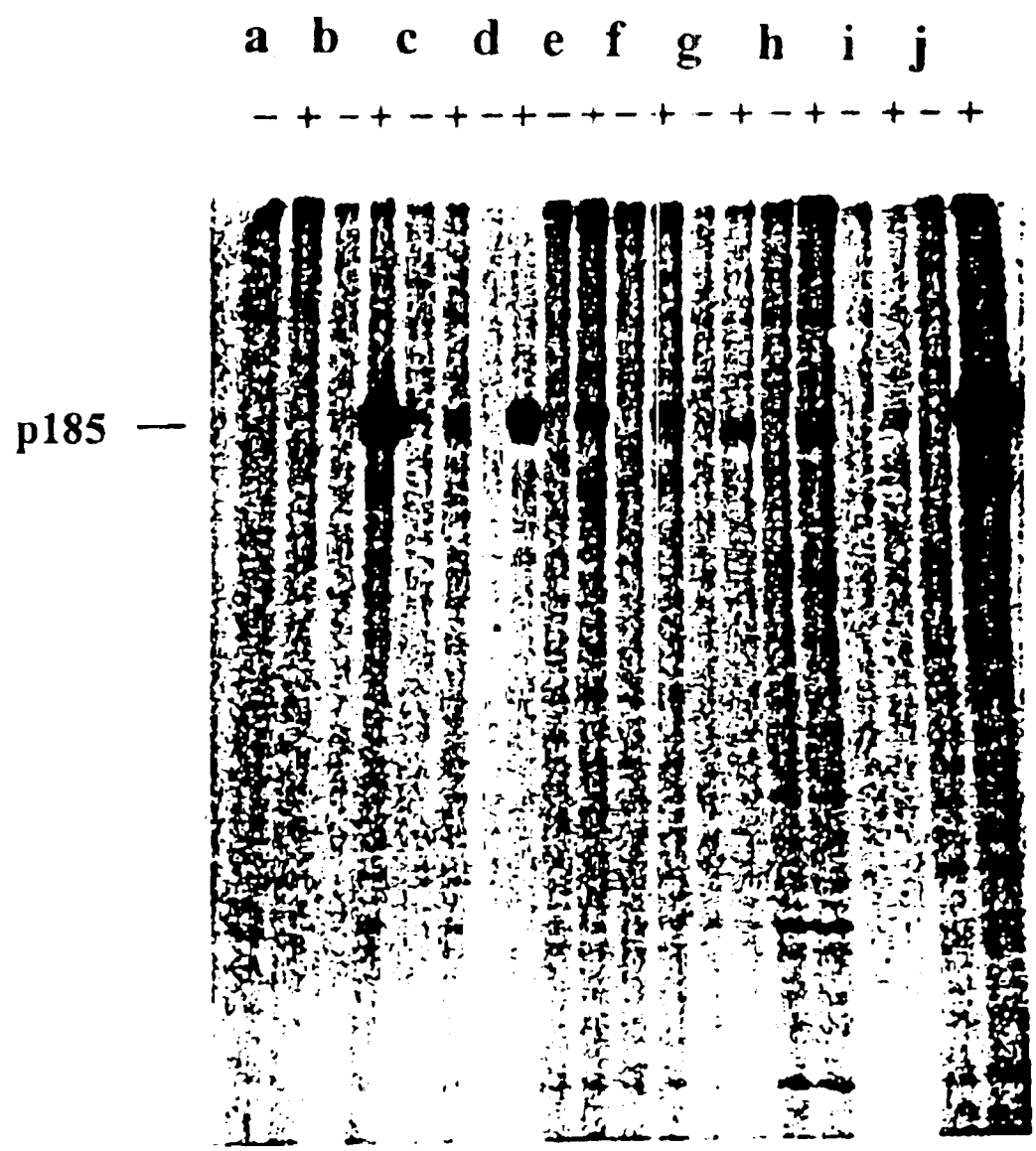

The data shown in FIG. 13 support these conclusions. G418-resistant cell lines isolated by cotransfection of the pSV2neu plasmids and the selectable neo-r gene are shown in FIG. 13A. Lines containing pSV2neuTN or pSV2neuN are morphologically flat and indistinguishable from lines transfected with the neo-r gene alone. In contrast, cells containing pSV2neuNT and pSV2neuT are highly refactile and very similar to one another in morphology. These cell lines were metabolically labeled with $^{32}$P-orthophosphate and the resulting lysates incubated with anti-p185 monoclonal antibody 16.4. Drebin, J. A. et al;, *Nature*, 312:545–548 (1984). FIG. 13B shows the levels of p185 expressed in representative cell lines containing pSV2neuN (lanes c and d), pSV2neuT (lane i), pSV2neuTN (lanes e and f), and pSV2neuNT (lanes g and h). Lysates from DHFR G8 and B104-1-1 cells (lanes b and j), the cells lines from which the normal and transforming cDNAs were isolated, were also analyzed. Although individual cell clones show a wide range of p185 levels, it is clear that there are similar ranges of p185 expression in both the normal and transformed cells. No p185 is found in lines transfected with the neo-r marker clone alone (lane a). Thus, the differences in these cells must be accounted for by intrinsic differences in the properties of the p185 proteins that they express.

Definition of the Mutation Distinguishing the Normal Neu Allele and the Activated Neu Gene The complete DNA sequence of the coding region of the transforming neu cDNA has been determined. Bargmann, C. I. et al., *Nature*, 319:226–230 (1986). To define the precise mutation that distinguishes the two alleles, the DNA sequence of the region between nucleotides 1899 and 2387 was determined for the normal neu cDNA. Only a single difference was found between this sequence and that previously determined for the transforming clone. At nucleotide position. 1012 there is an A in the oncogene clone, while the normal clone carries a T in this position. As a result, the predicted amino acid present at residue 664 of the encoded p185 is affected; a valine found in the normal protein is replaced by a glutamic acid in the oncogenic version. FIG. 14 shows the DNA and predicted amino acid sequence of nucleotides 1968 to 2073 for both the normal neu gene and the transforming neu gene. The presumed mutation falls within the putative transmembrane domain of the neu gene product, p185.

Genomic clones of normal and transforming alleles of neu have been previously isolated. These clones were used to independently verify the nucleotide difference seen in the cDNAs. Such corroborative data served to exclude the possibility that the observed difference in the cDNAs arose during cDNA cloning. Sequencing of subclones of the genomic versions of the two alleles confirmed that the same T to A substitution was present in these genomic clones. This indicates that the mutation, a T to A transversion, arose somatically during creation of the B104 neuroblastoma tumor or cell line.

Determination of Activation of Independent Neu Oncogenes

Earlier results had shown that DNAs prepared from four out of six neuro/gliobastoma cell lines displayed activated neu oncogenes in a NIH 3T3 focus assay. Shih, C. et al.:

*Nature*, 290:261–264 (1981). These six cell lines had been derived by transplacental mutagenesis of BDIX rat embryos with ethylnitrosourea. These independent activated neu genes were evaluated to see if they contain the same activating mutation. DNAs from transfectants containing these neu genes were hybridized with oligonucleotide probes which would recognize preferentially one or the other allele of the neu gene. This technique has been successful in identifying various activated alleles of ras genes. Bos, J. L. et al., *Nature*, 315:726–730 (1985); Zarbl, J. et al., *Nature*, 315:382–385 (1985).

Oligonucleotides corresponding in sequence either to the wild type or the mutant neu version of the neu gene were synthesized. The sequence of these two 20-mers is given in FIG. 15. These 20-mers were then hybridized under stringent conditions (2 degrees below the calculated $T_m$ of a perfect duplex) to dried agarose gels containing DNAs which had been digested with appropriate restriction endonucleases. The 20-mer corresponding to the wild type sequences hybridized approximately ten times as well to pSV2neuN as it did to pSV2neuT. In contrast, the oligonucleotide whose sequence derived from the transforming allele preferentially hybridized to pSV2neuT by the same factor.

DNA was isolated from transfectants carrying the four independently activated neu oncogenes described above and cleaved with HindIII. The resulting fragments were resolved on a 1% agarose gel. The agarose gels were incubated under conditions identical to those used in analysis of the cloned DNAs described above shown in FIG. 15. DNA from DHFR G8, which contains about 50 copies per genome of the normal genomic neu gene, was included as a control.

FIG. 16A shows hybridization of the transfectant DNAs with the oligonucleotide corresponding to the wild type sequence. A strong signal appears in DHFR G8 DNA, which has introduced copies of the normal neu gene (lane b). Considerably weaker signals can be seen in lanes containing the neu-transformed transfectant DNAs (lanes c–f) and in untransfected NIH 3T3 cells (lane a). FIG. 16B shows an identical gel prepared in parallel probed with the oligonucleotide containing the mutant sequence. DHFR G8 DNA reacts only weakly with this probe (lane b) but all neu-transformed transfectant DNAs (lanes c to f) yield strong signals with this probe. The transfectant DNA shown in lane d has a smaller neu-homologous HindIII fragment than the other transfectants due to truncation of the transfected gene at the 3' end.

A low level of reactivity between the wild type probe and the transfectants is probably due to cross-reactivity of the probe, since it is comparable to the signal seen upon analysis of cloned pSV2neuT DNA with the same probe (compare FIG. 15 lanes b and d with lanes c–f in FIG. 16A and 16B).

In order to control for differences in signal intensity due to DNA loading and transfectant copy number, the gel in 16B was stripped of probe and rehybridized with an oligonucleotide probe from a different part of the neu gene. The transfectant cell lines may contain different copy numbers of the rat neu gene due to variable amplification during the process of transfection. The results of this hybridization are shown in FIG. 16C. Comparison of corresponding lanes in FIGS. 16A, B, and C shows that DNAs of all neu oncogene transfectants exhibit stronger hybridization with the mutant probe than with the wild type probe, and that the extent of their hybridization with the mutant probe correlates well with the copy number of the neu gene present in the various DNAs.

Although these data strongly suggest that all of the activated neu genes studied have alterations at the same nucleotide position, it was not clear whether the mutations involved the same T to A transversion in all cases. A T to G transversion might give the same pattern of hybridization, since it would cause an A/G mismatch with the wild type oligonucleotide and a relatively stable G/T mismatch with the mutant oligonucleotide. To address this possibility, a third 20-mer was synthesized with the sequence shown in FIG. 15. This oligonucleotide was incubated under hybridizing conditions with the gel analyzed in FIG. 16A after the initial probe had been removed. This oligonucleotide did not hybridize preferentially to the transfectant DNAs under stringent conditions (FIG. 16D). Thus, the alteration in each of these activated neu genes is probably the same T to A transversion.

Figures 17A, 17B:
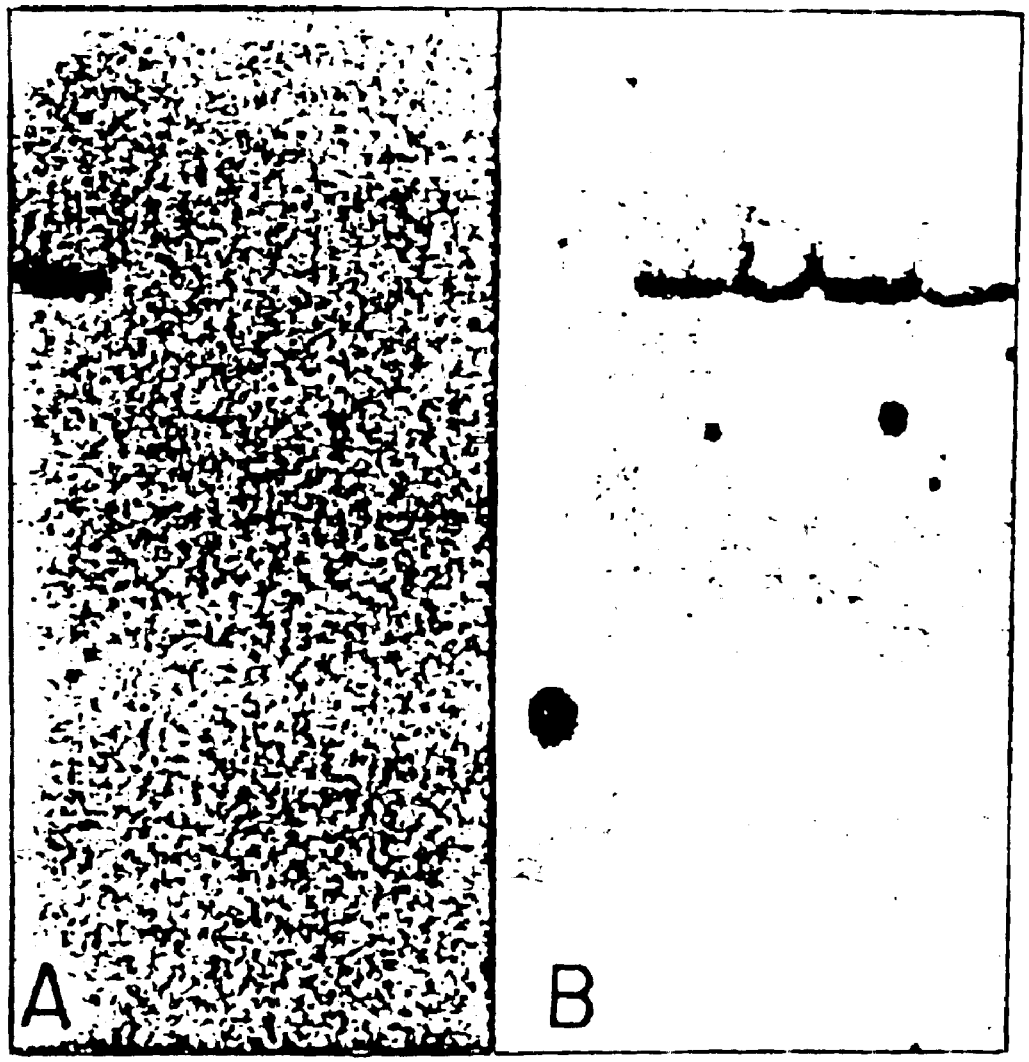
FIG. 17 shows electrophoretic gel patterns after hybridization of DNA from tumor cell lines and normal BDIX DNA with oligonucleotide probes.

That the point mutation was generated during tumorigenesis and thus did not reflect preexisting polymorphism in the rat genome or activation during the transfection process was also confirmed. DNA was isolated from BDIX rat liver and from the four rat tumor cell lines which were derived from BDIX rats and yielded activated neu genes in a transfection assay. Duplicate gels were probed either with the wild type or the mutant oligonucleotide (FIG. 17). BDIX liver DNA reacts well with the wild type but not with the mutant oligonucleotide (FIG. 17, lanes a and f). In contrast, the four tumor cell lines react only with the mutant oligonucleotide (FIG. 17, lanes b–e and i–l). This demonstrates that the T to A transversion at nucleotide 2012 arose in the generation of the tumor or tumor cell lines. It also seems that the tumor cell lines are hemizygous or homozygous for the activated allele of the neu gene. Loss of the normal allele may have occurred during tumorigenesis or in passage of the tumor cell lines. A similar loss or under-expression of the normal ras alleles has been observed in several tumors and tumor cell lines that contain oncogenic versions of these ras genes. Capon, et al. *Nature*, 304:507–513 (1983): Guerrero, I et al., *Proceedings of the National Academy of Sciences, U.S.A.*, 82:7810–7814 (1985).

Multiple Independent Activations of Neu

Chemical carcinogenesis, though provoked by apparently randomly acting agents, often results in specific genetic changes in the resulting tumor cells. Neu appears to be activated by the same nucleotide change in each of the four of the transforming neu alleles analyzed. Each of these alleles was isolated from a neuro- or glioblastoma that arose from transplacental exposure to the alkylating agent ethylnitrosourea. Schubert, D. et al., *Nature*, 249:224–227 (1974). Neu is also activated at the same residue in four independent nervous system tumors induced by the related alkylating agent methylnitrosourea.

Similarly, extensive study of methylnitrosoureainduced mammary carcinogenesis in Buf/N rats has shown that among nearly 100 independent resulting tumors, all contain H-ras oncogenes activated by the identical G to A transition at residue 35. Sukumar, S. et al., *Nature*, 306:658–661 (1983); Zarbl, H. et al., *Nature*, 315:382–385 (1985). Other examples of specificity of activation include dimethylbenzanthracene-induced papillomas with activated H-ras genes in genetically susceptible Sencar mice and thymic lymphomas induced by gamma irradiation or methylnitrosourea, which yield transfectable K-ras and N-ras oncogenes, respectively. Balmain, A. and I. A. Pragnell, *Nature*, 303:72–74 (1983); Guerrero, I. et al., *Proceedings of the National Academy of Sciences, U.S.A.*, 81: 202–205 (1984). The K-ras oncogenes detected in the former case appear to have the same activating mutation in at least three out of four tumors examined. It is interesting to note that the administration of the same mutagen, methylnitrosourea, under different conditions leads to the specific activation of H-ras in mammary tumors, N-ras in thymic lymphomas, and neu in neurectodermal tumors. Guerrero, I. et al., *Science*, 225:1159–1162 (1984).

The carcinogen which induces each of these tumors must initially inflict widespread damage to the cellular DNA. The final mutation detected is, however, highly specific. Clearly, strong biological forces must act during multistep carcinogenesis to select the outgrowth of cells bearing the genetic lesions observed in the ensuing tumors. It appears that only a small proportion of cellular genes can be converted into biologically active oncogenes. Within one of these genes, only a few of many possible mutations will yield an actively transforming oncogene. The relatively rare mutations which do generate oncogenes are enriched first because they must confer a selective advantage to the tumor, and later because they can be detected in the focus-forming assay.

The repeated appearance of a specific lesion in one tumor type suggests the presence of additional forces selecting among the possible activating mutations. The nature of the activating mutation must be strongly influenced by the chemical reactivities of the carcinogen. For example, different mutagens used to induce thymomas lead to different activated genes in the resulting tumors. Similarly, mammary carcinomas induced by dimethylbenzanthracene contain a different specific alteration from those induced by methylnitrosourea.

The reactivity of ethylnitrosourea, the agent which induced the described neuroblastomas, allows it to form a number of different adducts in DNA. Singer, B. and J. T. Kusmierek, *Annual Review of Biochemistry*, 52:655–693 (1982). Among these, an adduct causing G to A transition mutations is well described. Rajewsky, M. F., *Recent Results in Cancer Research*, 84:63–76 (1983). Such mutations have been found repeatedly as the activating lesions in the H-ras oncogenes of mammary carcinomas induced by the related carcinogen methylnitrosourea. Zarbl, H. et al., *Nature*, 315:382–385 (1985). The presently described mutations are, however, T to A transversions, the creation of which must be explained by alternative mechanisms involving another one of the many adducts formed after administration of these alkylating agents. This type of mutation is not without precedent: two other ethylnitrosourea-induced mutations isolated after germ-line mutagenesis of mice has also been shown to be T to A transversions. Popp, R. A. et al., *Genetics*, 105: 157–167 (1983); Lewis, S. E. et al., *Proceedings of the National Academy of Sciences, U.S.A.*, 82:5829–5831 (1985). An N-ras oncogene isolated from a methylnitrosourea-induced lymphoma has been found to be activated by a C to A transversion suggesting that several different adducts induced by alkylating agents can lead to mutations. Guerrero, I. et al., *Proceedings of the National Academy of Sciences, U.S.A.*, 82:7810–7814 (1985).

Identifying the Activation Mutation in Human Neu Genes

Examination of Tumor DNAs From Buffalo Rats With Oligonucleotide Probes Homologous to the Neu Gene.

Sukumar and Barbacid (National Cancer Institute, Bethesda) have isolated ten methylnitrosourea-induced nervous system tumors of Buffalo rats which contain activated neu genes. Transfectants which arose from these tumor DNAs were assessed to determine whether the mutation in these neu genes was identical to that found in the tumors previously described.

This was carried out in the following manner; Fourteen transfectants containing ten independent activated neu genes are shown in FIG. 18 (tracks 1–14). Duplicate gels were probed with the oligonucleotide probes described above. That is, they were probed either with the normal oligonucleotide (FIG. 18, top) or the oligonucleotide corresponding to the transforming gene (FIG. 18, bottom). NIH DNA (track N), DHFR G8 DNA (track G) (high copy of the normal neu gene0, B104-1-1 DNA (track B) (high copy of the transforming neu gene) and two Buffalo rat tumors which do not contain active neu genes (tracks c1 and c2) were included as controls. All of the tranfected neu genes bore the identical alteration as that in B104-1-1 DNA, the cell line from which the transforming neu cDNA clone described above was derived. Based on their differential hybridization to the oligonucleotide corresponding to the transforming gene, the transfected neu genes are presumed to have the same sequence change as the B104-1-1 neu gene. These results provide ten independent examples of activated neu genes detected with the oligonucleotide; demonstrate that a second mutagen, methylnitrosourea, leads to the activation of neu genes at this position in a similar way as ethylnitrosourea; and demonstrate that activated neu genes arise in Buffalo rats as well as BDIX rats.

Oligonucleotide-directed Mutagenesis

Oligonucleotide-directed mutagenesis was used to substitute a glutamine residue for the valine residue normally found at amino acid position 664. When this mutated neu gene was inserted into an expression vector and transfected into or infected into recipient cells, 100% of the stable cell lines generated were transformed. (In contrast, 0.1% of recipient cells transformed with the normal neu gene (protooncogene), which encodes a protein including a value residue at amino acid position 664, were transformed.) Thus, like glutamic acid, glutamine at position 664 leads to generation of a transforming neu gene, and mutations detected with an oligonucleotide probe that would recognize glutamine would be presumed to be transforming mutations. Substitution of an aspartic acid residue at position 664, followed by transfection or infection into nontransformed cells, led to the transformed phenotype in 2–3% of the recipient cells. This appears to represent a weakly transforming allele of the neu gene, whose overexpression must be coupled to the mutation for transformation to occur.

Although the discussion to this point, as well as the experimental work described, has been related to the point mutation responsible for activation of the rat neu oncogene, it is possible to use the same approach in identifying the corresponding activation mutation in human neu genes and in detecting the presence of a neu oncogene (or its corresponding proto-oncogene) in human tumor cell DNAs. For example, oligonucleotide probes can be constructed which are specifically reactive with the region of a human neu gene which corresponds to the region shown to contain the point mutation responsible for the activation of the rat neu oncogene. An example of a probe which can be constructed is one based on a single nucleotide difference between a neu oncogene and its proto-oncogene, this single nucleotide alteration being responsible for conversion of the neu protooncogene into its activated oncogene form. These probes, which can be of any length, but will generally be 15 to 20 nucleotides long, can then be used to analyze a tumor cell genome, to determine whether it carries lesions (mutations) in the neu oncogene and to determine their precise location, as described above for the rat neu oncogenes.

Detecting the Presence of a Neu Oncogene

An assay for detecting carcinogenesis caused by mutation of a neu proto-oncogene into neu oncogene comprises employing a labelled oligonucleotide probe specific for a nucleotide sequence present in (or transcribed from) the proto-oncogene or the oncogene, but not the other. An assay for carcinogenesis in human cells can be performed by isolating DNA from the test cells and contacting the DNA with a labelled polynucleotide probe specific for either an oncogenic or protooncogenic sequence in the DNA and thereafter determining whether the probe hybridizes to the DNA. After being radiolabelled, these probes can be used, for example, in the Southern blot procedure to assess tumor cell DNAs for the occurrence of such point mutations. This type of assay can be used in a clinical context as a diagnostic tool to determine the profile of oncogenes activated in human tumor DNAs. The assay would be highly specific because it is capable of detecting single nucleotide alterations in genes of the neu family, thus providing very definitive information about the tumor cells being assayed.

Reagents for employing these oligonucleotide probes can be assembled into a kit. Thus, a kit might contain, in addition to the probe, one or more buffers, reagents for labelling the probe, reagents employed in Southern or other blots, etc.

Because of the change in amino acid sequence of the product protein encoded by a proto-oncogene from the product encoded by an oncogene, it is possible to detect either by specific serological reagents. The serological reagents can be specific for the normal, neu proto-oncogene-specified amino acid sequence at this site of the protein, or be specific for the altered oncogene-specified amino acid sequence at this site of the protein. Other serological reagents could be employed that are reacted with a region of the protein that is unaltered, and consequently reactive with either normal or abnormal forms of the encoded protein.

Using cloning techniques, significant amounts of the protein encoded for by the normal site of the proto-oncogene, or by the altered site of the oncogene, can be isolated. Such protein segments could be used to produce antibodies by standard antibody production techniques. Thus, for producing polyclonal antibodies, such proteins would be employed to immunize a host, such as a rabbit or a rat, and antibodies to the protein would be collected from serum obtained from the host.

Alternatively, monoclonal antibodies could be produced employing cells which produce antibodies to the protein produced by the isolated gene segment in typical fusion techniques for forming hybridoma cells. Basically, these techniques involve the fusing of the antibody-producing cell with a cell having immortality, such as a myeloma cell, to provide a fused cell hybrid which has immortality and is capable of producing the desired antibody (in this case, an antibody to the normal or altered segment of protein coded for by the isolated gene segment). The hybrid cells are then cultured under conditions conducive to the production of antibody after which antibody is collected from the cell culture medium. Such techniques for producing monoclonal antibodies have been well described in the literature. See, for example, U.S. Pat. Nos. 4,172,124 and 4,196,265, issued to Hilary Koprowski et al., the teachings of which are hereby incorporated by reference.

Cloning of the Human Neu Gene

Figure 19:
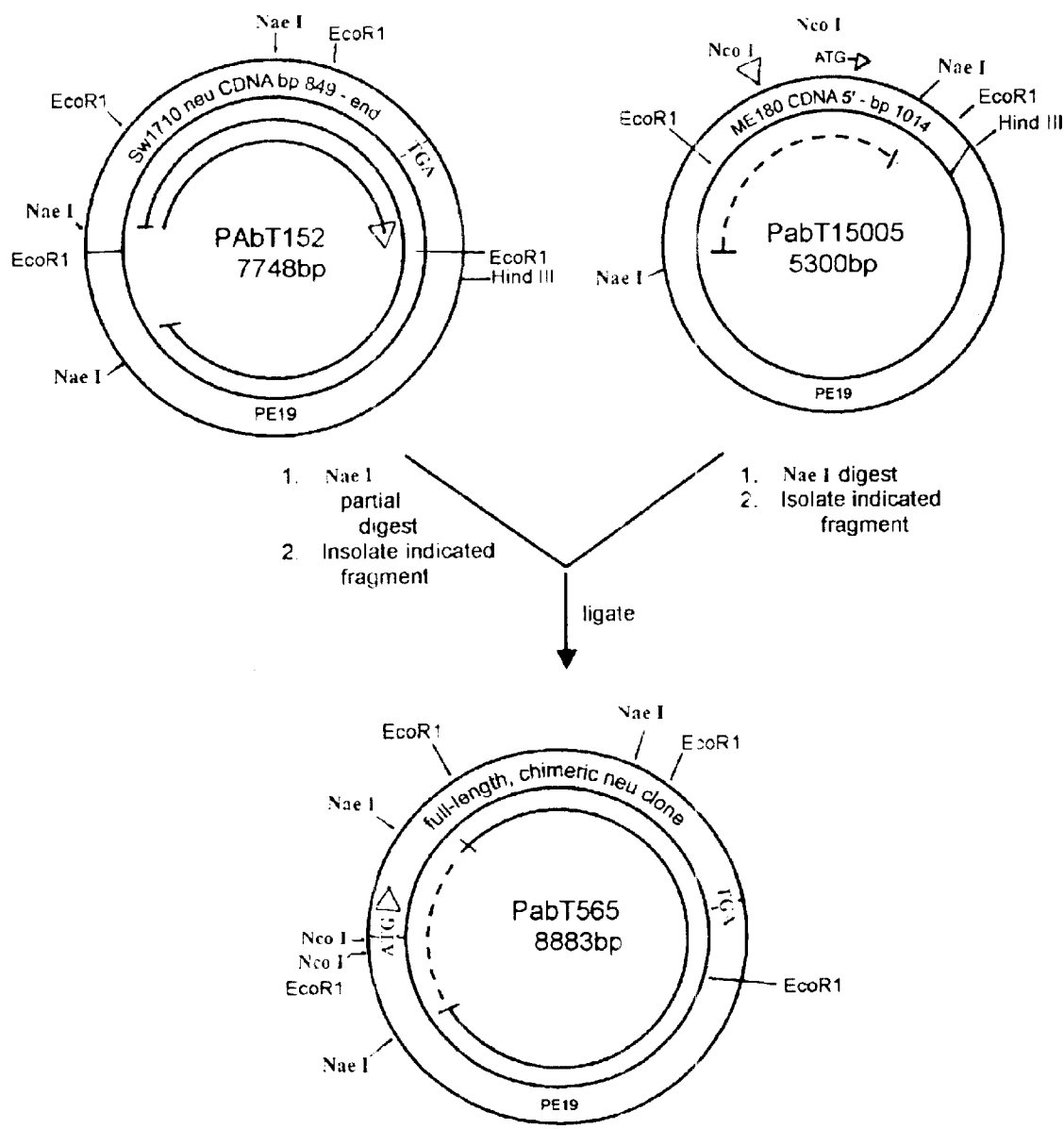
FIG. 19 is a schematic representation of a full length neu cDNA clone constructed from cDNAs of two cervical carcinoma cell lines (ME180 and SW170).

The human neu gene was cloned from two lambda gt11 cDNA libraries derived from poly A+ RNA of two cervical carcinoma cell lines (SW1710, ME180) both of which express high levels of neu RNA. A 1300 bp Pst 1 fragment of the rat neu tyrosine kinase domain was used as the probe to screen the SW1710 cDNA library. Two recombinant plagues were identified as human neu by restriction analysis and partial sequencing. The longer of the two clones contained the majority of the neu coding sequence. The recombinant sequence starts at nucleotide 849 and codes for all but the first 225 of the 1255 amino acids of the neu protein. The missing region of the human neu gene was isolated from the ME180 cDNA library using the 5' Eco R1 fragment, of the SW1710 neu cDNA clone as a probe. The subcloned regions of the two clones and the scheme for the construction of a full length human neu gene are shown in FIG. 19.

Construction of Neu Expression Vectors

The entire neu coding sequence was cloned into the expression vectors pLJ (Roberts, et al., 1985, *J. Virol.*, 56:404–413) and pMax (obtained from Bernard Mathey-Prevot without reservations, shown in FIG. 20). Both these vectors put the neu gene under the transcriptional control of the molony murine leukemia virus promoter and enhancer (LTR). The pLJ vector also expresses $neo^R$ from an SV40 promoter.

Construction of the Transmembrane Point Mutation

Oligo-directed mutagenesis was carried out using the Amersham site-directed mutagenesis kit as per the manufacturers directions and using the following oligonucleotide:

CTGCGGTGG<u>A</u>GGGCATTCTG the underlined nucleotides are different from the normal human neu allele. The presence of the point mutation was determined by differential hybridization and confirmed by sequence analysis using the Promega double stranded sequencing kit as per the manufacturers directions.

Construction of the Truncated Neu Allele

Figure 20:
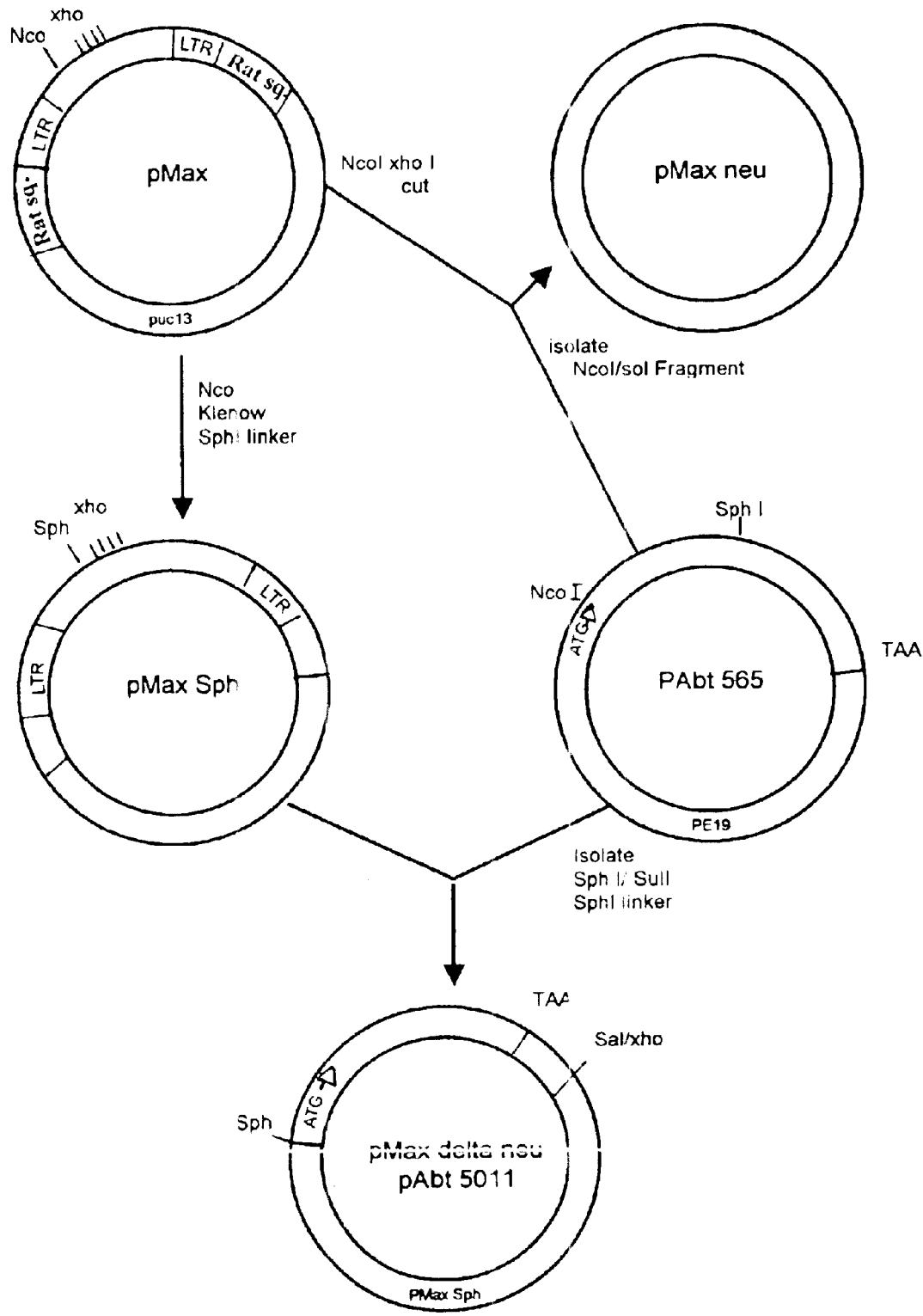
FIG. 20 is a schematic representation of two human neu vectors, pMax neu and pMax delta neu, constructed by inserting the neu gene cDNA indicated into the pMax expression vector, and the pMax-Sph expression vector, respectively.

The pMax vector was restricted with NCO 1, at a unique site in the polylinker, and filled in to create blunt ends with klenow, as shown in FIG. 20. A 12 base pair Sph-I linker (N.E.B. #1115) with the following sequence: CATGCATG-CATG was inserted at this site to generate a unique Sph-I site in the polylinker. This particular linker was chosen because it provides a translation initiation signal (ATG) in all three reading frames. The resulting vector is shown as pMax-Sph in FIG. 20. PMax-Sph was restricted at the Sph-I site and at the Xho-I site (both in the polylinker). A Sph-I/Sal-I 2225 base pair fragment containing the neu cDNA from just 5' of the transmembrane region to the 3' end of the gene was isolated from a plasmid (shown as pAbT 565 in FIG. 20) containing the entire human neu cDNA. The restricted vector and the isolated fragment were ligated together and transformed into the bacterial strain HB101. The resulting plasmid, shown in FIG. 20, has been designated pMax delta neu or pAbT 5011.

Transfection of Cells

Neu expression vectors were transfected into NIH 3T3 cells by the standard calcium phosphate procedure. Briefly, on day 1 cells are plated at $5 \times 10^5$ per 10 cm tissue culture dish. On day 2 the cells are refed and 4 hours later the DNA precipitate is added and the cells are incubated for 6 hrs and refed. The following day the cells are split into G418 containing media and incubated for 10–14 days. NIH 3T3 DNA was used as carrier and pSV-2 neo was used as the selective marker.

Isolation of RNA

Total cellular RNA was isolated by the guanidinium isothiocyanate/CsCl method. When isolating RNA from cells in culture the lysis buffer (4M guanidimium isothiocyanate, 50 mM Tris-HCl pH 7.5, 10 mM EDTA, 0.5% Sarkosyl, 0.1M BME) was added directly to the tissue culture dishes. When frozen tissue was the starting material the tissue was homogenized directly in the lysis buffer with a tissue homogenizer (Biospec Products, INC.). The cellular lysate is then passed through a 18 gauge needle and layered on a 1.2 ml cushion of 5.7 M CsCl in 0.1 M EDTA in a SW50.1 Beckman pollyallomar tube. Centrifuge at 35,000 rpm for at least 12 hours. The RNA pellet is then resuspended in TE containing 1% SDS.

Hybridization Probe

Figure 21:
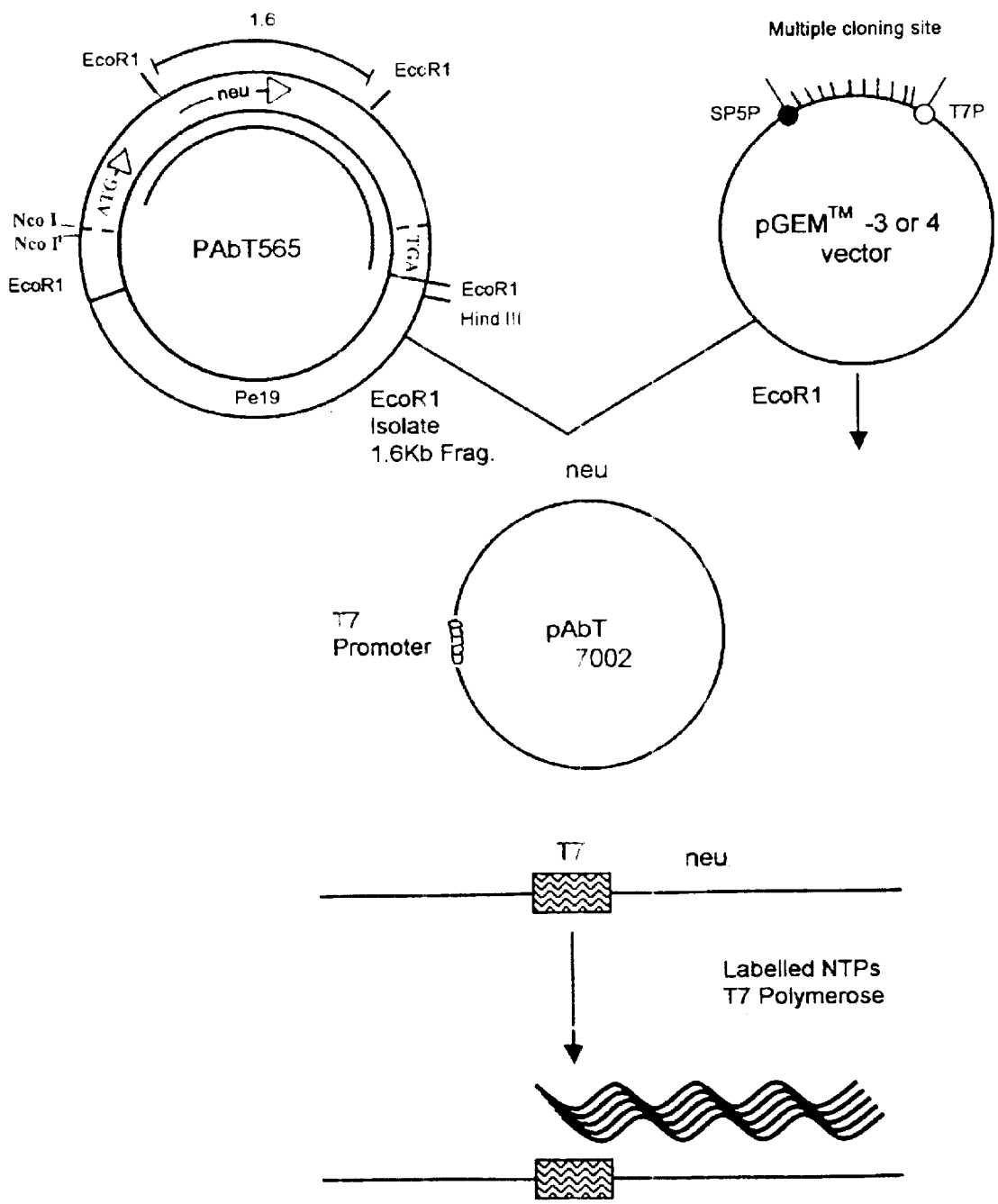
FIG. 21 is a schematic representation of a hybridization probe created by inserting the portion of the neu gene indicated into the pGEM expression vector.

The 1.6 kb Eco RI fragment containing a portion of the extracellular domain, the transmembrane domain and a small portion of the tyrosine kinase domain was subcloned into Promega's pGEM dual transcription vectors as shown in FIG. 21. Labelled RNA transcripts to be used as hybridization probes were generated according to the manufacturers directions.

RNA Slot Blot Analysis

RNA samples were diluted to 1 ug/ml in 6×SSC, 7.4% formaldehyde and heated at 65° C. for 15 min., then placed on ice. The slot blots were done using the S$S slot blot apparatus and the precut BA 85 nitrocellulose sheets supplied according to the manufacturers directions. The filter was prewet with water and then 10×SSC and the RNA was added as a series of 2 fold dilutions starting at 200 ng/slot in a volume of 200 ul. The slots were then washed with 200 ul 10×SSC and the filter was baked for 2 hours at 80° C. in a vacuum oven. The filter was then wet with 10×SSC and prehybridized for 2 hours in hybridization buffer (50% formamide, 5×SSC, 50 mM Sodium Phosphate, 250 ug/ml; salmon sperm DNA, 5×Denhardts). The hybridization solution was then replaced with fresh solution containing 1–2× $10^6$ cpm/ml denatured $^{32}$P labelled RNA probe specific to human neu. The filters were then incubated overnight at 65° C. The following morning the filters were washed 3× in 0.1×SSC, 0.1% SDS for 20 minutes at 80° C.

Cloning of Human Neu Alleles and Testing Transforming Activity

Two cDNA libraries made from cervical carcinoma cell line RNA that express high levels of neu RNA were screened with a probe derived from the tyrosine kinase domain of the rat neu cDNA. Comparison of restriction maps and partial sequence data with published data confirmed the identity of the intact human neu clone constructed from the original isolates from this screen. The human neu cDNA was then transferred into an LTR driven expression vector. Cells transfected with this human neu construct expressed a 185,000 dalton protein that was indistinguishable from the authentic human neu expressed by the human mammary carcinoma cell line, SKBR-3. When this normal human neu clone (pMax neu shown in FIG. 21) was transfected into NIH 3T3 cells they became transformed. This is in direct contrast with the data described for the rat neu gene. In the rat, no matter what the expression level, the normal rat neu allele was not transforming. Expression of the normal human neu gene in other expression vectors which expressed neu at lower levels did not lead to transformation of the NIH 3T3 cells. However, if the human neu gene was mutated so the homologous amino acid to the valine in rat neu was changed to glutamic acid, this gene transformed cells in either expression vector. This indicates, that the mutation activates the transforming activity of the human neu gene. Expression of the truncated human neu allele in either expression vector also transforms NIH 3T3 cells. These results are identical to those reported by Di Fiori, et al. *Science*, 1987; 237:178–182. In summary, both normal and mutated human neu alleles can transform NIH 3T3 cells although much higher expression levels are required for the normal neu.

Analysis of Neu RNA Levels in Human Cell Lines and Mammary Tumors

Total cellular RNA was isolated from a variety of human cell lines and mammary tumors by the guanidium isothiocyanate method. The RNA was then subject to slot blot analysis using a human neu specific probe, the 1.6 kb Eco R1 fragment which contains a portion of the extracellular domain, the transmembrane domain and part of the tyrosine kinase domain. All RNA samples were also hybridized with a alpha tubulin probe to normalize for the amount of RNA present on the filters. The human mammary cell line HBL 100 (ATCC HTB 124) was used as a standard and all results are relative levels as compared to HBL 100. E. Gaffney, *Cell Tissue Res.*, 229:563–568 (1982). The neu expression levels varied from between 1 to 64 times the HBL 100 levels. These results are shown in Table 1.

TABLE 1

Expression Levels of Neu-Specific RNA in Various Cell Lines

|  | Neu Levels |
|---|---|
| Human Cell Lines |  |
| HBL-100 | 1X |
| ME180 | 8X |
| SW1710 | 4X |
| MKN-7 | 32X |
| SK-BR-3 | 64X |
| A-431 | 1–2X |
| BT-483 | 8X |
| Transfected Mouse Line |  |
| 18-3-7 | ++++ |
| NIH3T3 | 1X |

HBL-100 is an epithelial cell line derived from the milk of a nursing mother.
ME180 is a cervical carcinoma cell line.
SW1710 is a cervical carcinoma cell line.
MKN-7 is a gastric cancer cell line.
SK-BR-3 is an adenocarcinoma of the breast.
A-431 is an epidermoid carcinoma cell line.
BT-483 is a ductal carcinoma of the breast.
18-3-7 are NIH3T3 cells transfected with neu.

The results were similar to those previously published (Kraus, et al., *EMBO*, 1987; 6:605–610). We have also analyzed the neu RNA levels in a series of primary human mammary carcinomas. Again we find a wide range of neu expression levels ranging from less than 1 to 128 times the standard, as shown Table 2.

TABLE 2

Quantitation of Neu-Specific RNA levels from Mammary Tumor Samples

|  | Sample | Neu RNA Level |
|---|---|---|
| 1. | 6-8-6-86 | 128 |
| 2. | 8-11-20-86 | 64 |
| 3. | 6-10-15-86 | 16 |
| 4. | 5-11-13-86 | 16 |
| 5. | 9-9-10-86 | 16 |
| 6. | 12-9-12-86 | 8 |
| 7. | 5-10-10-86 | 8 |
| 8. | 8-8-7-86 | 8 |
| 9. | 1-7-7-87 | 8 |
| 10. | 5-9-3-86 | 4 |
| 11. | 4-2-4-87 | 4 |
| 12. | 6-6-12-87 | 2 |
| 13. | 12-12-17-86 | 2 |
| 14. | 13-9-15-86 | 2 |
| 15. | 21-2-27-87 | 2 |
| 16. | 4-12-5-86 | ½ |
| 17. | 11-12-15-86 | ⅛ |
| 18. | 10-1-23-87 | ⅛ |

Hybridization results were determined by serial dilutions of total cellular RNA in dot blot hybridization analysis using the $^{32}$P neu probe. Numbers have been normalized for total RNA amount by hybridization with tubulin probe. Levels are relative to the normal mammary cell line HBL-100 which is set at 1×.

As above, the levels are expressed as relative levels compared to HBL 100 and normalized for tubulin expression.

Production of Neu-specific Monoclonal Antibodies
Production of Hybridomas

The hybridomas described below were generated by immunization of mice with viable cells (the 18-3-7 cell line described below) which express the full length protein encoded by the neu oncogene. This is an important distinction from other approaches for the generation of monoclonal antibodies. Using the full length protein presented by viable cells as the immunogen, it is possible to generate a collection of monoclonal antibodies with specificities that span the entire length of the extracytoplasmic domain of the protein. This is as opposed to the use of peptide immunogens, or short polypeptides generated by prokaryotic systems, which present only a limited number of epitopes from the original protein, and hence raise an immune response of limited specificities. Furthermore, by presenting the protein antigen in its native state, the immune system will be responding to an antigen which most closely resembles that which will be seen when the antibodies are later used for diagnostic or therapeutic applications.

Generation of 18-3-7 Cells 18-3-7 cells are a transfected NIH 3T3 cell line that express full length normal human neu at levels equal to or greater than the human mammary carcinoma cell line, SKBR-3. The human neu gene is expressed by a Murine leukemia virus LTR (promoter and enhancer). This cell line exhibits all the characteristics of transformed NIH 3T3 cells. They grow in soft agar, form tumors in nude mice and display altered morphological characteristics. This cell line was used as the immunogen for the isolation of anti-neu specific monoclonal antibodies.

Figure 22:
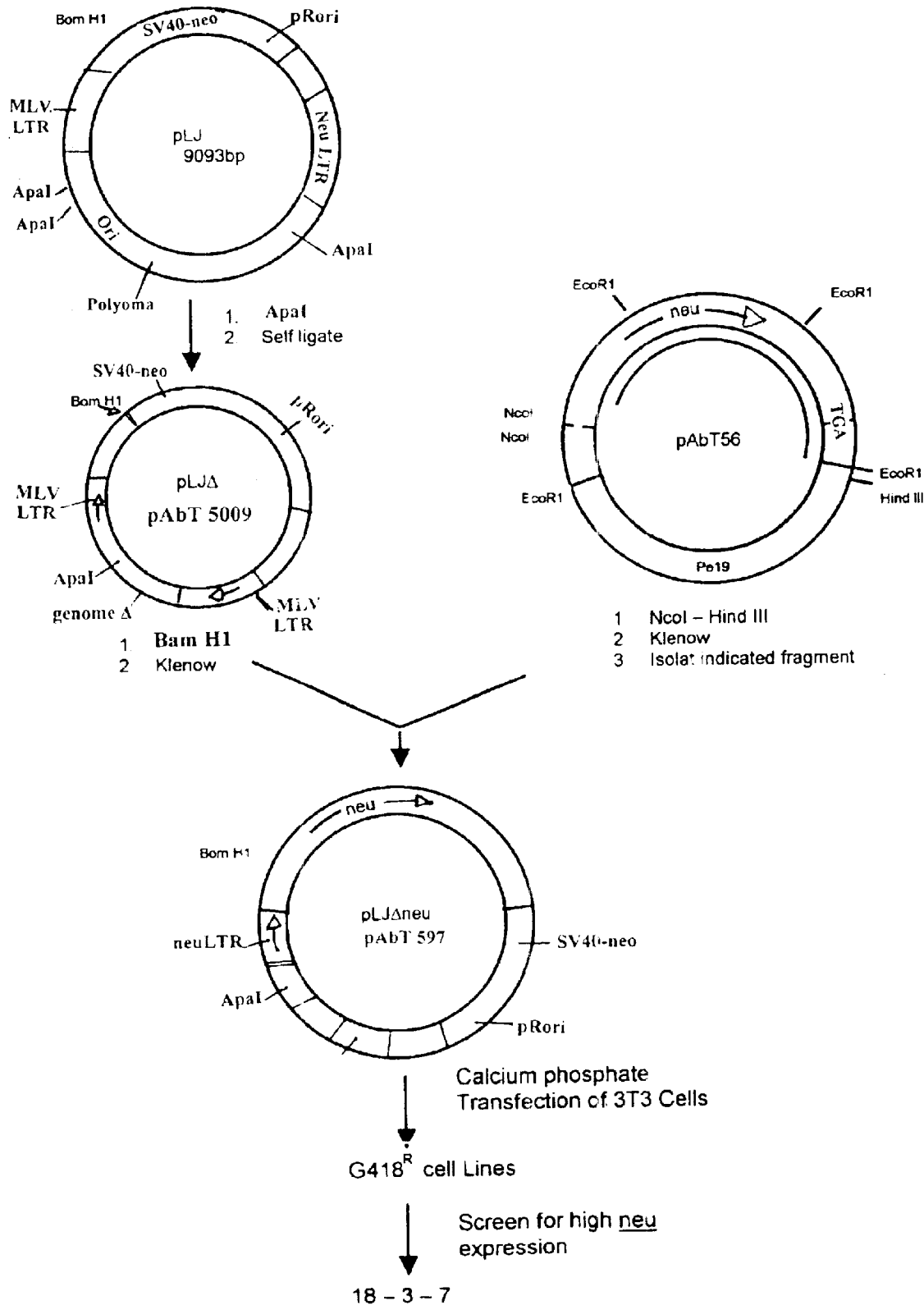
FIG. 22 is a schematic representation of plasmid vector pLJdelta neu, created by inserting the neu gene cDNA indicated into the pLJdelta expression vector.

The pLJ retroviral vector was modified to remove the polyoma early region, thereby eliminating the endogenous transforming activity of the pLJ vector. Construction of the modified vector is shown in FIG. 22. The modification was accomplished by restricting pLJ with Apa I and isolating the 6300 base pair fragment, and recircularizing it with $T_4$ ligase. The resulting plasmid (pdelta LJ or AbT 5009, shown in FIG. 22) was digested at the unique Bam HI site, filled in with Klenow, and ligated to a NcoI-HindIII filled in fragment containing the entire human neu protein coding region. The resulting plasmid (pdelta LT neu or pAbT 577, shown in FIG. 22) was transfected into NIH 3T3 cells by the calcium phosphate precipitation procedure. Transfected cells were selected in G418 (pdelta LJ has a SV40 promoted $neo^R$ gene). The colonies were screened for neu expression by RNA dot blots. 18-3-7 was one of highest expressors out of approximately 50 screened.

Immunization of Mice

Two adult female Balb/c mice were immunized intraperitoneally (I.P.) with $1.4\times10^6$ viable NIH3T3 cells per animal. This was followed immediately by an I.P. injection of cyclophosphamide in $H_2O$, 30 mg/kg. The cyclophosphamide treatment was repeated 24 and 48 hours after the primary injection. On day 14 following immunization, the mice were injected I.P. with $1.5\times10^6$ viable 18-3-7 cells. The animals were allowed to rest for another 14 days, at which time the entire sequence of injecting NIH3T3 cells, cyclophosphamide, and 18-3-7 cells was repeated. Four days following the second injection of 18-3-7 cells, the animals were sacrificed and their spleens obtained for the first fusion. A second, identical experiment was performed, in four female Balb/c mice and four female CB6 (Balb/c X C57BL/6) mice, using $1.8\times10^6$ NIH3T3 cells, and $4.8\times10^6$ 18-3-7 cells per mouse in the first round, and $8.5\times10^6$ NIH3T3 cells and $2.7\times10^6$ 18-3-7 cells in the second round of immunizations.

Hybridoma Methodology

Hybridomas were produced by fusing cells from immunized mice with SP2/O myeloma cells (ATCC CRL 1518) by a polyethylene glycol (PEG) method. Spleens were removed aseptically from immunized mice, and a single cell suspension of the spleen cells was obtained by perfusing the spleen with serum-free media (DME). Spleen cells and SP2/O cells (harvested from a log phase growth culture) were mixed together at a ratio of 5:1, spleen cell:myeloma cell. The cells were centrifuged at 200×g for 10 minutes at 4° C., and the supernatant removed by aspiration. After loosening the cell pellet by gently tapping the bottom of the tube, 1 ml of sterile, 37° C., 10% PEG in DME was added dropwise. The tube was gently swirled while adding the PEG over a 1.5 minute period. An additional 10 ml of 37° C. serum-free DME was then added dropwise, followed by another 20 ml of media. The suspension was then centrifuged at 200×g for 10 minutes at room temperature. Media was aspirated from the cell pellet, and media containing peritoneal macrophages ($2\times10^4$ cells per ml) in the presence of 20% fetal calf serum, 0.2 mM hypoxanthine, 0.4 uM aminopterin, and 0.032 mM thymidine (HAT media) was used to resuspend the cell pellet. (Peritoneal macrophages were obtained from unimmunized mice, either Balb/c or CB6, depending on which spleen cells were used for fusion. These cells were obtained by injecting and immediately removing serum-free media into the peritoneum of euthanized animals.) The post-fusion cells were resuspended to a final cell concentration (not including the peritoneal macrophages) of $5\times10^5$ cells/ml. One milliliter of this cell mixture was distributed to each well of 24 well plates.

ELISA Procedure and Preliminary Screening

Hybridomas which grew after the fusion procedure were initially screened for the secretion of anti-neu antibodies by an ELISA assay on a cell lysate of 18-3-7 cells. Lysates were prepared by incubating freshly harvested 18-3-7 cells in the presence of a hypotonic lysis buffer (10 mM Tris, 10 mM KCl, 5 mM EDTA, pH 8.0) followed by the addition of Triton X 100 to a final concentration of one percent. A lysate of NIH3T3 cells was prepared similarly for use as a negative control. Microtiter plates (Nunc, Immunoplate II) were coated overnight at room temperature with 50 ul of lysate, at a total protein concentration of 500 ug/ml. After aspirating to remove unbound antigen, ELISA's were performed by first incubating 50 ul of culture supernatant obtained from the viable hybridoma colonies in the antigen-coated microtiter wells. A 3 hour incubation at 37° C. was followed by 3 washes with a washing buffer (0.5% Tween 20, 20 mM Tris, pH 7.6) and then a one hour incubation at 37° C. with 50 ul horseradish peroxidase labelled goat anti-mouse IgG+IgA+IgM (HRP-GAM-GAM). The wells were again washed three times with washing buffer, and the assay was developed by the addition of 50 ul of a tetramethylbenzidine (TMB) solution. This solution was prepared by dissolving 10 mg of TMB in 1 ml of dimethlysulfoxide (DMSO), and adding 100 ul of this solution to 5 ml of TMB buffer (0.1 M sodium acetate, to pH 6.0 with 0.1 M citric acid) along with the addition of 10 ul of 3% hydrogen peroxide. Color was allowed to develop for 5 minutes, at which time the enzymatic reaction was stopped by adding 50 ul of 2 N $H_2SO_4$. The optical density (OD) of the resulting yellow color was read at 450 nm on a microtiter plate reader. A positive reaction, as indicated by a greater yellow color developed on 18-3-7 cell-coated wells than on NIH3T3 cell-coated wells, signaled that there was antibody present in the culture supernatant which recognized the neu oncogene product.

Subcloning Hybridomas

Hybridomas which yielded positive results upon initial screening were expanded and cloned by limiting dilution to assure that the cells and resulting antibodies were indeed monoclonal. A feeder cell population was first prepared by obtaining thymocytes from 6 week old unimmunized mice, and making a single cell suspension at a concentration of $2 \times 10^4$ cells/ml in HAT media. Hybridoma colonies which tested positive for the presence of antibody to the neu gene product were diluted in the media containing thymocytes to a concentration of 5 hybridoma cells/ml. Two hundred microliters of this solution was then delivered to each well of 96 well microtiter plates. Once colonies had grown, the supernatants were again tested for the presence of antibody to the neu oncogene product. If the results were positive when tested by the ELISA assay as described above, the colonies were cloned by limiting dilution a second time.

Hybridomas which were obtained in the manner described above following the first fusion secrete monoclonal antibodies which have been designated BD5-2d, TA1-1c, RC1-4c, NA3-6a, and OD3-10j. Following the second fusion, hybridomas were obtained which secrete antibodies named PB3, RC6-2, NB3, ID5, and IB3-4.

Antibody Isotype and Subclass Determination

ELISA assays were performed to determine the isotype and light chain class of the antibody produced by the hybridomas, and to determine the IgG subclass. For this purpose, a kit was purchased from Boehringer Mannheim (Indianapolis, Ind.) which contained all of the necessary immunoreagents. Tissue culture supernatants obtained from the cloned hybridoma colonies were incubated on lysates of 18-3-7 cells as described above. This was followed by an incubation with goat antisera specific for mouse immunoglobulin isotypes, light chain classes, and IgG subclasses, and then with horseradish peroxidase labelled swine anti-goat IgG as the second antibody. The assay was developed using ABTS (2,2'-azino-bis-[3-ethylbenzthiazoline-6-sulfonic acid]) as per the manufacturer's instructions, and the OD of the resulting green color was read at 405 nm.

Using this method, it was determined that 3 of the monoclonal antibodies from the first fusion, BD5-2d, RC1-4c, and TA1-1c, are $IgG_1$/kappa antibodies, and NA3-6a, and OD3-10j are IgM/kappa antibodies. The monoclonal antibodies RC6-2, NB3, ID5, and IB3-4 obtained from the second fusion are $IgG_1$/kappa and the antibody PB3 is $IgG_{2a}$/lambda.

Radioimmunoprecipitation

Immunoprecipitation of radioactively labelled 18-3-7 cells was done using each of the monoclonal antibodies to determine whether the antibodies recognized a protein of 185 kd molecular weight, the expected molecular weight of the neu oncogene product. A near confluent monolayer of 18-3-7 cells (or NIH 3T3) cells in a 10 cm petri dish was incubated overnight in media containing 500 uCi of $^{35}$S-labelled cysteine. The cells were harvested the following morning, and were lysed in a detergent buffer (IP buffer: 1% Triton X-100, 1% sodium deoxycholate, 0.1% SDS, 10 mM Tris, 0.65 M NaCl, pH 7.2) containing the protease inhibitors PMSF and soybean trypson inhibitor. Approximately 1 uCi of the labelled cell preparation was then incubated overnight at 4 C with 500 ul of culture supernatant from each of the hybridomas. During this incubation period, 50 ug of purified rabbit anti-mouse IgG (Kirkegaard & Perry Labs) was mixed with 50 ul of a 1:1 slurry of Protein A-Sepharose (Pharmacia) in IP buffer overnight at 4° C. The excess rabbit antibody was removed by washing the Protein A-Sepharose once with IP buffer, and the slurry was then added to the incubation mixture containing the labelled cells and the monoclonal antibody. This mixture was allowed to react overnight at 4° C. The Protein A-Sepharose was pelleted by centrifugation and was washed four times with IP buffer, followed by one wash with TBS (10 mM Tris, 150 mM NaCl, pH 8.2), and the pellet was allowed to dry. Each pellet was resuspended in 50 ul of sample buffer for SDS gels (10 mM Tris, 4% SDS, 20% glycerol, 10% 2-mercaptoethanol, 0.04% bromphenol blue). One half of each of the samples was run on SDS polyacrylamide gels, using a 4.5% acrylamide stacking gel, and a 7% separating gel. The gels were dried and then autoradiographed.

Results of the immunoprecipitations indicated that all of the monoclonal antibodies recognized a protein of approximately 185 kd molecular weight in the 18-3-7 cells which was not present in the NIH 3T3 cells. This was determined by the presence of a dark band on the autoradiograph which corresponded to the distance travelled in the gel by a 185 kd molecular weight protein as indicated by standard protein markers. A similar experiment was done using SKBR-3 cells (a human breast carcinoma) and A431 cells (a human epidermoid carcinoma). The SKBR-3 cells have been shown by other investigators to express high levels of the human neu oncogene product, and immunoprecipitations with the monoclonal antibodies described above yielded confirming results. The band observed migrated the same distance as the band which was precipitated from the labelled 18-3-7 cells. The A431 cell line, on the other hand, is known to express very high levels of the human epidermal growth factor receptor. (EGFR), which is a 170 kd protein that has significant homology to the human neu oncogene product in the tyrosine kinase domain of the proteins. This is the one protein which might be cross-reactive with the neu gene product if the antibodies recognize the tyrosine kinase region. However, immunoprecipitation of A431 cells with the monoclonals described above showed no reactivity in the area of 185 kd or 170 kd. A control antibody, specific for human EGFR, did react with a protein in the A431 cells, as expected, and the band observed corresponded to 170 kd molecular weight.

Because there was no reactivity with A431 observed when the monoclonal antibodies raised to the 18-3-7 cells were used, it was concluded that the antibodies were specific for the human neu oncogene product, and did not cross react with the human epidermal growth factor receptor.

TA-1 Inhibition of Neu Transformed Cells in Soft Agar

Mouse fibroblasts (NIH3T3 cells) transfected with and expressing high levels of the human neu gene will form colonies in soft agar. This property is directly related to the amount of neu protein and its inherent tyrosine kinase activity. Monoclonal antibodies (MAbs) which recognize the extracellular portion of the human neu protein will cause these proteins to cluster and patch on the cell surface, and then internalize into the cell thereby decreasing the amount of tyrosine kinase activity. We have demonstrated that the addition of the MAb TA-1 to a neu transformed NIH3T3 cell line (17-3-1-3) growing in soft agar will decrease the number of colonies formed by this cell line in a concentration dependent manner. Specifically, at the highest concentration of TA-1 used (150 ug/ml), less than 5% of the expected number of colonies formed (7 colonies compared with the 150 formed on the untreated control group). A nonspecific MAb matched, to the same mouse subtype as TA-1 (both IgG$_1$) had no effect on the number of colonies formed at 150 ug/ml. This growth inhibitory effect appears to be cytostatic and not cytocidal as the cells which do not form colonies in the soft agar are still viable. This result has obvious implications for antibody directed toxin therapy to tumor cells which over express the human neu protein.

Deposit

A deposit was made with the American Type Culture Collection, Rockville, Md. of the antibody-producing cell line BD5-2d, under ATCC accession number HB9689.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A nucleic acid probe capable of detecting a single base difference between a nucleotide sequence present in a previously isolated human ras oncogene and a nucleotide sequence present in a corresponding previously isolated human ras proto-oncogene, wherein the single base difference is responsible for conversion of the proto-oncogene to the oncogene and the single base difference is located in a sequence recognized by a restriction enzyme.

2. The probe of claim 1, wherein the human ras oncogene differs from the human ras proto-oncogene in the codon for position 12.

* * * * *